United States Patent
Strom et al.

(10) Patent No.: US 12,033,749 B2
(45) Date of Patent: Jul. 9, 2024

(54) SYSTEMS AND METHODS FOR TECHNICAL SUPPORT OF CONTINUOUS ANALYTE MONITORING AND SENSOR SYSTEMS

(71) Applicant: DexCom, Inc., San Diego, CA (US)

(72) Inventors: Caroline M. Strom, San Diego, CA (US); Arturo Garcia, Chula Vista, CA (US); Nicole Marie Weikert, La Jolla, CA (US); Apurv Ullas Kamath, San Diego, CA (US); Nolan Rey, La Jolla, CA (US); Aarthi Narain, San Diego, CA (US)

(73) Assignee: Dexcom, Inc., San Diego, CA (US)

( * ) Notice: Subject to any disclaimer, the term of this patent is extended or adjusted under 35 U.S.C. 154(b) by 118 days.

(21) Appl. No.: 17/467,072

(22) Filed: Sep. 3, 2021

(65) Prior Publication Data

US 2021/0398662 A1    Dec. 23, 2021

Related U.S. Application Data

(63) Continuation of application No. 15/805,677, filed on Nov. 7, 2017, now Pat. No. 11,295,855.
(Continued)

(51) Int. Cl.
*G16H 40/40* (2018.01)
*A61B 5/00* (2006.01)
(Continued)

(52) U.S. Cl.
CPC ........... *G16H 40/40* (2018.01); *A61B 5/0002* (2013.01); *A61B 5/0015* (2013.01);
(Continued)

(58) Field of Classification Search
CPC ........ G16H 40/40; G16H 40/67; G16H 50/30; G16H 10/60; A61B 5/0002; A61B 5/0015;
(Continued)

(56) References Cited

U.S. PATENT DOCUMENTS 6,001,067 A    12/1999   Shults et al.
6,424,847 B1    7/2002   Mastrototaro et al.
(Continued)

FOREIGN PATENT DOCUMENTS

EP    2327984 A2    6/2011
JP    H08286779 A    11/1996
(Continued)

OTHER PUBLICATIONS

Mossman, Insulin pumps: design basics and trade-offs, Jun. 14, 2010, Electronic Engineering Times, pp. 48-52. (Year: 2010).*
(Continued)

*Primary Examiner* — Christopher L Gilligan
(74) *Attorney, Agent, or Firm* — Patterson + Sheridan, LLP

(57) ABSTRACT

Certain aspects of the present disclosure relate to methods and systems for technical support of continuous analyte monitoring and sensor systems. In certain aspects, a method includes sensing, by an analyte sensor, analyte levels of a patient to generate one or more sensed signals. The method further includes generating, by a transmitter, a plurality of event indications based on the one or more sensed signals. The method further includes transmitting, by the transmitter, the plurality of event indications to a processor. The method also includes receiving the plurality of event indications indicating one or more errors associated with the analyte sensor. The method further includes determining one or more root causes associated with the plurality of event
(Continued)

indications based on a pattern associated with the plurality of event indications. The method also includes taking one or more actions to resolve the one or more root causes.

29 Claims, 12 Drawing Sheets

Related U.S. Application Data

(60) Provisional application No. 62/419,900, filed on Nov. 9, 2016.

(51) Int. Cl.
| | |
|---|---|
| *A61B 5/145* | (2006.01) |
| *G06F 16/951* | (2019.01) |
| *G16H 40/67* | (2018.01) |
| *G16H 50/30* | (2018.01) |

(52) U.S. Cl.
CPC ...... *A61B 5/14532* (2013.01); *A61B 5/14546* (2013.01); *G06F 16/951* (2019.01); *G16H 40/67* (2018.01); *G16H 50/30* (2018.01)

(58) Field of Classification Search
CPC ............ A61B 5/14532; A61B 5/14546; G06F 16/951
See application file for complete search history.

(56) References Cited

U.S. PATENT DOCUMENTS

| | | | |
|---|---|---|---|
| 6,477,395 B2 | 11/2002 | Schulman et al. | |
| 6,484,046 B1 | 11/2002 | Say et al. | |
| 6,512,939 B1 | 1/2003 | Colvin et al. | |
| 6,565,509 B1 | 5/2003 | Say et al. | |
| 6,579,690 B1 | 6/2003 | Bonnecaze et al. | |
| 6,931,327 B2 | 8/2005 | Goode, Jr. et al. | |
| 7,310,544 B2 | 12/2007 | Brister et al. | |
| 7,946,985 B2 * | 5/2011 | Mastrototaro | A61B 5/14865 600/347 |
| 8,423,113 B2 | 4/2013 | Shariati et al. | |
| 9,172,705 B1 | 10/2015 | Kong et al. | |
| 9,282,925 B2 | 3/2016 | Kamath et al. | |
| 9,804,150 B2 | 10/2017 | Hayter et al. | |
| 10,646,650 B2 | 5/2020 | Cinar et al. | |
| 2005/0027463 A1 | 2/2005 | Goode, Jr. et al. | |
| 2005/0043598 A1 | 2/2005 | Goode, Jr. et al. | |
| 2005/0154271 A1 | 7/2005 | Rasdal et al. | |
| 2005/0192557 A1 | 9/2005 | Brauker et al. | |
| 2005/0203360 A1 | 9/2005 | Brauker et al. | |
| 2006/0020187 A1 | 1/2006 | Brister et al. | |
| 2006/0222566 A1 | 10/2006 | Brauker et al. | |
| 2007/0016381 A1 | 1/2007 | Kamath et al. | |
| 2007/0027385 A1 | 2/2007 | Brister et al. | |
| 2007/0032706 A1 | 2/2007 | Kamath et al. | |
| 2007/0032733 A1 | 2/2007 | Burton | |
| 2007/0197890 A1 | 8/2007 | Boock et al. | |
| 2007/0203966 A1 | 8/2007 | Brauker et al. | |
| 2007/0208245 A1 | 9/2007 | Brauker et al. | |
| 2007/0208246 A1 | 9/2007 | Brauker et al. | |
| 2008/0033254 A1 | 2/2008 | Kamath et al. | |
| 2008/0108942 A1 | 5/2008 | Brister et al. | |
| 2008/0119703 A1 | 5/2008 | Brister et al. | |
| 2009/0043525 A1 | 2/2009 | Brauker et al. | |
| 2009/0057148 A1 | 3/2009 | Wieder et al. | |
| 2009/0192366 A1 | 7/2009 | Mensinger et al. | |
| 2009/0240120 A1 | 9/2009 | Mensinger et al. | |
| 2009/0275805 A1 | 11/2009 | Lane et al. | |
| 2010/0179409 A1 | 7/2010 | Kamath et al. | |
| 2010/0265073 A1 * | 10/2010 | Harper | H04W 4/80 340/573.1 |
| 2010/0292544 A1 | 11/2010 | Sherman et al. | |
| 2012/0310050 A1 | 12/2012 | Osorio | |
| 2013/0076531 A1 | 3/2013 | San Vicente et al. | |
| 2013/0267809 A1 * | 10/2013 | Brister | A61B 5/0004 600/347 |
| 2013/0303869 A1 | 11/2013 | Rebec et al. | |
| 2013/0337571 A1 * | 12/2013 | Mizuoka | G01N 27/3274 436/95 |
| 2014/0012511 A1 * | 1/2014 | Mensinger | G16H 40/40 702/19 |
| 2014/0184422 A1 | 7/2014 | Mensinger et al. | |
| 2014/0187889 A1 | 7/2014 | Cohen et al. | |
| 2014/0207400 A1 | 7/2014 | Hayter et al. | |
| 2015/0199489 A1 | 7/2015 | Muradia | |
| 2015/0226752 A1 | 8/2015 | Nazareth et al. | |
| 2015/0374299 A1 | 12/2015 | Hayter | |
| 2016/0021169 A1 | 1/2016 | Chan | |
| 2016/0120448 A1 | 5/2016 | Hernandez-Rosas et al. | |
| 2016/0217472 A1 | 7/2016 | Podgorny et al. | |
| 2016/0227361 A1 | 8/2016 | Booth et al. | |
| 2016/0346459 A1 | 12/2016 | Chow et al. | |
| 2016/0354543 A1 | 12/2016 | Cinar et al. | |
| 2017/0007129 A1 * | 1/2017 | Kaib | A61N 1/3904 |
| 2017/0367631 A1 * | 12/2017 | Reggiardo | A61B 5/0002 |
| 2018/0103879 A1 * | 4/2018 | Masciotti | A61B 5/0075 |
| 2018/0129784 A1 | 5/2018 | Pal et al. | |
| 2018/0129785 A1 | 5/2018 | Pal et al. | |
| 2018/0286510 A1 | 10/2018 | Kwan et al. | |
| 2019/0216373 A1 * | 7/2019 | Harper | G01N 31/22 |
| 2020/0178868 A1 | 6/2020 | Mueller et al. | |
| 2020/0205694 A1 | 7/2020 | Bohm et al. | |

FOREIGN PATENT DOCUMENTS

| | | | | |
|---|---|---|---|---|
| WO | | 2010127051 A1 | 11/2010 | |
| WO | WO-2010146579 A1 * | | 12/2010 | ........ A61M 5/16831 |

OTHER PUBLICATIONS

Marling C., et al., "Emerging Applications for Intelligent Diabetes Management," 2012, AI Magazine, pp. 67-78.
International Search Report and Written Opinion for Application No. PCT/US2022/075862, mailed Nov. 17, 2022, 13 pages.
Extended European Search Report for Application No. 17869250.5 mailed Jan. 8, 2020, 08 pages.
International Preliminary Report on Patentability for Application No. PCT/US2017/060440 mailed May 23, 2019, 6 pages.
International Search Report and Written opinion for Application No. PCT/US2017/060440 mailed Feb. 1, 2018, 6 pages.

* cited by examiner

SYSTEMS AND METHODS FOR TECHNICAL SUPPORT OF CONTINUOUS ANALYTE MONITORING AND SENSOR SYSTEMS

CROSS-REFERENCE TO RELATED APPLICATION(S)

This application is a continuation-in-part of U.S. patent application Ser. No. 15/805,677 entitled "SYSTEMS AND METHODS FOR TECHNICAL SUPPORT OF CONTINUOUS ANALYTE MONITORING AND SENSOR SYSTEMS," which was filed on Nov. 7, 2017, and which is hereby assigned to the assignee hereof and which claims the benefit of and priority to U.S. Provisional Application No. 62/419,900, entitled "SYSTEMS AND METHODS FOR TECHNICAL SUPPORT OF CONTINUOUS ANALYTE MONITORING AND SENSOR SYSTEMS," which was filed on Nov. 9, 2016, and which is hereby assigned to the assignee hereof. Both U.S. patent application Ser. No. 15/805,677 and U.S. Provisional Application No. 62/419, 900 are hereby expressly incorporated by reference herein in their entirety as if fully set forth below and for all applicable purposes.

TECHNICAL FIELD

The present disclosure relates generally to automated or semi-automated technical support of medical device systems. More particularly, the present disclosure is directed to systems, methods, apparatuses, and computer products for automated or semi-automated technical support of a continuous analyte monitoring system.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically requires uncomfortable finger pricking methods. Due to the lack of comfort and convenience, a diabetic will normally only measure his or her glucose level two to four times per day. Unfortunately, these time intervals are spread so far apart that the diabetic will likely be alerted to a hyperglycemic or hypoglycemic condition too late, sometimes incurring dangerous side effects as a result. In fact, it is not only unlikely that a diabetic will take a timely SMBG value, but will not know if his blood glucose value is going up (higher) or down (lower), due to limitations of conventional methods.

For example, diabetic patients sample their blood glucose levels several times throughout a day, such as in the morning, around lunch, and in the evening. The levels can be measured by taking a small blood sample of the patient and measuring the glucose levels with a test strip or glucose meter. This technique, however, has drawbacks because patients would prefer to not have to take a blood sample, and users do not know what their blood glucose levels are throughout the day between the samples.

Consequently, a variety of non-invasive, transdermal (e.g., transcutaneous) and/or implantable electrochemical sensors have been and are being developed for continuously detecting and/or quantifying glucose values, such as from sensor measurements having accuracy corresponding to direct blood glucose measurements. Continuous glucose monitors have been increasing in popularity as an easy way to monitor glucose levels and automatically alert the patient of glucose level events. For example, one potentially dangerous timeframe is at night because a patient's glucose levels can fall dangerously low during sleep. As a result, continuous glucose monitors have gained popularity by providing a sensor that continuously measures glucose levels of a patient and transmits the measured glucose levels wirelessly to a display. This allows the patient or patient's caregiver to monitor the patient's glucose levels throughout the day and even set alarms for when glucose levels reach a predefined level or experience a defined change.

Initially, continuous glucose monitors wirelessly transmitted data relating to glucose levels to a dedicated display. The dedicated display is a medical device designed to display glucose levels, trending patterns, and other information for a user. However, with the increasing popularity of smart phones and software applications (apps) executing on smart phones, some users prefer to avoid having to carry a dedicated display. Instead, some users prefer to monitor their glucose levels using a dedicated software app executing on their mobile computing device, such as a smart phone, tablet or wearable device like a smartwatch or smart glasses.

While there are many benefits to using a continuous glucose monitoring system, such as increased convenience and added safety, in some cases, continuous glucose monitoring systems have been found to occasionally provide false readings due to one or more errors associated with the continuous glucose monitoring system, including, but not limited to, a prematurely failing and/or failed component of the system. For patients whom solely rely on these systems to accurately track and provide glucose data, these errors may pose a substantial threat to patient health and safety, and in some cases, may be life altering. For this reason, early failure detection is a significant consideration in the design of medical device equipment, including continuous glucose monitoring systems.

SUMMARY

One embodiment includes a continuous analyte monitoring system, wherein the system includes: an analyte sensor configured to sense analyte levels of a patient to generate one or more sensed signals; a transmitter configured to generate a plurality of event indications based on the one or more sensed signals and transmit the plurality of event indications; and a processor configured to: receive the plurality of event indications indicating one or more errors associated with the analyte sensor; determine one or more root causes associated with the plurality of event indications based on a pattern associated with the plurality of event indications; and take one or more actions to resolve the one or more root causes.

In one aspect, each of the plurality of event indications indicates whether the sensed signals are above a maximum configured error threshold or below a minimum configured error threshold.

In another aspect, the pattern associated with the event indications indicates multiple consecutive event indications indicative of the sensed signals being above a maximum configured error threshold.

In another aspect, when the multiple consecutive event indications indicate that the sensed signals are above the maximum configured error threshold, the one or more root causes comprise at least one of: a malfunction associated with the analyte sensor; high sensitivity of the analyte sensor; damage to a membrane of the patient coupled to the analyte sensor; or high moisture condition associated with the analyte sensor.

In another aspect, the continuous analyte monitoring system of claim 4, further comprises a moisture sensor configured to determine a moisture level at an interface between the analyte sensor and the patient to generate moisture detection data, and wherein the processor is further configured to receive the moisture detection data.

In another aspect, the pattern associated with the event indications indicates multiple consecutive event indications indicative of the sensed signals being below a minimum configured error threshold.

In another aspect, when the multiple consecutive event indications indicate that the sensed signals are below the minimum configured error threshold, the one or more root causes comprise at least one of: compression on the analyte sensor; wound trauma at an interface between the analyte sensor and the patient; low sensor sensitivity associated with the analyte sensor; or deteriorated quality of a signal sensed by the analyte sensor.

In another aspect, the one or more sensed signals indicate one or more analyte measurements; the processor is further configured to: receive one or more reference analyte measurements from the patient; and transmit the one or more reference analyte measurements to the transmitter; and the transmitter is further configured to generate the plurality of event indications based on a comparison of the one or more analyte measurements and the one or more reference analyte measurements.

In another aspect, determining the one or more root causes comprises determining that a difference between the one or more analyte measurements and the one or more reference analyte measurements is greater than a threshold; and wherein the one or more root causes comprise deficient sensor calibration.

In another aspect, one or more of the plurality of event indications indicate a rate of change associated with the one or more sensed signals being higher than a threshold.

In another aspect, the transmitter is further configured to apply one or more filters to the one or more sensed signals to produce one or more filtered signals; and each of the plurality of event indications indicates whether a differential between the one more sensed signals and the one or more filtered signals is above a configured threshold.

In another aspect, determining the one or more root causes comprises determining multiple consecutive event indications indicate the differential between the one more sensed signals and the one or more filtered signals is above a configured threshold; and wherein the one or more root causes comprise at least one of: compression on the analyte sensor; or damage to a membrane of the patient coupled to the analyte sensor.

In another aspect, the processor is further configured to receive one or more answers to one or more questions presented to a user, and wherein the determining of the one or more root causes is further based on the one or more answers.

In another aspect, the one or more questions comprise at least one of: the one or more questions comprise at least one of: one or more questions associated with a skin condition of the patient; one or more questions associated with recent activities of the patient; one or more questions associated with one or more health conditions of the patient; one or more questions associated with nutrition of the patient; one or more questions associated with an interface between the analyte sensor and the patient; or one or more questions associated with deployment of the analyte sensor by the patient.

In another aspect, the one or more actions comprise at least one of: indicating to a user to relocate or reorient the analyte sensor on a body of the patient; indicating to the user to change a position of the body of the patient; indicating to the user to change a diet of the patient; indicating to the user to apply a cream to an interface between the analyte sensor and the patient; indicating to the user to apply an agent to an interface between the analyte sensor and the patient; indicating to the user to have the patient digest one or more supplements to increase adhesion of the analyte sensor at the interface between the analyte sensor and the patient; indicating to the user that a specific activity has caused the one or more event indications; indicating to the user to re-calibrate the analyte sensor; indicating to the user to order a new analyte sensor for the patient; or ordering a new analyte sensor for the patient.

In another aspect, the processor is further configured to receive secondary sensor data associated with the patient, wherein the determining of the one or more root causes is further based on the secondary sensor data.

In another aspect, the secondary sensor data comprises at least one: accelerometer data associated with movement of the analyte sensor; temperature data indicating a temperature associated with the analyte sensor; gyrometer data indicating an orientation of the analyte sensor; moisture detection data indicating a moisture level at an interface between the analyte sensor and the patient; or heart sensor data indicating a heart rate of the patient.

In another aspect, the processor is further configured to receive an indication from a server indicating a pattern associated with event indications for a population of patients, wherein determining the one or more root causes is further based on the pattern associated with the event indications for the population.

In another aspect, the processor is further configured to: generate an event indication indicative of one or more errors associated with the transmitter, an application executed by the processor, one or more other connected devices, or one or more applications executing on the one or more other connected devices; and determine one or more other root causes associated with the event indication generated by the processor.

In another aspect, the event indication generated by the processor indicates an issue with a battery of the transmitter.

In another aspect, the processor is further configured to determine whether a warranty period associated with the transmitter has expired, wherein the one or more actions comprise: indicating to a user to order a new transmitter for the patient upon determining the warranty period has expired; or ordering a new transmitter for the patient upon determining the warranty period has not expired.

In another aspect, the event indication generated by the processor indicates an initial pairing between the transmitter and the processor has failed.

In another aspect, the event indication generated by the processor indicates that a connection between the transmitter and the processor has been lost for a period greater than a threshold; and wherein the processor is further configured to indicate to a user to take one or more remedial actions comprising, at least one of: indicating to a user to disable and re-enable a Bluetooth function on a device where the processor is running; indicating to the user to power cycle the device where the processor is running; or indicating to the user to uninstall and re-install the application executed by the processor.

In another aspect, the one or more actions comprise at least one of: indicating to a user to uninstall and re-install the application executed by the processor; or indicating to the user to reopen the application executed by the processor.

In another aspect, the event indication generated by the processor indicates an initial pairing between the one or more other connected devices and the processor has failed.

In another aspect, the initial pairing fails due, at least in part, to the one or more other connected devices refusing authorization of the processor.

In another aspect, the event indication generated by the processor indicates receipt, by the processor, of incorrect data transmitted by the one or more applications executing on the one or more other connected devices.

Another embodiment includes a method where the method includes: sensing, by an analyte sensor, analyte levels of a patient to generate one or more sensed signals; generating, by a transmitter, a plurality of event indications based on the one or more sensed signals; transmitting, by the transmitter, the plurality of event indications to a processor; receiving, by the processing, the plurality of event indications indicating one or more errors associated with the analyte sensor; determining, by the processor, one or more root causes associated with the plurality of event indications based on a pattern associated with the plurality of event indications; and taking, by the processor, one or more actions to resolve the one or more root causes.

In one aspect, the method further comprises generating, by the processor, an event indication indicative of one or more errors associated with the transmitter, an application executed by the processor, one or more other connected devices, or one or more applications executing on the one or more other connected devices; and determining, by the processor, one or more other root causes associated with the event indication generated by the processor.

BRIEF DESCRIPTION OF THE DRAWINGS

Further aspects of the present disclosure will be more readily appreciated upon review of the detailed description of the various disclosed embodiments, described below, when taken in conjunction with the accompanying figures.

Figure 1A:
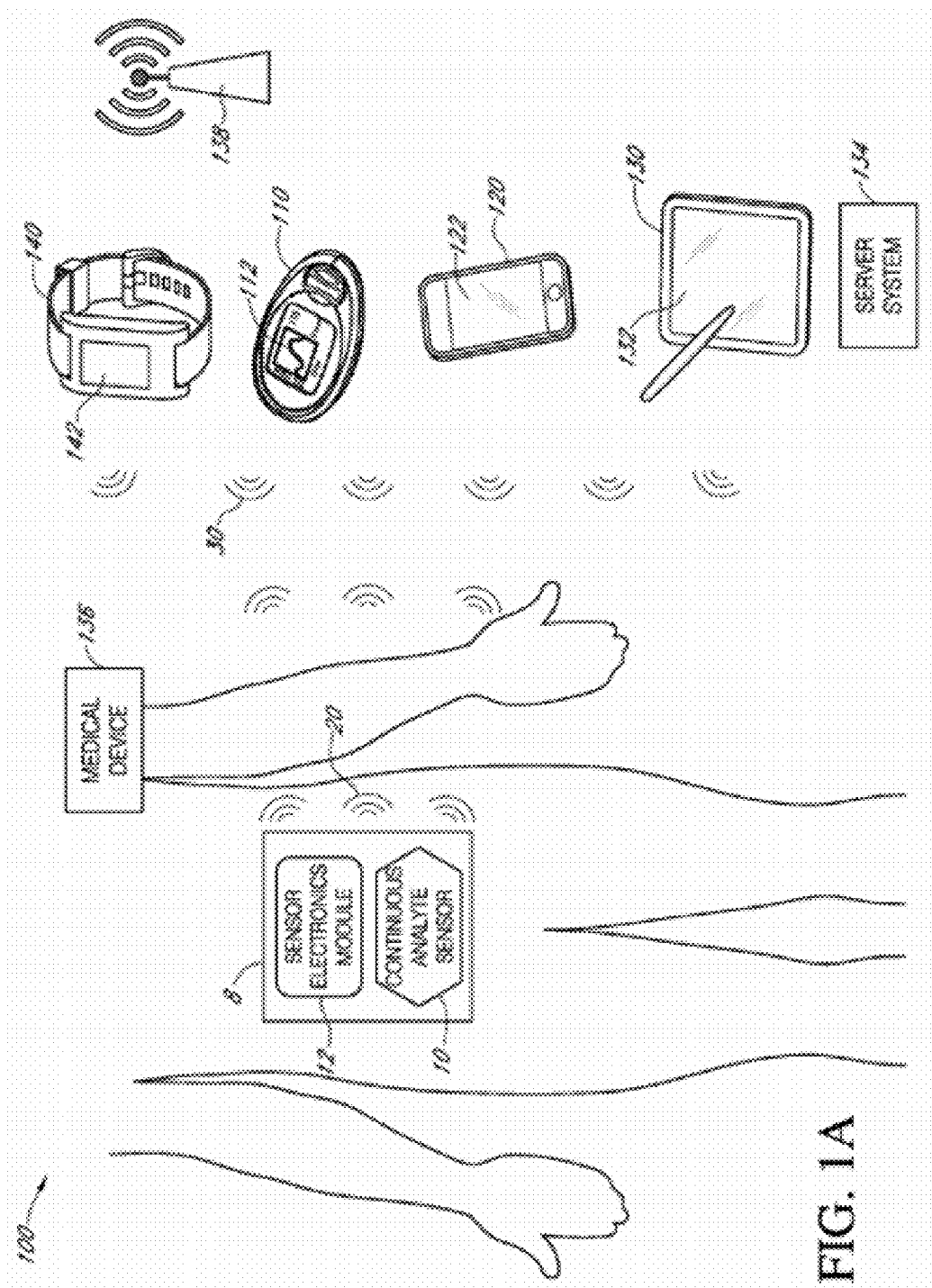
FIG. 1A illustrates aspects of an example system that may be used in connection with implementing embodiments of the disclosure.

The figures are described in greater detail in the description and examples below, are provided for purposes of illustration only, and merely depict typical or example embodiments of the disclosure. The figures are not intended to be exhaustive or to limit the disclosure to the precise form disclosed. It should also be understood that the disclosure may be practiced with modification or alteration, and that the disclosure may be limited only by the claims and the equivalents thereof.

DETAILED DESCRIPTION

The convenience and added safety of using modern continuous glucose monitoring systems have led to an increase in the number of diabetes patients using such systems. With increased usage, the patients' need for efficient technical support has also increased. Providing technical support of medical devices often entails compliance with government regulatory regimes directed to these devices. For example, medical device providers are sometimes under an obligation to track and record data related to detection and resolution of technical issues encountered by patients.

Additionally, a modern medical device provider has its internal systems and procedures that may be triggered with each patient request for technical support as well as technical support personnel on standby to aid in resolving one or more issues related to a patient's medical device. For example, users (e.g., where a user is the patient, caretaker of the patient, physician of the patient, etc.) wishing to obtain technical assistance to resolve component failure or other performance problems related to their medical device generally need to contact technical support personnel and provide a complete set of relevant information needed by technical support personnel to accurately and efficiently solve the one or more issues reported by the user. Providing a complete set of relevant information needed by technical support personnel to accurately and efficiently solve maintenance problems may, in some cases, require answering questions which the patient may not know, may not recall, or may inaccurately report to technical support. Moreover, unexpected device or system performance anomalies may be the result of seemingly unrelated changes to a patient's daily routine, nutrition, activities, etc., thus the user may not have the requisite level of knowledge to provide valuable information to technical support for determining a root cause of the technical issue. Therefore, conventional methods for technical support may not be efficient and in some cases, may fail to accurately identify and solve the issue because all necessary information is not obtained or the information obtained is erroneous. Accordingly, integrity of the medical device may be compromised given the correct root cause was unidentified and therefore, not corrected. For patients whom solely rely on these medical devices to accurately track and provide data, these uncorrected errors may pose a substantial threat to patient health and safety, and in some cases, may be life altering, especially when they relate to a failing component or a failed component of the device.

Further, as patient population utilizing modern medical devices increases, so does the volume of patients requesting technical support. Thus, conventional methods requiring manual intervention by technical support personnel may not be able to be scalable, nor efficient, to meet such increased demands.

Consequently, there is a need for automated or semi-automated technical support systems to provide improved and efficient technical support to users of modern medical devices and associated infrastructure.

Embodiments of the present disclosure are directed to systems, methods, and devices for providing automated or semi-automated technical support solutions. In various deployments described herein, the analyte data is glucose data generated by an analyte sensor system configured to connect to display devices and the like. Implementing aspects of the present disclosure, as described in detail herein, can establish systems and methods capable of providing automated or semi-automated technical support for a government-regulated medical device.

In particular, some aspects of the disclosure relate to enabling remote initiation of a request for automatic tech support, performing government-compliant recording of a tech support incident and enabling alerts or reports to internal departments within a medical device provider to improve medical device products and services.

Further, some other aspects of the disclosure relate to a continuous analyte monitoring system, including an analyte sensor system having at least an analyte sensor and a transmitter in communication with at least a display device having a processor. The continuous analyte monitoring system described herein is configured to automatically self-diagnose and resolve performance problems detected and associated with components of and/or associated with the continuous analyte monitoring system, the components including the analyte sensor of the analyte sensor system, the transmitter of the analyte sensor system, an application executed by the processor of the display device in communication with the analyte sensor system, and/or one or more other devices connected to the display device and/or applications executing on such connected devices.

In particular, at least one of the transmitter or processor of the continuous analyte monitoring system may be configured to generate a plurality of event indications. As used herein, the term "event indication" may refer to an indication that an error has occurred with respect to one or more components of and/or associated with the continuous analyte monitoring system. For example, based on analyte data continuously measured by the analyte sensor, the transmitter may generate an event indication to indicate that the analyte data consists of unusual, possibly incorrect, data. The transmitter may attribute this unusual data to an error associated with the analyte sensor by generating an event indication.

Generated event indications may be analyzed by the processor. In particular, the processor may include a prediction algorithm capable of detecting component failure when or before it occurs. The prediction algorithm may be configured to (1) determine whether an event indication is related to premature failure or failure of a device and/or an application associated with the continuous analyte monitoring system, or in the alternative, whether the event indication is a false positive premature failure or failure detection and (2) further ascertain a root cause of the false positive indication. As used herein, the term "failure" may refer to a state of a component when the component is unable to perform or function as intended, including any deviations from the component's performance specifications or intended use. Further, the terms "premature failure" and "early failure" are used interchangeably and generally refer to a state of a component prior to failure.

The details of some example embodiments of the systems, methods, and devices of the present disclosure are set forth in this description and in some cases, in other portions of the disclosure. Other features, objects, and advantages of the disclosure will be apparent to one of skill in the art upon examination of the present disclosure, description, figures, examples, and claims. It is intended that all such additional systems, methods, devices, features, and advantages be included within this description (whether explicitly or by reference), be within the scope of the present disclosure, and be protected by one or more of the accompanying claims.

Overview

In some embodiments, a system is provided for continuous measurement of an analyte in a patient. The system may be referred to herein as an analyte sensor system. According to certain aspects, the analyte sensor system may be part of a larger continuous analyte monitoring system, including the analyte sensor system in communication with at least one display device.

The analyte sensor system may include: a continuous analyte sensor configured to continuously measure a concentration of the analyte in the patient, and a sensor electronics module physically connected to the continuous analyte sensor during sensor use. In certain embodiments, the sensor electronics module includes electronics configured to process a data stream associated with an analyte concentration measured by the continuous analyte sensor, in order to generate sensor information that includes raw sensor data, transformed sensor data, and/or any other sensor data, for example. The sensor electronics module may further be configured to generate sensor information that is customized for respective display devices, such that different display devices may receive different sensor information.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid, urine, sweat, saliva, etc.) that can be analyzed. Analytes can include naturally occurring substances, artificial substances, metabolites, and/or reaction products. In some implementations, the analyte for measurement by the methods or devices is glucose. However, other analytes are contemplated as well, including but not limited to: acarboxyprothrombin; acetoacetic acid;

acetone; Acetyl CoA; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; triglycerides; glycerol; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyl-transferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; ketone bodies; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, isoprene (2-methyl-1,3-butadiene), *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi/rangeli*, vesicular *stomatis* virus, *Wuchereria bancrofti*, Flavivirus (for example deer tick, dengue fever, Powassan, West Nile, yellow fever, or Zika virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain implementations. The analyte can be naturally present in the biological fluid, for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin; glucagon, ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA), and intermediaries in the Citric Acid Cycle.

While the analyte for measurement and analysis by the devices and methods described herein is glucose, other analytes listed, but not limited to, above may be considered. Biological parameters, such as body temperature, heart rate, metabolic function, respiratory rate, and the like, may be also be considered.

Alerts

In certain embodiments, one or more alerts are associated with a sensor electronics module. For example, each alert may include one or more alert conditions that indicate when the respective alert has been triggered. For example, a hypoglycemic alert may include alert conditions indicating a minimum glucose level. The alert conditions may also be based on transformed sensor data, such as trending data, and/or sensor data from multiple different sensors (e.g., an alert may be based on sensor data from both a glucose sensor and a temperature sensor). For example, a hypoglycemic alert may include alert conditions indicating a minimum required trend in the host's glucose level that must be present before triggering the alert. The term "trend," as used herein refers generally to data indicating some attribute of data that is acquired over time, such as calibrated or filtered data from a continuous glucose sensor. A trend may indicate amplitude, rate of change, acceleration, direction, etc., of data, such as sensor data, including transformed or raw sensor data.

In certain embodiments, each of the alerts is associated with one or more actions that are to be performed in response to triggering of the alert. Alert actions may include, for example, activating an alarm, such as displaying information on a display of the sensor electronics module or activating an audible or vibratory alarm coupled to the sensor electronics module, and/or transmitting data to one or more display devices external to the sensor electronics module. For any delivery action that is associated with a triggered alert, one or more delivery options define the content and/or format of the data to be transmitted, the device to which the data is to be transmitted, when the data is to be transmitted, and/or a communication protocol for delivery of the data.

In certain embodiments, multiple delivery actions (each having respective delivery options) may be associated with a single alert such that displayable sensor information having different content and formatting, for example, is transmitted to respective display devices in response to triggering of a single alert. For example, a mobile telephone may receive a data package including minimal displayable sensor information (that may be formatted specifically for display on the mobile telephone), while a desktop computer may receive a data package including most (or all) of the displayable sensor information that is generated by the sensor electronics module in response to triggering of a common alert. Advantageously, the sensor electronics module is not tied to a single display device, rather it is configured to communicate with a plurality of different display devices directly, systematically, simultaneously (e.g., via broadcasting), regularly, periodically, randomly, on-demand, in response to a query, based on alerts or alarms, and/or the like.

In some embodiments, clinical risk alerts are provided that include alert conditions that combine intelligent and dynamic estimative algorithms that estimate present or predicted danger with greater accuracy, more timeliness in pending danger, avoidance of false alarms, and less annoyance for the patient. In general, clinical risk alerts include dynamic and intelligent estimative algorithms based on analyte value, rate of change, acceleration, clinical risk, statistical probabilities, known physiological constraints, and/or individual physiological patterns, thereby providing more appropriate, clinically safe, and patient-friendly alarms. U.S. Patent Publication No. 2007/0208246, which is incorporated herein by reference in its entirety, describes some systems and methods associated with the clinical risk alerts (or alarms) described herein. In some embodiments, clinical risk alerts can be triggered for a predetermined time period to allow for the user to attend to his/her condition. Additionally, the clinical risk alerts can be de-activated when leaving a clinical risk zone so as not to annoy the patient by repeated clinical alarms (e.g., visual, audible or vibratory), when the patient's condition is improving. In some embodiments, dynamic and intelligent estimation determines a possibility of the patient avoiding clinical risk, based on the analyte concentration, the rate of change, and other aspects of the dynamic and intelligent estimative algorithms. If there is minimal or no possibility of avoiding the clinical risk, a clinical risk alert will be triggered. However, if there is a possibility of avoiding the clinical risk, the system is configured to wait a predetermined amount of time and re-analyze the possibility of avoiding the clinical risk. In some embodiments, when there is a possibility of avoiding the clinical risk, the system is further configured to provide targets, therapy recommendations, or other information that can aid the patient in proactively avoiding the clinical risk.

In some embodiments, the sensor electronics module is configured to search for one or more display devices within communication range of the sensor electronics module and to wirelessly communicate sensor information (e.g., a data package including displayable sensor information, one or more alarm conditions, and/or other alarm information) thereto. Accordingly, the display device is configured to display at least some of the sensor information and/or alarm the host (and/or care taker), wherein the alarm mechanism is located on the display device.

In some embodiments, the sensor electronics module is configured to provide one or a plurality of different alarms via the sensor electronics module and/or via transmission of a data package indicating an alarm should be initiated by one or a plurality of display devices (e.g., sequentially and/or simultaneously). In certain embodiments, the sensor electronics module merely provides a data field indicating that an alarm conditions exists and the display device, upon reading the data field indicating the existence of the alarm condition, may decide to trigger an alarm. In some embodiments, the sensor electronics module determines which of the one or more alarms to trigger based on one or more alerts that are triggered. For example, when an alert trigger indicates severe hypoglycemia, the sensor electronics module can perform multiple actions, such as activating an alarm on the sensor electronics module, transmitting a data package to a monitoring device indicating activation of an alarm on the display, and transmitting a data package as a text message to a care provider. As an example, a text message can appear on a custom monitoring device, cell phone, pager device, and/or the like, including displayable sensor information that indicates the host's condition (e.g., "severe hypoglycemia").

In some embodiments, the sensor electronics module is configured to wait a time period for the host to respond to a triggered alert (e.g., by pressing or selecting a snooze and/or off function and/or button on the sensor electronics module and/or a display device), after which additional alerts are triggered (e.g., in an escalating manner) until one or more alerts are responded to. In some embodiments, the sensor electronics module is configured to send control signals (e.g., a stop signal) to a medical device associated with an alarm condition (e.g., hypoglycemia), such as an insulin pump, wherein the stop alert triggers a stop of insulin delivery via the pump.

In some embodiments, the sensor electronics module is configured to directly, systematically, simultaneously (e.g., via broadcasting), regularly, periodically, randomly, on-demand, in response to a query (from the display device), based on alerts or alarms, and/or the like transmit alarm information. In some embodiments, the system further includes a repeater such that the wireless communication distance of the sensor electronics module can be increased, for example, to 10, 20, 30, 50 75, 100, 150, or 200 meters or more, wherein the repeater is configured to repeat a wireless communication from the sensor electronics module to the display device located remotely from the sensor electronics module. A repeater can be useful to families having children with diabetes. For example, to allow a parent to carry, or place in a stationary position, a display device, such as in a large house wherein the parents sleep at a distance from the child.

Display Devices

In some embodiments, the sensor electronics module is configured to search for and/or attempt wireless communication with a display device from a list of display devices. In some embodiments, the sensor electronics module is configured to search for and/or attempt wireless communication with a list of display devices in a predetermined and/or programmable order (e.g., grading and/or escalating), for example, wherein a failed attempt at communication with and/or alarming with a first display device triggers an attempt at communication with and/or alarming with a second display device, and so on. In one example embodiment, the sensor electronics module is configured to search for and attempt to alarm a host or care provider sequentially using a list of display devices, such as: (1) a default display device or a custom analyte monitoring device; (2) a mobile phone via auditory and/or visual methods, such as, text message to the host and/or care provider, voice message to the host and/or care provider, and/or 911); (3) a tablet; (4) a smart watch or bracelet; and/or (5) smart glasses or other wearable display device.

Depending on the embodiment, one or more display devices that receive data packages from the sensor electronics module are "dummy displays", wherein they display the displayable sensor information received from the sensor electronics module without additional processing (e.g., prospective algorithmic processing necessary for real-time display of sensor information). In some embodiments, the displayable sensor information comprises transformed sensor data that does not require processing by the display device prior to display of the displayable sensor information. Some display devices may include software including display instructions (software programming comprising instructions configured to display the displayable sensor information and optionally query the sensor electronics module to obtain the displayable sensor information) configured to enable display of the displayable sensor information thereon. In some embodiments, the display device is programmed with the display instructions at the manufacturer and can include security and/or authentication to avoid plagiarism of the display device. In some embodiments, a display device is configured to display the displayable sensor information via a downloadable program (for example, a downloadable Java Script via the internet), such that any display device that supports downloading of a program (for example, any display device that supports Java applets) therefore can be configured to display displayable sensor information (e.g., mobile phones, tablets, PDAs, PCs and the like).

In some embodiments, certain display devices may be in direct wireless communication with the sensor electronics module, but intermediate network hardware, firmware, and/or software can be included within the direct wireless communication. In some embodiments, a repeater (e.g., a Bluetooth repeater) can be used to re-transmit the transmitted displayable sensor information to a location farther away than the immediate range of the telemetry module of the sensor electronics module, wherein the repeater enables direct wireless communication when substantive processing of the displayable sensor information does not occur. In some embodiments, a receiver (e.g., Bluetooth receiver) can be used to re-transmit the transmitted displayable sensor information, possibly in a different format, such as in a text message onto a TV screen, wherein the receiver enables direct wireless communication when substantive processing of the sensor information does not occur. In certain embodiments, the sensor electronics module directly wirelessly transmits displayable sensor information to one or a plurality of display devices, such that the displayable sensor information transmitted from the sensor electronics module is received by the display device without intermediate processing of the displayable sensor information.

In certain embodiments, one or more display devices include built-in authentication mechanisms, wherein authentication is required for communication between the sensor electronics module and the display device. In some embodiments, to authenticate the data communication between the sensor electronics module and display devices, a challenge-response protocol, such as a password authentication is provided, where the challenge is a request for the password and the valid response is the correct password, such that pairing of the sensor electronics module with the display devices can be accomplished by the user and/or manufacturer via the password. This may be referred to in some cases as two-way authentication.

In some embodiments, one or more display devices are configured to query the sensor electronics module for displayable sensor information, wherein the display device acts as a master device requesting sensor information from the sensor electronics module (e.g., a slave device) on-demand, for example, in response to a query. In some embodiments, the sensor electronics module is configured for periodic, systematic, regular, and/or periodic transmission of sensor information to one or more display devices (for example, every 1, 2, 5, or 10 minutes or more). In some embodiments, the sensor electronics module is configured to transmit data packages associated with a triggered alert (e.g., triggered by one or more alert conditions). However, any combination of the above described statuses of data transmission can be implemented with any combination of paired sensor electronics module and display device(s). For example, one or more display devices can be configured for querying the sensor electronics module database and for receiving alarm information triggered by one or more alarm conditions being met. Additionally, the sensor electronics module can be configured for periodic transmission of sensor information to one or more display devices (the same or different display devices as described in the previous example), whereby a system can include display devices that function differently with regard to how sensor information is obtained.

In some embodiments, a display device is configured to query the data storage memory in the sensor electronics module for certain types of data content, including direct queries into a database in the sensor electronics module's memory and/or requests for configured or configurable packages of data content therefrom; namely, the data stored in the sensor electronics module is configurable, queryable, predetermined, and/or pre-packaged, based on the display device with which the sensor electronics module is communicating. In some additional or alternative embodiments, the sensor electronics module generates the displayable sensor information based on its knowledge of which display device is to receive a particular transmission. Additionally, some display devices are capable of obtaining calibration information and wirelessly transmitting the calibration information to the sensor electronics module, such as through manual entry of the calibration information, automatic delivery of the calibration information, and/or an integral reference analyte monitor incorporated into the display device. U.S. Patent Publication Nos. 2006/0222566, 2007/0203966, 2007/0208245, and 2005/0154271, all of which are incorporated herein by reference in their entirety, describe systems and methods for providing an integral reference analyte monitor incorporated into a display device and/or other calibration methods that can be implemented with embodiments disclosed herein.

In general, a plurality of display devices (e.g., a custom analyte monitoring device (which may also be referred to as an analyte display device), a mobile phone, a tablet, a smart watch, a reference analyte monitor, a drug delivery device, a medical device and a personal computer) may be configured to wirelessly communicate with the sensor electronics module. The plurality of display devices may be configured to display at least some of the displayable sensor information wirelessly communicated from the sensor electronics module. The displayable sensor information may include sensor data, such as raw data and/or transformed sensor data, such as analyte concentration values, rate of change information, trend information, alert information, sensor diagnostic information and/or calibration information, for example.

Analyte Sensor

With reference to FIG. 1A, in some embodiments, analyte sensor 10 includes a continuous analyte sensor, for example, a subcutaneous, transdermal (e.g., transcutaneous), or intravascular device. In some embodiments, such a sensor or device can analyze a plurality of intermittent blood samples. While the present disclosure includes embodiments of glucose sensors, such embodiments may be used for other analytes as well. The glucose sensor can use any method of glucose-measurement, including enzymatic, chemical, physical, electrochemical, spectrophotometric, polarimetric, calorimetric, iontophoretic, radiometric, immunochemical, and the like.

A glucose sensor can use any known method, including invasive, minimally invasive, and non-invasive sensing techniques (e.g., fluorescent monitoring), to provide a data stream indicative of the concentration of glucose in a host. The data stream is typically a raw data signal, which is converted into a calibrated and/or filtered data stream that is used to provide a useful value of glucose to a user, such as a patient or a caretaker (e.g., a parent, a relative, a guardian, a teacher, a doctor, a nurse, or any other individual that has an interest in the well-being of the host).

A glucose sensor can be any device capable of measuring the concentration of glucose. According to one example embodiment described below, an implantable glucose sensor may be used. However, it should be understood that the devices and methods described herein can be applied to any device capable of detecting a concentration of glucose and providing an output signal that represents the concentration of glucose (e.g., as a form of analyte data).

In certain embodiments, analyte sensor 10 is an implantable glucose sensor, such as described with reference to U.S. Pat. No. 6,001,067 and U.S. Patent Publication No. US-2005-0027463-A1. In some embodiments, analyte sensor 10 is a transcutaneous glucose sensor, such as described with reference to U.S. Patent Publication No. US-2006-0020187-A1. In some embodiments, analyte sensor 10 is configured to be implanted in a host vessel or extracorporeally, such as is described in U.S. Patent Publication No. 2007/0027385A1, co-pending U.S. Patent Publication No. 2008/0119703A1 filed Oct. 4, 2006, U.S. Patent Publication No. 2008/0108942A1 filed on Mar. 26, 2007, and U.S. Patent Application No. 2007/0197890A1 filed on Feb. 14, 2007. In some embodiments, the continuous glucose sensor includes a transcutaneous sensor such as described in U.S. Pat. No. 6,565,509 to Say et al., for example. In some embodiments, analyte sensor 10 is a continuous glucose sensor that includes a subcutaneous sensor such as described with reference to U.S. Pat. No. 6,579,690 to Bonnecaze et al. or U.S. Pat. No. 6,484,046 to Say et al., for example. In some embodiments, the continuous glucose sensor includes a refillable subcutaneous sensor such as described with reference to U.S. Pat. No. 6,512,939 to Colvin et al., for example. The continuous glucose sensor may include an intravascular sensor such as described with reference to U.S. Pat. No. 6,477,395 to Schulman et al., for example. The continuous glucose sensor may include an intravascular sensor such as described with reference to U.S. Pat. No. 6,424,847 to Mastrototaro et al., for example.

Figure 2A:
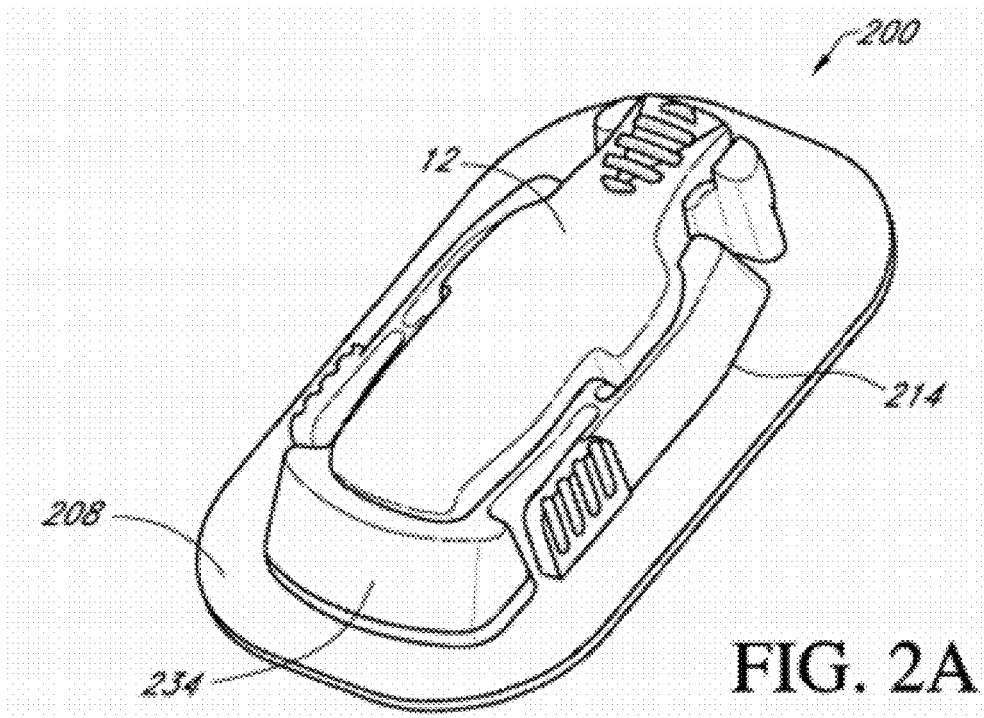
FIG. 2A is a perspective view of an example enclosure that may be used in connection with implementing embodiments of an analyte sensor system.
Figure 2B:
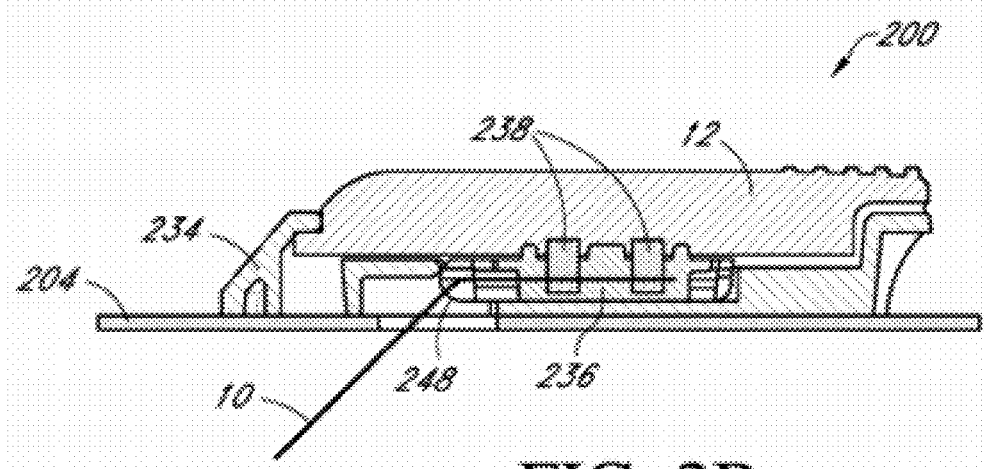
FIG. 2B is a side view of an example enclosure that may be used in connection with implementing embodiments of an analyte sensor system.

FIGS. 2A and 2B are perspective and side views of enclosure 200 that may be used in connection with implementing some embodiments of analyte sensor system 8, according to certain aspects of the present disclosure. Enclosure 200 includes mounting unit 214 and sensor electronics module 12 attached thereto in certain embodiments. Enclosure 200 is shown in a functional position, including mounting unit 214 and sensor electronics module 12 matingly engaged therein. In some embodiments, mounting unit 214, also referred to as a housing or sensor pod, includes base 234 adapted for fastening to a host's or user's skin. Base 234 can be formed from a variety of hard or soft materials, and can include a low profile for minimizing protrusion of the device from the host during use. In some embodiments, base 234 is formed at least partially from a flexible material, which may provide numerous advantages over other transcutaneous sensors, which, unfortunately, can suffer from motion-related artifacts associated with the host's movement when the host is using the device. Mounting unit 214 and/or sensor electronics module 12 can be located over the sensor insertion site to protect the site and/or provide a minimal footprint (utilization of surface area of the host's skin).

In some embodiments, a detachable connection between mounting unit 214 and sensor electronics module 12 is provided, which enables improved manufacturability, namely, the potentially relatively inexpensive mounting unit 214 can be disposed of when refurbishing or maintaining analyte sensor system 8, while the relatively more expensive sensor electronics module 12 can be reusable with multiple sensor systems. In some embodiments, sensor electronics module 12 is configured with signal processing (programming), for example, configured to filter, calibrate, and/or execute other algorithms useful for calibration and/or display of sensor information. However, an integral (non-detachable) sensor electronics module can be configured.

In some embodiments, contacts 238 are mounted on or in a subassembly hereinafter referred to as contact subassembly 236 configured to fit within base 234 of mounting unit 214 and hinge 248 that allows contact subassembly 236 to pivot between a first position (for insertion) and a second position (for use) relative to mounting unit 214. The term "hinge" as used herein is a broad term and is used in its ordinary sense, including, without limitation, to refer to any of a variety of pivoting, articulating, and/or hinging mechanisms, such as an adhesive hinge, a sliding joint, and the like; the term hinge does not necessarily imply a fulcrum or fixed point about which the articulation occurs. In some embodiments, contacts 238 are formed from a conductive elastomeric material, such as a carbon black elastomer, through which sensor 10 extends.

With further reference to FIGS. 2A and 2B, in certain embodiments, mounting unit 214 is provided with adhesive pad 208, disposed on the mounting unit's back surface and includes a releasable backing layer. Thus, removing the backing layer and pressing at last a portion of base 234 of mounting unit 214 onto the host's skin adheres mounting unit 214 to the host's skin. Additionally or alternatively, an adhesive pad can be placed over some or all of analyte sensor system 8 and/or sensor 10 after sensor insertion is complete to ensure adhesion, and optionally to ensure an airtight seal or watertight seal around the wound exit-site (or sensor insertion site) (not shown). Appropriate adhesive pads can be chosen and designed to stretch, elongate, conform to, and/or aerate the region (e.g., host's skin). The embodiments described with reference to FIGS. 2A and 2B are described in more detail with reference to U.S. Pat. No. 7,310,544, which is incorporated herein by reference in its entirety. Configurations and arrangements can provide water resistant, waterproof, and/or hermetically sealed properties associated with the mounting unit/sensor electronics module embodiments described herein.

Various methods and devices that are suitable for use in conjunction with aspects of some embodiments are disclosed in U.S. Patent Publication No. 2009/0240120A1, which is incorporated herein by reference in its entirety for all purposes.

Example Configurations

Referring again to FIG. 1A, system 100 that may be used in connection with implementing aspects of an analyte sensor system is depicted. In some cases, system 100 may be used to implement various systems described herein. System 100 in some embodiments includes analyte sensor system 8 and display devices 110, 120, 130, and 140, according to certain aspects of the present disclosure. Analyte sensor system 8 in the illustrated embodiment includes sensor electronics module 12 and continuous analyte sensor 10 associated with the sensor electronics module 12. Sensor electronics module 12 may be in wireless communication (e.g., directly or indirectly) with one or more of display devices 110, 120, 130, and 140. In some embodiments, system 100 also includes medical device 136 and server system 134. Sensor electronics module 12 may also be in wireless communication (e.g., directly or indirectly) with medical device 136 and server system 134. In some examples, display devices 110-140 may also be in wireless communication with the server system 134 and/or the medical device 136.

In certain embodiments, sensor electronics module 12 includes electronic circuitry associated with measuring and processing the continuous analyte sensor data, including prospective algorithms associated with processing and calibration of the sensor data. Sensor electronics module 12 can be physically connected to continuous analyte sensor 10 and can be integral with (non-releasably attached to) or releasably attachable to continuous analyte sensor 10. Sensor electronics module 12 may include hardware, firmware, and/or software that enables measurement of levels of the analyte via a glucose sensor. For example, sensor electronics module 12 can include a potentiostat, a power source for providing power to the sensor, other components useful for signal processing and data storage, and a telemetry module for transmitting data from the sensor electronics module to one or more display devices. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor.

Sensor electronics module 12 may include sensor electronics that are configured to process sensor information, such as sensor data, and generate transformed sensor data and displayable sensor information. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entirety for all purposes.

Referring again to FIG. 1A, display devices 110, 120, 130, and/or 140 are configured for displaying (and/or alarming) the displayable sensor information that may be transmitted by sensor electronics module 12 (e.g., in a customized data package that is transmitted to the display devices based on their respective preferences). Each of display devices 110, 120, 130, or 140 can include a display such as a touchscreen display 112, 122, 132, /or 142 for displaying sensor information and/or analyte data to a user and/or receiving inputs from the user. For example, a graphical user interface may be presented to the user for such purposes. In some embodiments, the display devices may include other types of user interfaces such as voice user interface instead of or in addition to a touchscreen display for communicating sensor information to the user of the display device and/or receiving user inputs. In some embodiments, one, some, or all of the display devices is configured to display or otherwise communicate the sensor information as it is communicated from the sensor electronics module (e.g., in a data package that is transmitted to respective display devices), without any additional prospective processing required for calibration and real-time display of the sensor data.

Figure 1B:
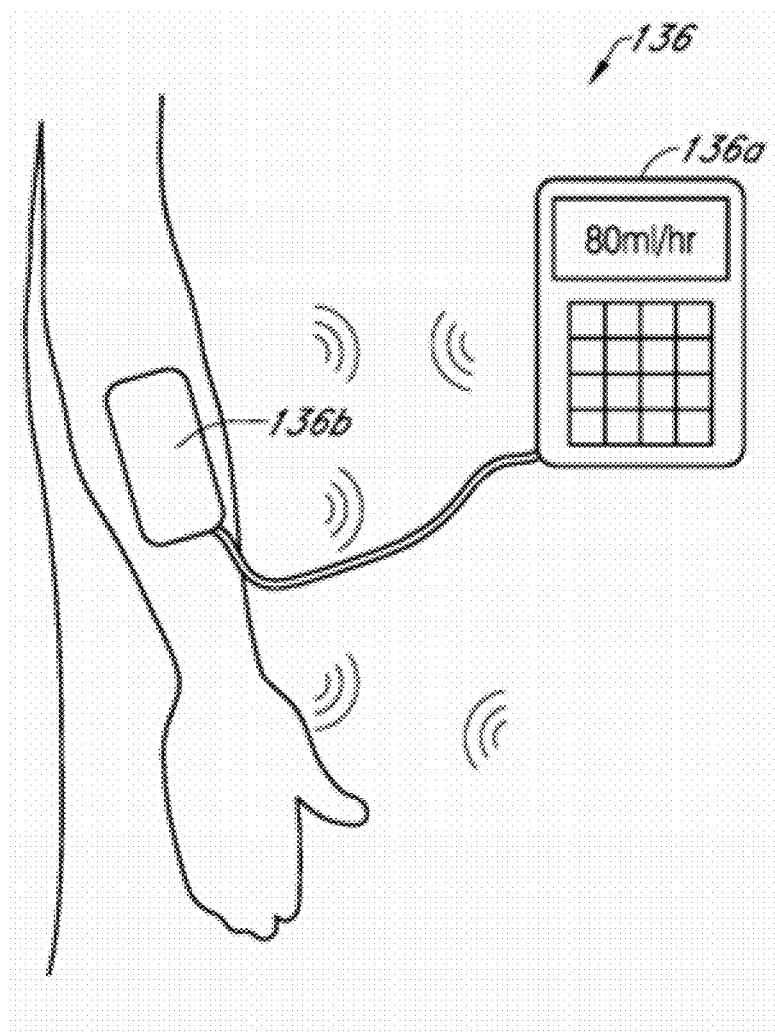
FIG. 1B illustrates aspects of an example system that may be used in connection with implementing embodiments of the disclosure.

Medical device 136 may be a passive device in some example embodiments of the disclosure. For example medical device 136 may be an insulin pump for administering insulin to a user, as shown in FIG. 1B. For a variety of reasons, it may be desirable for such an insulin pump to receive and track glucose values transmitted from analyte sensor system 8. One reason is to provide the insulin pump a capability to suspend or activate insulin administration when a glucose value falls below a threshold value. One solution that allows a passive device (e.g., medical device 136) to receive analyte data (e.g., glucose values) without being bonded to analyte sensor system 8 is to include the analyte data in the advertisement messages transmitted from analyte sensor system 8. The data included in the advertisement messages can be encoded so that only a device that has the identification information associated with analyte sensor system 8 can decode the analyte data. In some embodiments, the medical device 136 includes a sensor apparatus 136b, e.g., attachable or wearable by the user, in wired or wireless communication with a dedicated monitor or display apparatus 136a to process sensor data and/or display data from the sensor apparatus 136a and/or receive input for operation of the sensor apparatus and/or data processing.

With further reference to FIG. 1A, the plurality of display devices may include a custom display device specially designed for displaying certain types of displayable sensor information associated with analyte data received from sensor electronics module 12 (e.g., a numerical value and an arrow, in some embodiments). Analyte display device 110 is an example of such a custom device. In some embodiments, one of the plurality of display devices is smartphone, such as mobile phone 120 based on an Android, iOS or other operating system, and configured to display a graphical representation of the continuous sensor data (e.g., including current and historic data). Other display devices can include other hand-held devices, such as tablet 130, smart watch 140, medical device 136 (e.g., an insulin delivery device or a blood glucose meter), and/or a desktop or laptop computer.

Because different display devices provide different user interfaces, content of the data packages (e.g., amount, format, and/or type of data to be displayed, alarms, and the like) can be customized (e.g., programmed differently by the manufacture and/or by an end user) for each particular display device. Accordingly, in some implementations of the embodiment of FIG. 1A, a plurality of different display devices can be in direct wireless communication with a sensor electronics module (e.g., such as an on-skin sensor electronics module 12 that is physically connected to the continuous analyte sensor 10) during a sensor session to enable a plurality of different types and/or levels of display and/or functionality associated with the displayable sensor information, which is described in more detail elsewhere herein.

As further illustrated in FIG. 1A, system 100 may also include wireless access point (WAP) 138 that may be used to couple one or more of analyte sensor system 8, the plurality display devices, server system 134, and medical device 136 to one another. For example, WAP 138 may provide Wi-Fi and/or cellular connectivity within system 100. Near Field Communication (NFC) may also be used among devices of system 100. Server system 134 may be used to collect analyte data from analyte sensor system 8 and/or the plurality of display devices, for example, to perform analytics thereon, generate universal or individualized models for glucose levels and profiles, and so on.

Figure 3A:
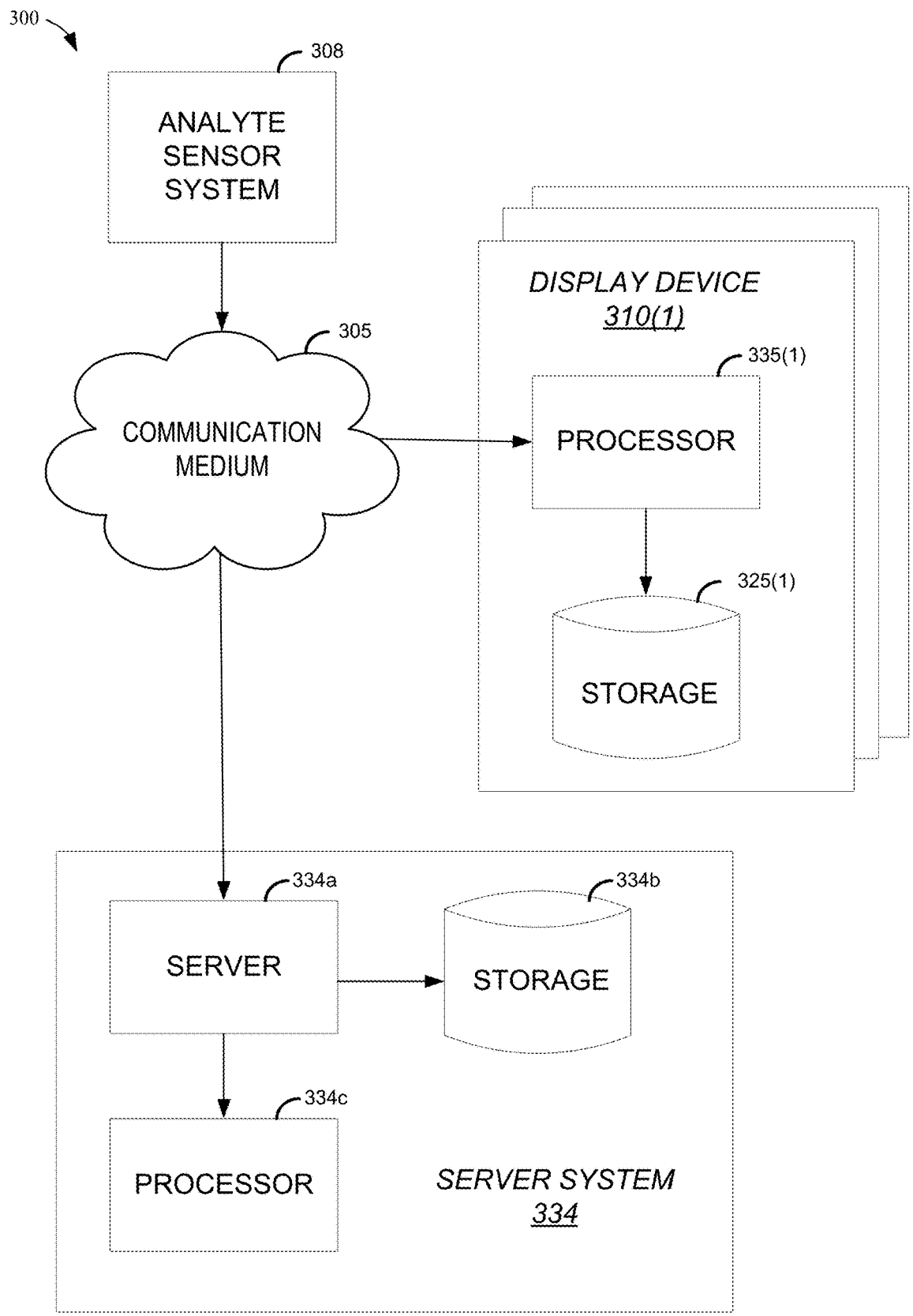
FIG. 3A illustrates aspects of an example system that may be used in connection with implementing embodiments of the disclosure.

Referring now to FIG. 3A, system 300 is depicted. System 300 may be used in connection with implementing embodiments of the disclosed systems, methods, and devices. System 300 may include components which make up the continuous analyte monitoring system, presented herein (e.g., continuous analyte monitoring system 302 described below with respect to FIG. 3B). By way of example, the various below-described components of FIG. 3A may be used to provide wireless communication of glucose data, for example between an analyte sensor system and a plurality of display devices, medical devices, servers and so on, such as those shown in FIG. 1A. In particular, the continuous analyte monitoring system configured to automatically self-diagnose and resolve performance problems detected and associated with the continuous analyte monitoring system, as presented herein, may, at least, comprise the analyte sensor system in communication with at least one display device 310. In some embodiments, as shown in FIG. 3A, the continuous analyte monitoring system 302 (including the analyte sensor system 308 and at least one display device 310) may be in communication with a server system 334.

As shown in FIG. 3A, system 300 may include analyte sensor system 308 and one or more display devices 310(1) . . . (n) (individually referred to as display device 310 and collectively referred to as display devices 310), which in turn include processors 335(1) . . . (n) (individually referred to as processor 335 and collectively referred to as processors 335) and storages 325(1) . . . (n) (individually referred to as storage 325 and collectively referred to as storages 325) (described in more detail with respect to FIG. 3B). Additionally, in the illustrated embodiment, system 300 includes server system 334, which in turn includes server 334*a* coupled to processor 334*c* and storage 334*b*. Analyte sensor system 308 may be coupled to display devices 310 and/or server system 334 via communication medium 305.

As will be described in detail herein, analyte sensor system 308 and display devices 310 may exchange messaging via communication medium 305, and communication medium 305 may also be used to deliver analyte data to display devices 310 and/or server system 334. As alluded to above, display devices 310 may include a variety of electronic computing devices, such as, for example, a smartphone, tablet, laptop, wearable device, etc. Display devices 310 may also include analyte display device 110 and medical device 136. Here, it will be noted that a graphical user interface (GUI) of display device 310 may perform such functions as accepting user input and displaying menus as well as information derived from analyte data. The GUI may be provided by various operating systems known in the art, such as, for example, iOS, Android, Windows Mobile, Windows, Mac OS, Chrome OS, Linux, Unix, a gaming platform OS (e.g., Xbox, PlayStation, Wii), etc. In various embodiments, communication medium 305 may be based on one or more wireless communication protocols such as Bluetooth, Bluetooth Low Energy (BLE), ZigBee, Wi-Fi, 802.11 protocols, Infrared (IR), Radio Frequency (RF), 2G, 3G, 4G, etc., and/or wired protocols and media.

In various embodiments, the elements of system 300 may be used to perform various processes described herein and/or may be used to execute various operations described herein with regard to one or more disclosed systems and methods. Upon studying the present disclosure, one of skill in the art will appreciate that system 300 may include multiple analyte sensor systems, display devices 310, communication media 305, and/or server systems 334.

As mentioned, communication medium 305 may be used to connect or communicatively couple analyte sensor system 308, display devices 310, and/or server system 334 to one another or to a network, and communication medium 305 may be implemented in a variety of forms. For example, communication medium 305 may include an Internet connection, such as a local area network (LAN), a wide area network (WAN), a fiber optic network, internet over power lines, a hard-wired connection (e.g., a bus), and the like, or any other kind of network connection. Communication medium 305 may be implemented using any combination of routers, cables, modems, switches, fiber optics, wires, radio (e.g., microwave/RF links), and the like. Further, communication medium 305 may be implemented using various wireless standards, such as Bluetooth®, BLE, Wi-Fi, 3GPP standards (e.g., 2G GSM/GPRS/EDGE, 3G UMTS/CDMA2000, or 4G LTE/LTE-U), etc. Upon reading the present disclosure, one of skill in the art will recognize other ways to implement communication medium 305 for communications purposes.

Each of the display device 310 and server system 334 may receive, collect, or monitor information, including analyte data and related information, from analyte sensor system 308, such as input responsive to the analyte data or input received in connection with an analyte monitoring application running on analyte sensor system 308. In such cases, display device 310 and server system 334 may be configured to receive such information via communication medium 305.

In certain embodiments, server system 334 may also receive, collect, or monitor the information mentioned above by communicating with display devices 310. In such cases, server 334*a* may be configured to receive such information from display devices 310 via communication medium 305.

This information may be stored in storage 325 and storage 334*b*, respectively for display device 310 and server system 334, and may be processed by processor 335 and processor 334*c*, respectively for display device 310 and server 334*a*. For example, using processor 334*c*, server system 334 may implement an analytics engine capable of performing analytics on information that server 334*a* has collected, received, etc. via communication medium 305. In some embodiments, server 334*a*, storage 334*b*, and/or processor 334*c* may be implemented as a distributed computing network, such as a Hadoop® network, or as a relational database or the like.

Server 334*a* may include, for example, an Internet server, a router, a desktop or laptop computer, a smartphone, a tablet, a processor, a module, or the like, and may be implemented in various forms, including, for example, an integrated circuit or collection thereof, a printed circuit board or collection thereof, or in a discrete housing/package/rack or multiple of the same. In some embodiments, server 334*a* at least partially directs communications made over communication medium 305. Such communications include the delivery and/or messaging (e.g., advertisement, command, or other messaging) and analyte data. For example, server 334*a* may process and exchange messages between analyte sensor system 308 and display devices 310 related to frequency bands, timing of transmissions, security, alarms, and so on. Server 334*a* may update information stored on analyte sensor system 308 and/or display devices 310, for example, by delivering applications thereto. Server 334a may send/receive information to/from analyte sensor system 308 and/or display devices 310 in real time or sporadically. Further, server 334a may implement cloud computing capabilities for analyte sensor system 308 and/or display devices 310.

Figure 3B:
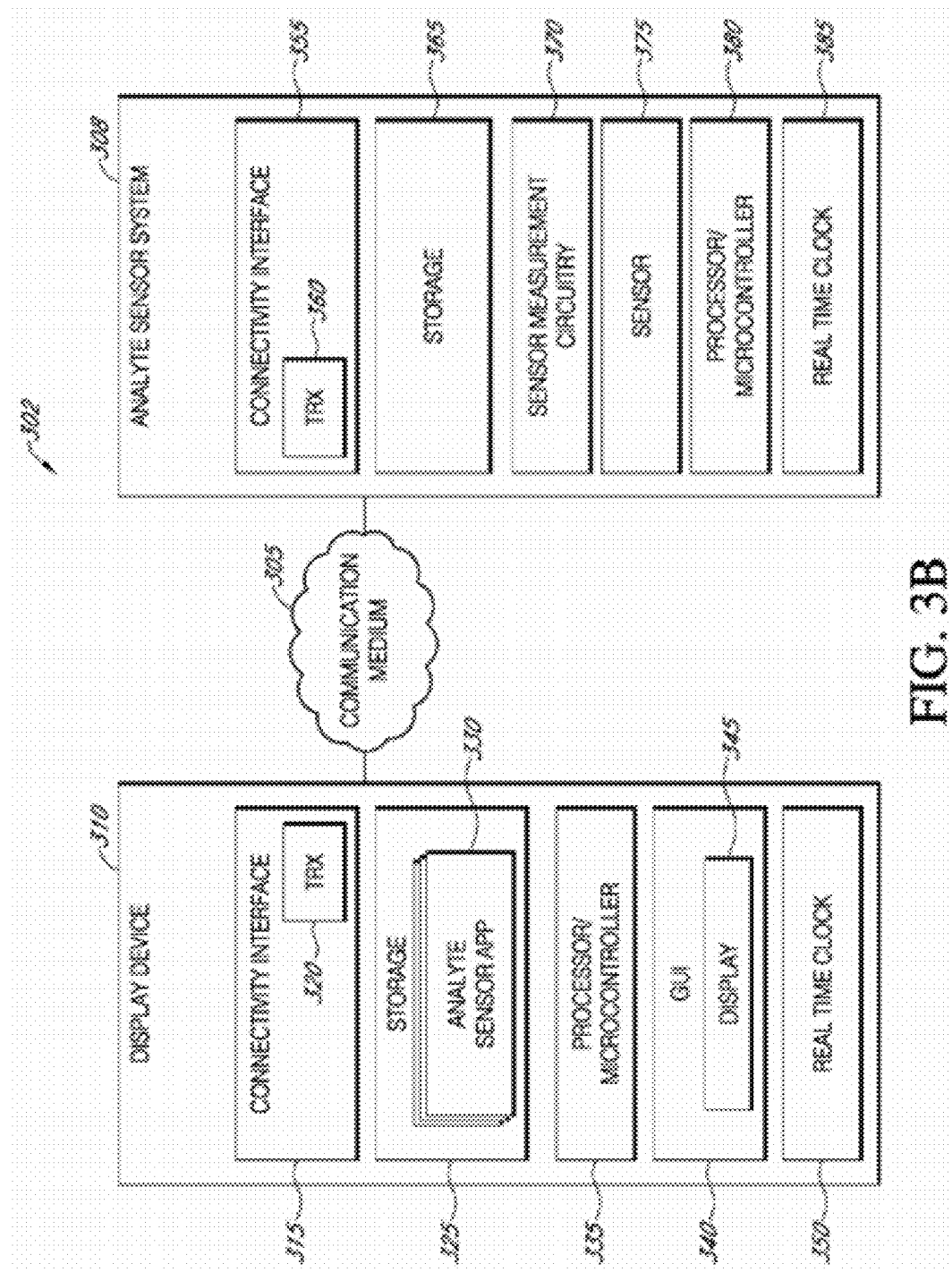
FIG. 3B illustrates aspects of an example system that may be used in connection with implementing embodiments of the disclosure.

FIG. 3B depicts system 302, which includes examples of aspects of the present disclosure that may make up the continuous analyte monitoring system, described herein. As illustrated, system 302 may include analyte sensor system 308. As shown, analyte sensor system 308 may include analyte sensor 375 (e.g., which may also be designated with the numeral 10 in FIG. 1A) coupled to sensor measurement circuitry 370 for processing and managing sensor data. Sensor measurement circuitry 370 may be coupled to processor/microprocessor 380 (e.g., which may be part of item 12 in FIG. 1A). In some embodiments, processor 380 may perform part or all of the functions of the sensor measurement circuitry 370 for obtaining and processing sensor measurement values from sensor 375. Processor 380 may be further coupled to a radio unit or transceiver 320 (e.g., which may be part of item 12 in FIG. 1A) for sending sensor data and receiving requests and commands from an external device, such as display device 310, which may be used to display or otherwise provide the sensor data (or analyte data) to a user. As used herein, the terms "radio unit" and "transceiver" are used interchangeably and generally refer to a device that can wirelessly transmit and receive data. Analyte sensor system 308 may further include storage 365 (e.g., which may be part of item 12 in FIG. 1A) and real time clock (RTC) 380 (e.g., which may be part of item 12 in FIG. 1A) for storing and tracking sensor data.

As alluded to above, wireless communication protocols may be used to transmit and receive data between analyte sensor system 308 and the display device 310 via communication medium 305. Such wireless protocols may be designed for use in a wireless network that is optimized for periodic and small data transmissions (that may be transmitted at low rates if necessary) to and from multiple devices in a close range (e.g., a personal area network (PAN)). For example, one such protocol may be optimized for periodic data transfers where transceivers may be configured to transmit data for short intervals and then enter low power modes for long intervals. The protocol may have low overhead requirements both for normal data transmissions and for initially setting up communication channels (e.g., by reducing overhead) to reduce power consumption. In some embodiments, burst broadcasting schemes (e.g., one way communication) may be used. This may eliminate overhead required for acknowledgement signals and allow for periodic transmissions that consume little power.

The protocols may further be configured to establish communication channels with multiple devices while implementing interference avoidance schemes. In some embodiments, the protocol may make use of adaptive isochronous network topologies that define various time slots and frequency bands for communication with several devices. The protocol may thus modify transmission windows and frequencies in response to interference and to support communication with multiple devices. Accordingly, the wireless protocol may use time and frequency division multiplexing (TDMA) based schemes. The wireless protocol may also employ direct sequence spread spectrum (DSSS) and frequency-hopping spread spectrum schemes. Various network topologies may be used to support short-distance and/or low-power wireless communication such as peer-to-peer, start, tree, or mesh network topologies such as Wi-Fi, Bluetooth and Bluetooth Low Energy (BLE). The wireless protocol may operate in various frequency bands such as an open ISM band such as 2.4 GHz. Furthermore, to reduce power usage, the wireless protocol may adaptively configure data rates according to power consumption.

With further reference to FIG. 3B, system 302 may include display device 310 communicatively coupled to analyte sensor system 308 via communication medium 305. In the illustrated embodiment, display device 310 includes connectivity interface 315 (which in turn includes transceiver 320), storage 325 (which in turn stores analyte sensor application 330 and/or additional applications), processor/microprocessor 335 (also referred to herein as microcontroller 335), GUI 340 that may be presented using display 345 of display device 310, and real time clock (RTC) 350. A bus (not shown here) may be used to interconnect the various elements of display device 310 and transfer data between these elements.

Display device 310 may be used for alerting and providing sensor information or analyte data (and associated commands and messages) to a user, and may include a processor/microprocessor 335 (as previously shown with respect to FIG. 3B) for processing and managing sensor data.

In some aspects, described in detail below, processor/microprocessor 335 may be configured to receive a plurality of event indications, transmitted by the analyte sensor system 308 via transceiver 360 (interchangeably referred to herein as the transmitter of the continuous analyte monitoring system), indicating one or more errors associated with the continuous analyte monitoring system 308, perform root cause analysis, and take one or more actions to resolve one or more determined root causes corresponding to the communicated event indications. Event indications transmitted by the analyte sensor system 308 via transceiver 360 may indicate one or more errors associated with analyte sensor system 308. The root cause analysis performed by processor/microprocessor 335 may ascertain whether the one or more errors associated with the analyte sensor 308 are attributable to a prematurely failing or failed component of analyte sensor system 308. Alternatively, the root cause analysis performed by processor/microprocessor 335 may ascertain whether the event indication is a false positive premature failure or failure detection of a component within analyte sensor system 308 and further determine a root cause of the false positive indication.

In some aspects, described in detail below, processor/microprocessor 335 may, itself, be configured to generate a plurality of event indications indicating one or more errors associated with the continuous analyte monitoring system, perform root cause analysis, and take one or more actions to resolve one or more determined root causes corresponding to the generated event indications. Event indications generated by processor/microprocessor 335 may indicate one or more errors associated with transceiver 360, an application 330 executed by processor/microprocessor 335, one or more other connected devices (such as server system 334 illustrated in FIG. 3A), or one or more applications executing on the one or more other connected devices. The root cause analysis performed by processor/microprocessor 335 may ascertain one or more root causes associated with the event indications generated by the processor. In some cases, the root cause analysis may determine that the one or more errors associated with the transceiver 360 are attributable to a prematurely failing or failed transceiver of analyte sensor system 308. Alternatively, the root cause analysis performed by processor/microprocessor 335 may ascertain the event indication is a false positive premature failure or failure detection of transceiver 360 and further determine a root cause of the false positive indication.

Display device 310 may include display 345, storage 325 (as previously shown with respect to FIG. 3A), analyte sensor application 330, and real time clock 350 for displaying, storing, and tracking sensor data. Display device 310 may further include a radio unit or transceiver 320 coupled to other elements of display device 310 via connectivity interface 315 and/or a bus. Transceiver 320 may be used for receiving sensor data and for sending requests, instructions, and/or data to analyte sensor system 308. Transceiver 320 may further employ a communication protocol. Storage 325 may also be used for storing an operating system for display device 310 and/or a custom (e.g., proprietary) application designed for wireless data communication between a transceiver and display device 310. Storage 325 may be a single memory device or multiple memory devices and may be a volatile or non-volatile memory for storing data and/or instructions for software programs and applications. The instructions may be executed by processor 335 to control and manage transceiver 320.

In some embodiments, when a standardized communication protocol is used, commercially available transceiver circuits may be utilized that incorporate processing circuitry to handle low level data communication functions such as the management of data encoding, transmission frequencies, handshake protocols, and the like. In these embodiments, processor 335, 380 does not need to manage these activities, but rather provides desired data values for transmission, and manages high level functions such as power up or down, set a rate at which messages are transmitted, and the like. Instructions and data values for performing these high level functions can be provided to the transceiver circuits via a data bus and transfer protocol established by the manufacturer of the transceiver 320, 360.

Components of analyte sensor system 308 may require replacement periodically. For example, analyte sensor system 308 may include an implantable sensor 375 that may be attached to a sensor electronics module (e.g., such as sensor electronics module 12 shown in FIGS. 1A, 2A, and 2B) that includes sensor measurement circuitry 370, processor 380, storage 365, and transceiver 360, and a battery (not shown). Sensor 375 may require periodic replacement (e.g., every 7 to 30 days). The sensor electronics module may be configured to be powered and active for much longer than sensor 375 (e.g., for three to six months or more) until the battery needs replacement. Replacing these components may be difficult and require the assistance of trained personnel. Reducing the need to replace such components, particularly the battery, significantly improves the convenience and cost of using analyte sensor system 308, including to the user. In some embodiments, when a sensor electronic module is used for the first time (or reactivated once a battery has been replaced in some cases), it may be connected to sensor 375 and a sensor session may be established. As will be further described below, there may be a process for initially establishing communication between display device 310 and the sensor electronics module when the module is first used or re-activated (e.g., the battery is replaced). Once display device 310 and sensor electronics module have established communication, display device 310 and the sensor electronics module may periodically and/or continuously be in communication over the life of several sensors 375 until, for example, the battery needs to be replaced. Each time sensor 375 is replaced, a new sensor session may be established. The new sensor session may be initiated through a process completed using display device 310 and the process may be triggered by notifications of a new sensor via the communication between the sensor electronics module and display device 310 that may be persistent across sensor sessions.

As described above with reference to FIGS. 1A, 2A, and 2B, sensor 375 may provide an electrical sensor current, typically in the form of raw data signals, indicative of the concentration of an analyte in a patient to a sensor electronics module. This electrical sensor current may then be gathered by transceiver 360 (e.g., an embedded transceiver in the sensor electronics module of analyte sensor system 308) for transmission to display device 310. Prior to transmission to display device 310, transceiver 360 may convert the electrical sensor current into a calibrated and/or filtered data stream that is used to provide a useful value of analyte to a user. For example, transceiver 360 may determine estimated glucose values (EGV data) prior to transmission to display device 310. Data points regarding analyte values may be gathered and transmitted over the life of sensor 375 (e.g., in the range of 1 to 30 days or more). New measurements may be transmitted often enough to adequately monitor glucose levels.

In some cases, in addition to generating analyte values based on the electrical sensor current, transceiver 360 may be configured to generate a plurality of event indications based on the electrical sensor current (interchangeably referred to herein as sensed signals). As mentioned previously, event indications generated by transceiver 360 may indicate one or more errors associated with sensor 375 of analyte sensor system 308. For example, transceiver 360 may be configured to interpret very high (or very low) sensed signals as issues associated with analyte sensor system 308. Accordingly, transceiver 360 may generate a plurality of event indications and transmit these event indications to display device 310 (specifically processor/microprocessor 335 of display device 310), in addition to the analyte values. Display device 310 may use these event indications to perform a root cause analysis to ascertain a root cause for the very high (or very low) sensed signals such that corrective (and/or preventive) action may be taken. In this case, transceiver 360 may be referred to as a "smart transceiver" given its ability to perform additional processing (e.g., the generation of event indications associated with the sensed signals) prior to transmission.

In some other cases, transceiver 360 may be referred to as a "dummy transceiver", wherein transceiver 360 is configured to only transmit analyte values to display device 310 without additional processing, e.g., without generating event indications associated with the sensed signals prior to transmission. Accordingly, only processor/microprocessor 335, as opposed to both transceiver 360 and processor/microprocessor 335, may be configured to generate event indications indicating one or more errors associated with the continuous analyte monitoring system.

Rather than having the transmission and receiving circuitry of each of analyte sensor system 308 and display device 310 continuously communicating, analyte sensor system 308 and display device 310 may regularly and/or periodically establish a communication channel between them. Thus, analyte sensor system 308 can in some cases communicate via wireless transmission with display device 310 (e.g., a hand-held computing device, medical device, or proprietary device) at predetermined time intervals. The duration of the predetermined time interval can be selected to be long enough so that analyte sensor system 308 does not consume too much power by transmitting data more frequently than needed, yet frequent enough to provide substantially real time sensor information (e.g., measured glucose values or analyte data) to display device 310 for output (e.g., via display 345) to a user. While the predetermined time interval is every five minutes in some embodiments, it is appreciated that this time interval can be varied to be any desired length of time.

With continued reference to FIG. 3B, as shown, connectivity interface 315 interfaces display device 310 to communication medium 305, such that display device 310 may be communicatively coupled to analyte sensor system 308 via communication medium 305. Transceiver 320 of connectivity interface 315 may include multiple transceiver modules operable on different wireless standards. Transceiver 320 may be used to receive analyte data and associated commands and messages (e.g., event indications generated by analyte sensor system 308) from analyte sensor system 308. Additionally, connectivity interface 315 may in some cases include additional components for controlling radio and/or wired connections, such as baseband and/or Ethernet modems, audio/video codecs, and so on.

Storage 325 may include volatile memory (e.g., RAM) and/or non-volatile memory (e.g., flash storage), may include any of EPROM, EEPROM, cache, or may include some combination/variation thereof. In various embodiments, storage 325 may store user input data and/or other data collected by display device 310 (e.g., input from other users gathered via analyte sensor application 330). Storage 325 may also be used to store volumes of analyte data received from analyte sensor system 308 for later retrieval and use, e.g., for determining trends and triggering alerts. Additionally, storage 325 may store analyte sensor application 330 that, when executed using processor 335, for example, receives input (e.g., by a conventional hard/soft key or a touch screen, voice detection, or other input mechanism), and allows a user to interact with the analyte data and related content via GUI 340, as will be described in further detail herein.

In various embodiments, a user may interact with analyte sensor application 330 via GUI 340, which may be provided by display 345 of display device 310. By way of example, display 345 may be a touchscreen display that accepts various hand gestures as inputs. Application 330 may process and/or present analyte-related data received by display device 310, according to various operations described herein, and present such data via display 345. Additionally, application 330 may be used to obtain, access, display, control, and/or interface with analyte data and related messaging and processes associated with analyte sensor system 308, as is described in further detail herein.

Application 330 may be downloaded, installed, and initially configured/setup on display device 310. For example, display device 310 may obtain application 330 from server system 334, or from another source accessed via a communication medium (e.g., communication medium 305), such as an application store or the like. Following installation and setup, application 330 may be used to access and/or interface with analyte data (e.g., whether stored on server system 334, locally from storage 325, or from analyte sensor system 308). By way of illustration, application 330 may present a menu that includes various controls or commands that may be executed in connection with the operating of analyte sensor system 308 and one or more display devices 310. Application 330 may also be used to interface with or control other display devices 310, for example, to deliver or make available thereto analyte data, including for example by receiving/sending analyte data directly to the other display device 310 and/or by sending an instruction for analyte sensor system 308 and the other display device 310 to be connected, etc., as will be described herein. In some implementations, application 330 may interact with other application(s) of the display device to retrieve or provide relevant data, e.g., such as other health data.

Analyte sensor application 330 may include various code/functional modules, such as, for example, a display module, a menu module, a list module, and so on as will become clear in light of the description of various functionalities herein (e.g., in connection with disclosed methods). These modules may be implemented separately or in combination. Each module may include computer-readable media and have computer-executable code stored thereon, such that the code may be operatively coupled to and/or executed by processor 335 (which, e.g., may include a circuitry for such execution) to perform specific functions (e.g., as described herein with regard to various operations and flow charts etc.) with respect to interfacing with analyte data and performing tasks related thereto. As will be further described below, a display module may present (e.g., via display 345) various screens to a user, with the screens containing graphical representations of information provided by application 330. In further embodiments, application 330 may be used to display to the user an environment for viewing and interacting with various display devices that may be connectable to analyte sensor system 308, as well as with analyte sensor system 308 itself. Sensor application 330 may include a native application modified with a software design kit (e.g., depending on the operating system) in order to carry out the functionalities/features described herein.

Referring again to FIG. 3B, display device 310 also includes processor 335. Processor 335 may include processor sub-modules, including, by way of example, an applications processor that interfaces with and/or controls other elements of display device 310 (e.g., connectivity interface 315, application 330, GUI 340, display 345, RTC 350, etc.). Processor 335 may include a controller and/or microcontroller that provides various controls (e.g., interfaces with buttons and switches) related to device management, such as, for example, lists of available or previously paired devices, information related to measurement values, information related to network conditions (e.g., link quality and the like), information related to the timing, type, and/or structure of messaging exchanged between analyte sensor system 308 and display device 310, and so on. Additionally, the controller may include various controls related to the gathering of user input, such as, for example, a user's finger print (e.g., to authorize the user's access to data or to be used for authorization/encryption of data, including analyte data), as well as analyte data.

Processor 335 may include circuitry such as logic circuits, memory, a battery and power circuitry, and other circuitry drivers for periphery components and audio components. Processor 335 and any sub-processors thereof may include logic circuits for receiving, processing (e.g., for performing root cause analysis, as described herein), and/or storing data received and/or input to display device 310, and data to be transmitted or delivered by display device 310. Processor 335 may be coupled by a bus to display 345 as well as connectivity interface 315 and storage 325 (including application 330). Hence, processor 335 may receive and process electrical signals generated by these respective elements and thus perform various functions. By way of example, processor 335 may access stored content from storage 325 at the direction of application 330, and process the stored content for display and/or output by display 345. Additionally, processor 335 may process the stored content for transmission via connectivity interface 315 and communication medium 305 to other display devices 310, analyte sensor system 308, or server system 334. Display device 310 may include other peripheral components not shown in detail in FIG. 3B.

In further embodiments, processor 335 may further obtain, detect, calculate, and/or store data input by a user via display 345 or GUI 340, or data received from analyte sensor system 308 (e.g., analyte sensor data or related messaging, such as event indications generated by analyte sensor system 308), over a period of time. Processor 335 may use this input to gauge the user's physical and/or mental response to the data and/or other factors (e.g., time of day, location, etc.). In various embodiments, the user's response or other factors may indicate preferences with respect to the use of certain display devices 310 under certain conditions, and/or the use of certain connection/transmission schemes under various conditions, as will be described in further detail herein.

In some aspects where a "dummy" transceiver 360 is used, e.g., where transceiver 360 is configured to only transmit analyte values to display device 310 without additional processing, processor 335 may be further configured to generate a plurality of event indications based on analyte values transmitted to display device 310 by transceiver 360. In particular, event indications generated by processor 335, based on analyte values transmitted to display device 310 by transceiver 360, may indicate one or more errors associated with the analyte sensor system 308.

In further embodiments, processor 335 may be further configured to generate a plurality of event indications indicative of one or more errors associated with transceiver 360, application 330 configured/setup on display device 310 (and executed by processor 335), one or more devices connected to display device 310, and/or application(s) executing on the one or more other connected devices. For example, when transceiver 360 loses connection and is unable to communicate with (or transmit data to) display device 310, an error may exist with respect to transceiver 360. In such a case, processor 335 may generate an event indication indicative of the error associated with transceiver 360 and determine one or more root causes associated with the event indication. Similar steps may be taken for errors associated with application 330, other connected devices, and applications executing on the other connected devices.

It should be noted at this juncture that like-named elements as between display device 310 and analyte sensor system 308 may include similar features, structures, and/or capabilities. Therefore, with respect to such elements, the description of display device 310 above may in some cases be applied to analyte sensor system 308.

Technical Support

Continuous analyte monitors have been increasing in popularity as both a convenient and necessary way to monitor and always be aware of a user's analyte levels. As a result, the user base utilizing the above-described analyte monitoring system continues to expand, as has the volume of calls to a patient support hotline, accordingly. A typical call to a patient support center entails several aspects. For example, a tech support technician typically spends 10-45 minutes on the phone diagnosing and resolving an issue for which a patient has placed a patient support call. For example, to adequately determine a root cause of the issue being reported, the tech support technician may spend the 10-45 minutes asking a multitude of questions related to components of and/or associated with a patient's continuous analyte monitoring system (e.g., questions related to an analyte sensor, the application, etc.), the patient's recent activities, the patient's deployment routine related to an analyte sensor of the continuous analyte monitoring system, patch site information, the patient's nutrition, etc. In some cases, even with extensive questioning, the tech support technician may not be able to ascertain an accurate root cause, or in some cases, a root cause altogether. Specifically, inaccurately reported information, information the patient (or user) is unable to recall, or information the patient (or user) does not have, may lead to insufficient resolutions provided to a patient (or user) by the tech support technician.

In addition to aiding a caller with a reported issue, in the context of a medical device, patient support calls trigger several behind the scene obligations unique to such environment, which differ from a typical support call in the context of consumer goods not regulated by a regulatory body, such as the U.S. Food and Drug Administration (FDA). The regulatory context, within which a medical device provider operates, may create an obligation on the provider to record or report calls made to its patient support center related to the medical devices sold by the provider. In such context, the conventional technical support staff, in addition to resolving patient issues, may have to spend considerable amount of time complying with or fulfilling the medical device provider's regulatory obligations. Additionally, several departments within a medical device provider organization may wish to interface with the technical support center to identify trending issues in existing products, or to determine patients' desired features or in general needed improvements in the devices of the medical device provider. Consequently, the need for quality assurance, product tracking or general improvements creates a separate reporting obligation for the staff of a patient support center.

With increases in patient base, the conventional methods of handling patient reported issues or questions become impractical or difficult to implement. The disclosed systems and methods herein provide a continuous analyte monitoring system configured to automatically self-diagnose and resolve performance problems detected and associated with the continuous analyte monitoring system by using root cause analysis which provides a systematic process for finding and identifying the root causes of problems related to a patient's continuous analyte monitoring system. According to aspects described herein, root cause analysis aims to both solve problems associated with a patient's continuous analyte monitoring system and prevent similar problems from occurring in the future. In addition, the disclosed systems and methods provide associated logging, recording and regulatory compliance as may be appropriate for a medical device provider.

Example Embodiments of Technical Support Systems/Methods

The embodiments described herein can comprise situations when the described systems or methods proactively, or as a result of an initiating request for tech support from a patient, automatically or semi-automatically identify, resolve technical issues, provide one or more appropriate notifications to affected patients, patients' remote monitors or third parties and record the tech support issues, resolutions and associated data in appropriate databases, including regulatory compliance databases.

Figure 4:
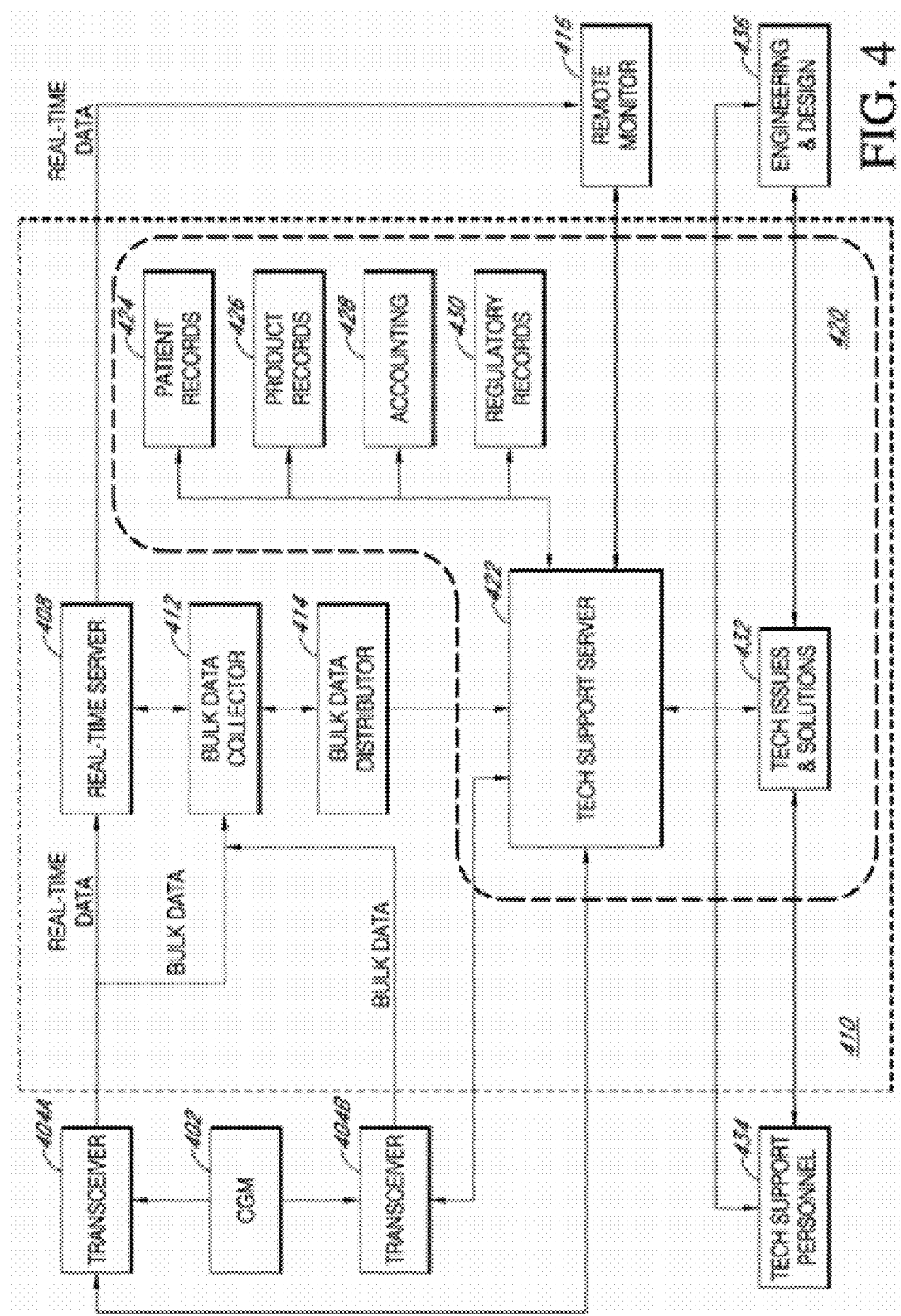
FIG. 4 illustrates an example architecture of an automated or semi-automated technical support system in accordance with embodiments of the present technology.

FIG. 4 illustrates an example architecture of an automated or semi-automated technical support system in accordance with embodiments of the present technology. A continuous analyte sensor 402, such as a continuous glucose sensor referred to as CGM 402, for example, can be inserted in a patient (e.g., transcutaneously) to sense and transmit medical data (e.g., glucose analyte data) of a patient to one or more transceivers 404a and 404b. As described above, the transceivers 404a and 404b can be custom analyte monitoring display devices or computing devices such as smart phones, tablets, smart glasses, smart watches, desktop computers or a combination of these or similar devices. In the disclosure herein, the terms "transceiver" and "receiver" may be used interchangeably to refer to components similar to the transceivers 404a and 404b. Examples of the CGM 402 can include analyte sensor system 8, and examples of transceivers 404a and 404 can include the sensor electronics module 12 of analyte sensor system 8 or any of the display devices 110, 120, 130 and 140 as shown in FIG. 1A, and/or the like. The CGM 402 may produce multiple streams of data and selectively route the data streams to the transceivers 404a and 404b. In the example shown in FIG. 4, the CGM 402 can produce real time data. Real time data can include one or more of estimated glucose value(s) (EGV), glucose concentration rate of change information, CGM alert information, raw sensor data, and/or other type of public or private data. Real time data is separated from bulk data because action may need to be taken based on the real time data in an immediate or timely manner.

Generally, public data includes information that is presented to a patient in charts or reports such as glucose values, monitor/calibration values, time adjustments, event entries by a patient (like meals, carbs, exercise, etc.), when sensors were started/stopped, which transmitter was used and when, and the like. While private data generally comprises information about the system and devices that comprise the system such as battery levels, screen durations, error logs, raw sensor signals, proprietary algorithm input/output, stack dumps of memory, and the like.

Public data and private data can comprise one or both of real time data and bulk data. Bulk data can include, for example, data points such as system software version information, diagnostic information, other proprietary data and stored readings such as glucose levels recorded over a time period such as one hour, two hours, etc. While real time data can include, for example, data points such as monitored glucose levels, timestamps associated with monitored values, glucose monitor status, and the like. Generally, real time data is data that is transmitted by the CGM 402 or transceivers 404a, 404b as it is created or shortly thereafter (e.g., intermittently or periodically, such as every one minute, five minutes, 10 minutes, etc.), while bulk data is data that may be stored on the CGM 402 or the transceivers 404a, 404b for a longer period of time than real time data (e.g., one hour) and transmitted less frequently than real time data.

The transceivers 404a and 404b can in turn transmit their respective data to a cloud computing architecture 410. The cloud computing architecture 410 can include a real time server 408 for receiving and processing real time data from the transceiver 404a. The cloud computing architecture 410 can also include a bulk data collector (BDC) 412 for receiving and processing bulk data from the transceivers 404a and 404b. The real time data can be shared with a remote monitor 416 operated by a caregiver user, e.g., affiliated with the patient user. For example, in some cases, a patient's parent or guardian can have access to the remote monitor 416 for the purpose of remotely monitoring the patient's health and receiving system alarms related to patient's health. Examples of systems and methods for remote monitoring of analyte data, such as by remote monitor 416, are described in more detail in U.S. Patent Publication Nos. 2014/0184422 and 2014/0187889, all of which are incorporated herein by reference in their entirety for all purposes.

In some embodiments, the cloud computing architecture 410 includes a tech support server 422. The tech support server 422 can include one or more computers (e.g., servers) in communication with one or more databases to form a tech support system 420 for diagnosing and resolving patients' technical issues associated with a medical device, such as CGM 402 and/or transceiver 404a, 404b, and handling subsequent logging and reporting associated with those technical issues. Various embodiments of the tech support system 420 are described that comprise the tech support server 422 in communications with a patient records server or database 424, product records server or database 426, an accounting server or database 428, a regulatory records server or database 430, and/or a tech issues & solutions server or database 432.

In some embodiments, the cloud computing architecture 410 further includes bulk data distributor (BDD) 414. The BDD 414 can provide a portion of the data in the BDC 412 to the tech support server 422. In some embodiments, the tech support server 422 can be in direct communication with one or more of transceivers 404a and 404b.

In some embodiments of the tech support system 420, the tech support server 422 can communicate with a patient records database 424. In some cases, for example, diagnosing or resolving a patient's complaint involves an investigation or query of the patient's records. Such investigation can reveal information relevant to resolving the patient's technical issue. For example, the investigation can help determine what sensor the patient is currently using, the age of the sensor, or other historical data related to the patient's hardware, software or the patient's prior technical issues. In some instances, the automated or semi-automated systems and methods described herein can automatically order replacement parts, for example replacement sensors, and automatically update the appropriate patient's records in the patient records database 424.

In some embodiments of the tech support system 420, the tech support server 422 can communicate with a product records server 426. Technical issues discovered automatically, or as a result of a patient's communication with the tech support server 422, can contain information relevant to product development, quality assurance and general future improvements of features of the devices of the medical device provider. In some implementations, the tech support server 422 can communicate with the product records server 426 for tracking technical issues associated with the hardware provided by the medical device provider. Such product tracking may help to trace the cause of an issue to a particular batch of products coming from a particular laboratory or manufacturing lot. The tech support server 422 or the product records server 426 can use this information to trigger remedial measures aimed at resolving similar issues before patients have to place a request for service or initiate a tech support ticket. In instances where the described systems and methods proactively resolve an issue, without any initiating action of the patient, a notification can be issued to the affected patients alerting them to the existence of the issue and the subsequent resolution undertaken automatically by the system.

In some embodiments of the tech support system 420, the tech support server 422 can be configured to both store and query a tech issues & solutions database 432. The database 432 can be a knowledge database updated automatically by the tech support server 422 or by the tech support personnel operating a tech support personnel computing system 434. Some references to the tech support personnel computing system 434 may refer to the personnel operating the computing system 434. The tech issues & solutions database 432 can maintain histories and logs of issues the patients have experienced as well as known solutions to those issues. In some embodiments, data or population analytics can be run on the data in the database 432 or alternatively on data provided by the BDD 414. Tech support reports of varying duration (e.g., top 10 or top 5 reported issues since last week, last month, last three months, etc.) can be generated from the data in the tech issues & solutions database 432 to improve the products or services provided. For example, a top ten issues list over the past month can be compiled and presented (e.g., via an automated email) to the medical device provider's engineers. Issues can be ranked based on the time period in which they occurred, their frequency and their severity. The ability to generate system-wide issue reports enables identifying and distinguishing between unimportant or infrequent patient technical issues versus emerging trends in issues that affect many patients and their respective analyte monitoring systems. In some embodiments, issues and errors encountered by the patients may be assigned a numerical key that can facilitate running data analytics and reporting as described above.

For example, by addressing a limited quantity of top-ranked tech support issues using methods and systems in accordance with the present technology (e.g., such as the top 6 issues related to the software application based on user interaction, user education, improved UI/UX, and/or other forms of 'soft' improvements), the call volume to the tech support center (e.g., tech support personnel 434) can be reduced substantially, e.g., such as up to 50% reduction of the example top 6 issues. Also, for example, addressing the top-ranked issues may improve saving flows to the other downstream activities that tech support issues subsequently cause (e.g., such as QA/Regulatory etc., as well as may improve customer retention. Examples of the top-ranked tech support issues can include a question mark icon ("???") presented in the status box (e.g., associated with communication disruptions between transmitter and receiver), inaccurate calibrations, hardware error icons, or others.

Such automated coding of errors can improve the patient's experience when troubleshooting an issue. In some cases, when addressing a technical issue through conventional channels of patient support, patients do not refer to various components of the analyte monitoring system by correct terminology. Consequently, time and resources are spent attempting to identify the technical issue for which a patient is contacting tech support. For example, when discussing a technical issue with tech support technician, a patient may incorrectly state that his sensor does not work, while the issue may be that the patient's receiver does not turn on. Consequently, the technician attempts to resolve the issue by applying sensor failure troubleshooting scripts. In some cases, the technician may incorrectly order replacement sensors for the patient, while the issue may reside in the patient's receiver. In examples where the patient's receiver is a mobile computing device such as smart phone 120 and the like, which has analyte sensor application 330 operating thereon, when the analyte sensor application 330 automatically categorizes and associates an error code to an error message according to the embodiments described herein, it will query various components and status of the medical device and can correctly identify the parts which may be experiencing issues. Consequently, an error ticket can be generated correctly identifying parts that may need troubleshooting.

In some embodiments, the patient can encounter an alert or error message on the transceivers 404*a* and/or 404*b*, e.g., which can be embodied as display devices 110-140 as in FIG. 1A and referred to as display device(s) 404. An error code can be associated with the alert or the error message which the patient is viewing on his display device. In some embodiments, the patient can add information to the error message about the context in which the error message was received and transmit the augmented error message to the tech support server 422. In some embodiments, the display device 404 can augment the error message with additional information that may assist the technical server 422 in resolving the technical issue. Examples of context information the patient can add to the error message can include whether the patient had just engaged in strenuous exercise activity, had taken a meal or administered insulin. Examples of information which can be added by the display device 404 can include the operating system, the hardware and its version, other concurrently running applications (if appropriate patient permissions have been obtained). In some embodiments, appropriate patient permissions related to HIPAA and/or other legal or regulatory privacy issues can be obtained and appended to the error message and subsequently transmitted to the tech support server 422. As described, an error code can be associated with the error message and transmitted along with the necessary permissions and patient contact information to the tech support server 422, as part of an error ticket. The operations associated with building an error ticket can be handled by the analyte sensor application 330 running on the display devices 404.

The error ticket can be transmitted to the tech support system 420 via a wired or wireless communication, for example, via the communication medium 305 as described above. In some embodiments, the tech support server 422 receives the error ticket. The tech support server 422 can include software modules to automatically or semi-automatically record the incident described in the error ticket in one or more relevant databases of the medical device provider. For example, the tech support server can record the incident contained in the error ticket in the relevant patient record in the patient records 424, in product records 426, in regulatory records 430 and/or the tech issues & solutions 432. The tech support server 422 can diagnose the issue associated with the incident reported in the error ticket locally or via communication with the tech support personnel 434. In some embodiments, the tech support server 422 can query the tech issues & solutions database 432 to resolve the issues identified in the error ticket. The tech support server 422 can take remedial measures automatically or semi automatically in response to the incident reported in the error ticket. For example, the tech support server 422 can initiate ordering a sensor replacement as will be described further below. In some embodiments, the tech support server 422 can send over-the-air (OTA) software updates to the display devices 404 to resolve the issues identified in the error ticket.

In some embodiments, the tech support server 422 can communicate with various databases of a medical device provider within or without the tech support system 420 for various purposes. For example, upon identification and resolution of an issue, the tech support server 422 can further update one or more databases of the medical device provider, for example, patient records 424, product records 426, accounting 428, tech issues & solutions 432, and/or regulatory records 430.

The read or write operations into and out of the various databases of the medical device provider as described herein are meant as examples. Persons of ordinary skill in the art can readily envision a multitude of read and write operations between various databases of the medical device provider for the purposes of diagnosing and resolving patient technical issues, while providing proper record keeping for regulatory, product, accounting or other purposes associated with tech support.

In some embodiments, before an automated execution of a determined resolution, the tech support system 420, by request, automatically, by decision tree, or randomly, can provide the error ticket information and determined resolution to the tech support personnel 434 for the purposes of error identification, verification of solution, or to provide a check on the automated tech support system, for example based on statistically driven methods.

The identification and resolution of a technical issue may not involve an action of the patient. For example, the analyte sensor application 330 running on the display device 404 can detect data gaps between certain hours of night. The analyte sensor application 330 running on the display device 404 can generate an error ticket with an error code which identifies this issue as "data gaps at night," and append contextual data to the error ticket as described herein. In some embodiments, appropriate patient permissions can be obtained prior to detecting an incident and used when an issue is detected and an error ticket is built. If patient permissions have previously been obtained, the analyte sensor application 330 can append those permissions to the error ticket, or if those permissions are not previously obtained, the analyte sensor application 330 can prompt the user for those permissions, append the obtained permissions to the error ticket and transmit the error ticket to the tech support server 422. The tech support server 422 can extract the error code from the error ticket and search the database of known issues in the tech issues & solutions database 432. The error code may have, for example, identified one or more conflicting applications running in the background of the display devices 404, which causes data gaps at nighttime. A message can be generated by the tech support server 422 and transmitted as an alert to the display devices 404 containing a message alerting the patient about the detection of the issue of data gaps at night and the suggested solution of closing those applications during nighttime.

Some technical issues can be resolved at the application level on the display devices 404, without generating or transmitting an error ticket to the tech support server 422. For example, the monitored analyte values are by design allowed to be outside range for some 10 to 20% of the time during an analyte monitoring session. Some patients may not be aware of such or other system limitations and incorrectly assume that these system limitations amount to technical issues. When there is an attempt to generate an error ticket based on such issues, the analyte sensor application 330 can alert the patient thus alleviating the need to generate or transmit error tickets. In some embodiments, an information button, for example in the form of the uppercase or lowercase letter I (i.e., "i") or other symbol can be displayed along with any alert issued by the analyte sensor application 330. The patient can click on the information button and obtain more information about the displayed alert. For example, an alert indicating "sensor readings cannot be obtained" may be because the system requires more time to process and display sensor readings. When the patient clicks on the information button, a message explaining that "a waiting period is normal before sensor readings can be obtained" may be displayed on the display devices 404. In another example, if an "out of range" symbol is not accompanied by an appropriate text, clicking on the information button can clarify, for example via a text box shown on the display devices 404, that the transceiver may be out of range. In other examples, various timing or durations associated with an alert message or an error message can determine whether or not an error ticket is generated. For example, if an error is detected to have persisted for a duration less than a threshold (e.g., less than an hour), the analyte sensor application 330 may halt generation of an error ticket until that threshold is reached. If the error persists for more than the duration threshold (e.g., an hour), an appropriate error ticket can be generated and transmitted as described herein. The threshold duration can be tied to or based on the underlying alert or error message.

In some embodiments of the tech support system 420, the analyte sensor application 330 can be retrofitted with software modules or algorithms for resolving patient technical issues. For example, analyte sensor application 330 may be configured to receive and/or generate a plurality of event indications indicating one or more errors associated with one or more components of the continuous analyte monitoring system, determine one or more root causes associated with the plurality of event indications, and take one or more actions to resolve the one or more root causes. Processor 335 may be configured to provide technical support irrespective of support from technical support server 422. However, in some aspects, technical support server 422 may inform the root cause analysis performed by processor 335 by providing processor 335 with pattern(s) associated with event indications for a population of patients.

Resolution of some patient technical issues involves intervention by the tech support personnel 434. For example, in some cases, the display device 404 may be retrofitted with an "airplane mode," such that toggling this mode to "on" position, shuts off all wireless communications of the display device 404. The patient may place a phone call to tech support personnel 434 complaining about the display device 404's inability to capture the analyte data wirelessly. The tech support personnel 434 may have to apply several troubleshooting scripts for resolving the issue before realizing that the patient's display device 404 has the airplane mode in the "on" position. In some embodiments, the analyte sensor application, can locally detect that the display device 404 is in an "airplane mode" and issue an appropriate alert to the patient (automatically or as a result of patient's action to initiate a tech support request). Such issues and subsequent resolution may still be reported to the tech support server 422 and recorded and reflected in the tech issues & solutions database 432 or other databases associated with the tech support system 420 for a variety of purposes, for example for product improvement, or better user interface design.

As described herein, the tech issues & solutions database 432 can interface with engineering & design team computing system 436 for the purpose of providing data on appropriate improvements to the products and services of the medical device provider. Some references to engineering & design team computing system 436 may refer to the engineering & design team personnel operating the computing system 436. When the design or engineering personnel have visibility into tech issues, they can take appropriate action. For example, the user interface designers in collaboration with engineers may incorporate a feature in an update to the analyte sensor application 330 where the "on" status of an "airplane mode" is automatically detected and an alert is automatically issued to the patient explaining that obtaining analyte data via wireless connection is suspended until the "airplane mode" is turned off. Consequently, the systems and methods described herein not only provide automatic or semi-automatic resolution of technical issues, but they provide visibility of the ongoing technical issues to appropriate teams within the medical device provider for efficient and proactive resolution of those issues.

In some embodiments of the tech support system 420, the technical issues and resolutions recorded in the tech issues & solutions database 432 may additionally be encoded with an identifier of the tech support personnel 434. In a given technical support environment, the tech support personnel can develop expertise and skills in various areas. Such specialization can make troubleshooting patient's issues more efficient, increasing patient's satisfaction. By mapping the technical issues to the appropriately skilled personnel, the systems and methods described herein can, when needed, route patient calls to the appropriately skilled personnel within the tech support personnel 434 to efficiently achieve resolution of patient's technical issues. Additionally, members of the engineering & design team 436 can more efficiently reach the appropriately skilled tech support personnel 434 when examining tech support issues reports and attempting to improve products or fix issues.

In some embodiments of the tech support system 420, the solutions embedded in the tech issues & solutions database 432 can be assigned a rating score based on how frequently the solution has been helpful to resolving patient's technical issues. The tech support server 422 can routinely and automatically comb through the solutions embedded in the tech issues & solutions database 432 and purge the database from solutions that have routinely been given a low score.

In some embodiments of the tech support system 420, the tech support server 422 may work in conjunction with the tech support personnel 434 in real time. For example, as a tech support personnel 434 troubleshoots a patient's technical issue, the tech support server 422 can search the tech issues & solutions database 432 for other tech support personnel who may have recent experiences with a similar issue. Subsequently, the tech support server 422 can connect the two tech support personnel via an on-screen chat box or other methods to provide for an ability of the tech support personnel 434 to query and use other tech support personnel's knowledge and skill in resolving patients' technical issues.

In some embodiments of the tech support system 420, the tech support server 422 can categorize an issue and consult an appropriate troubleshooting script in the tech issues & solutions database 432. Alternatively, if the tech support server 422 determines that the resolution of the issue is better left to a tech support personnel 434, the tech support server 422 can route the issue to a tech support personnel 434 who is known to be skilled in handling the issue.

In some embodiments of the tech support system 420, the tech issues & solutions database 434 can contain history of issues associated with previous products of the medical device provider. Running data analytics and comparisons between the current products of the medical device provider and known historical trends of previous products can provide insights on whether a particular technical issue should receive more attention.

In some embodiments of the tech support system 420, the tech support server 422 can be configured with appropriate thresholds to automatically alert when the reports from the tech issues & solutions database 432 surpasses those thresholds. In some embodiments, system-wide reports can be run on data which is not subject to HIPAA. The engineering & design team 436 can subsequently indicate whether a particular issue reported to them was acknowledged and have been added to their workload. Consequently, an analysis of the tech issues & solutions database 432 can reveal issues that have not yet been acknowledged or acted upon by the engineering & design team 436. The ability of the engineering & design team 436, to have visibility into the technical issues encountered by the patients, enables the engineering & design team 436 to proactively experiment with various solutions and potentially update the tech issues & solutions database 432 with new solutions for emerging issues.

In some embodiments of the tech support system 420, the tech support server 422 can further communicate with an accounting server 428. In some cases, resolving a patient's technical issue can entail modifications to the medical device provider's one or more accounting databases. For example, the automated methods and systems described herein can determine that a resolution of a patient's technical issue entails ordering of a sensor replacement. The system can therefore order a replacement sensor to be shipped to the patient. The system can subsequently create an invoice for the patient. Alternatively, if the sensor replacement is to be provided free of charge the tech support server 422 in association with the accounting server 428, can record this event in appropriate company accounting databases as a tax-deductible eligible event.

In some embodiments of the tech support system 420, the tech support server 422 can proactively search for and detect technical issues by running population data analytics (e.g., based on multiple patient experiences) on the bulk data contained in the BDC 412 or data provided by the BDD 414. Conventionally, technical issues would have to be reported and logged through regular technical support channels. Months of patients' calls need to be manually analyzed before trends in the emerging or potential issues could be detected. However, by proactively mining the data in the BDC 412 and/or BDD 414, emerging trends and potential issues can be detected and remedied before they can afflict many patients. In some embodiments, remedying detected technical issues include tech support system 420 sending over-the-air (OTA) software fixes to display devices 404.

The real time data stored on the real time server 408 and the bulk data stored on the BDC 412 can be analyzed, separately or together, for the purposes of providing proactive tech support. Such analysis can reveal latent or overt technical issues. In some embodiments of the tech support system 420, the tech support server 422 can compare different streams of data associated with same reading sessions to detect discrepancies indicative of an underlying technical issue. In some embodiments, the data stored on the real time server 408 and the BDC 412 can contain duplicative analyte data associated with same analyte read out sessions. Discrepancies between the streams of data stored in different databases can indicate the existence of a technical issue. In some embodiments, for example, algorithms comparing the data streams stored in the real time server 408 and the BDC 412 can detect discrepancies and determine that the discrepancies indicate a calibration error. The tech support server 422 can generate a message on the display device 404 alerting the patient to recalibrate.

In some embodiments of the tech support system 420, the tech support server 422 can be configured to analyze the data on one or more reading sessions stored on the real time sever 408 or BDC 412 in order to diagnose and resolve an error ticket initiated by the user or the analyte sensor application 330.

Tech Support Via Remote Monitoring

In some embodiments of the tech support system 420, the tech support server 422 can be configured to be in communication with the remote monitor 416. In some instances, the remote monitor 416 may desire to initiate an error ticket. For example, the remote monitor 416 may not receive analyte data and/or alerts, via the real time server 408, associated with the patient user's analyte state monitored by CGM 402 and transceiver 404A, 404B. In such cases, in some implementations, the remote monitor 416 can initiate an error ticket similar to the way a transceiver 404A generates and transmits an error ticket as described herein. The remote monitor 416 can add authentication or verification data in the error ticket to identify itself as a HIPAA authorized user. In case of a loss of reading, the tech support server 422 may recall and execute an appropriate troubleshooting script. For example, the tech support server 422 can query the status of the transceiver 404A to determine whether the transceiver 404A is receiving analyte readings. If, for example, the transceiver 404A transmits a status "out of range" to the tech support server 422, a message explaining this status can be conveyed to the remote monitor 416, alerting the remote monitor that the patient's transceiver is out of range.

In some embodiments, the remote monitor 416 receives real time data from the real time server 408. An error ticket and a request for tech support generated by the remote monitor 416 can include real time data. In some embodiments of the tech support system 420, the tech support server 422 can be configured to analyze real time data contained in an error ticket from a remote monitor 416 in conjunction with the bulk data from the BDD 414 to diagnose and resolve the error ticket using techniques described herein. The tech support server 422 can be in communication with an authentication system to authenticate the remote monitor 416 prior to communicating with the remote monitor 416.

In some embodiments, the remote monitor 416 is presented with real time data in a visual form or graphical display. A remote monitor 416 can detect and initiate an error ticket based on inspection of the visual or graphical display. The tech support system 420 may also have access to same or similar copies of the visual or graphical displays transmitted to the remote monitor 416, and can decode an error ticket generated based on the visual or graphical displays. The tech support system 420 can include visual or graphical display data including, data tables, charts, data categories (e.g., estimated glucose values (EGVs), logs, etc.) with the same or similar visual or graphical display data as provided to the remote monitor 416. In some embodiments, the visual or graphical display data can include charts presenting data in a chronological form. In some embodiments, the visual or graphical display data can include an identification of the source of the data (e.g., hardware or software generating or initiating the visual or graphical display).

In some embodiments, the tech support system 430 may include one or more tools for automatically or semi-automatically downloading relevant data from and analyzing one or multiple returned display devices 404 or returned CGM devices 402. In conventional customer support environments, the cost and administrative burden of properly analyzing a returned unit may be prohibitive. Consequently, product improvements or troubleshooting advantages, which could be gained from analyzing such returned units, may be forfeited. In some embodiments, the tech support system 420, can request that a patient return a custom analyte display device or a CGM 402 for further troubleshooting and analysis. The patient can be provided with shipment material for returning these items. The tech support system 420 can utilize a variety of tools to download and analyze the relevant data embedded on returned devices both for troubleshooting and assisting the patient who returned the items, as well as collecting technical data for a multitude of returned units from multiple patients to identify, alert or resolve issues affecting multiple devices. In some embodiments, the tech support system 420 includes a repository tool for downloading and analyzing analyte data from a custom analyte display device. In some embodiments, the repository tool can support custom analyte display data visualization. When a patient returns a custom analyte display, the repository tool can be used to download the device data and further investigate the device. In some embodiments, the tech support system 420 can include a transmitter download tool. When a patient returns a transmitter for investigation, the transmitter can be downloaded using this tool and the data can be visualized as a data table using a database viewer, for further investigation.

Multiple Copies

In some embodiments, the cloud computing architecture may receive and store multiple copies of the same data stream for various purposes including providing automatic or semi-automatic tech support, issue detection and resolution. As described herein, in some embodiments, the real time server 408 can receive real time data from the display devices 404, more frequently than the BDC 412 receives data from the display devices 404. For example, the real time server 408 can receive real time data from the display device 404a every hour automatically via a wireless connection; the BDC 412 can receive bulk data from the display device 404b when the patient initiates uploading bulk data. A copy of bulk data can be stored in the BDD 414 for a longer time than the same copy stored in the BDC 412. In some embodiments, various storage durations for various copies of the same data stream can be designated and executed to accomplish different objectives, for example, to comply with a mandated "keep data" order within the cloud computing system 410. While not shown, the cloud computing system 410 can include an IT archive server, which can store data for which there is a mandated "keep data" order longer than the storage durations among other components of the cloud computing system 410. As described, multiple copies within the cloud computing system 410 (which may be included for objectives other than providing tech support) can nevertheless be utilized to automatically identify and resolve technical issues. For example, in some embodiments, multiple copies are stored in the IT archive server to comply with quality requirements "keep data" durations. These multiple copies may be recalled, analyzed and compared with other copies of the same data stream in order to identify or resolve technical issues.

Proactive detection, identification and analysis of technical issues (within one patient's devices or within a multitudes of patients' devices) can be accomplished by automatically analyzing the output of the medical device provider's systems and services that may not be specifically directed to providing technical support. In some embodiments of system 300, retrospective reporting may be provided to allow patients and their caregivers to view patient's data and metrics associated with the patient's data. In some embodiments, if the tech support system 420 detects a failure, the patient or patient's caregiver can be provided with questionnaires in addition to retrospective reporting. In some embodiments, the questionnaires may be in the form where answers are collected by receiving inputs and selections via drop down menus, radio buttons or other forms where limited free text is allowed. Collecting data in this form allows for expedient analysis, for example, via running population or data analytics.

In some embodiments, the patient may be presented with general or real time information on the tech support system 420 or the tech support personnel 434. For example, the patient can, by navigating through a menu driven application, be informed as to a current estimate of tech support wait/hold times if the patient were to speak with a tech support technician. Additionally, comparison estimated wait times of automated troubleshooting option can be presented. The wait time estimates can be determined from system-wide historical analysis of tech support data by time of day, week, month, etc. In some embodiments, the wait time estimates can be provided to the patient after the patient has provided information and data associated with her technical issue. The provided wait time estimates can be informed by or adjusted by the technical issue data entered into the system.

In some embodiments, the analyte sensor application 330 or similar application used by the patient can be equipped with a menu option for locating physical stores where devices of a medical device company or replacement parts are sold. In some embodiments, the patient can place an order for medical device products or replacement parts by interacting with the analyte sensor application 330. The physical stores can allow inventory availability checks, receipt of orders, holding of and in-store pick-up of products.

In some embodiments, when automatically processing a patient's request for sensor replacement and before an automatic replacement order is booked, one or more anti-fraud algorithms can be utilized to determine whether the request for sensor replacement is genuine, due to user error or is a result of a real sensor failure.

Tech Support Documentation

Medical device providers, who offer the products and systems described herein may have to contend with laborious documentation following a call to their tech support centers. For example, after a patient places a call to a medical device tech support center, and a tech support technician has resolved the patient's issue, the technician or other personnel may have to document the call by manually entering information associated with the call. Manual entry of the information associated with the call, for example, can include recording the technical issue the patient faced, the troubleshooting script the technician chose, the questions the technician presented to the patient, the patient's responses, information collected regarding the context of the patient's call, the patient's hardware, the patient's software and other relevant data. The tech support personnel generate a report based on the gathered information. The report may be transmitted to other departments within the medical device provider based on various objectives. Those departments may in turn audit the report based on various objectives before formally concluding a documentation process associated with a patient technical support call. For example, quality assurance department may receive and audit the report to determine whether the information gathered in the report is satisfactory for the purpose of improving products or service quality. The documentation process may be concluded after the various departments within the medical device provider have audited and approved the report. In some cases, the report is sent back to the tech support personnel to gather additional data as required by various departments within the medical device provider. Consequently, the documentation obligations associated with a patient's call or email to a tech support center are considerable. The systems and methods described herein can relieve such documentation obligations by automating the gathering of the data, and generation reports or documentation associated with a call to tech support.

In some embodiments, the analyte sensor application 330 can be configured with various tabs presented to the patient when the patient attempts to troubleshoot an issue using the analyte sensor application 330. Clicking the tabs can guide the patient through a decision tree for resolving the technical issue. Clicking on some options or tabs can trigger the analyte sensor application 330 to alert the tech support system 420 to take action regarding the patient's technical issue. The tech support server 422, or if tech support personnel 434 have been engaged, can text or otherwise push messages to the analyte sensor application 330 to be displayed to the patient informing them of the progress of the troubleshooting of their issue.

Remote Control of Medical Device

In some embodiments, the tech support system 420 or the tech support personnel 434, automatically, or in response to a patient's request, can establish remote control of a patient's medical devices (e.g., display devices 404 or CGM 402) in order to provide automated or semi-automated tech support. By establishing one or more remote control events, the tech support system 420 or the tech support personnel 434 can accomplish tasks associated with diagnosis and resolving of patient's technical issues. For example, a remote control event can include status query, self-diagnostic troubleshooting algorithms, reading and writing control data into and out of the patient's medical devices, modifying device parameters and other control events. In some embodiments, a remote control event is transmitted from the tech support server 422 to a patient's medical device, for example to a display device 404. As described earlier, the display device 404 may be a smart phone, smart wearable device or a custom analyte display device. The remote control event can include algorithms, software instructions or scripts for running one or more tests, troubleshooting scripts, diagnostic tools, or similar tech-support-related algorithms to be operated on the patient's medical devices (e.g., the CGM 402 or display devices 404). The remote control event can include an internet transaction, notification, text message or other interactions. In some embodiments, the display device 404 can receive and store the remote control event instructions until such time as specified by the remote control event. The control event may contain algorithms to be operated on the CGM 402, the display 404, both, or other patient's medical devices. In some cases, the remote control event contains software instructions or algorithms to be executed in the event of detection of a present or future event or to be repeated under pre-defined conditions. A trigger event for execution of a control event can include detection of a value of a parameter within the patient's medical devices, or medical device parameters surpassing a threshold range or staying within a thresholds range. In some cases, the remote control event may be executed immediately upon receipt from the tech support system 420 or the tech support personnel 434. In other cases, the remote control event may be programmed to run over a period of one or more cycles (e.g., the cycles can be defined as cycles of interaction period between the CGM 402 and the display devices 404). In some cases, upon execution of a remote control event, the obtained results, values, parameters, and/ or device observations can be transmitted to the tech support system 420 for further analysis or action. The described remote control techniques can be invoked as part of automatic diagnosis and troubleshooting of technical issues in error tickets. Appropriate notifications in the form of visual or audio alerts can accompany the execution and operation of a remote control event.

Example Embodiments of Tech Support Data Flow

In some embodiments of the tech support system 420, the tech support server 422 can further communicate with a regulatory incident record database 430. As described herein, some technical issues discovered by or reported to the medical device provider trigger an obligation of recording the incident in a database, and in some cases, reporting the incident to governmental regulatory bodies, such as the FDA. For this purpose, a regulatory incident record database 430 can be created for storing technical issues and associated data for which a government regulatory recording or reporting obligation exists. The tech support system 420 can automatically update the regulatory incident record database 430.

In some embodiments, when a patient encounters an "error condition encountered," an error flag is transmitted to the receivers 404a and 404b via wired or wireless communication. In some cases, the CGM 402 or its transmitter (e.g. embedded transmitter) can generate a device-triggered error flag. The patient may choose to report further information about the incident or provide other contextual information to be included with the error flag. The receivers 404a and/or 404b can also add additional information to the error flag. As described above, the receivers 404a and/or 404b can communicate with the tech support server 422 via a wired or wireless connection providing the error flag to the tech support server 422.

The tech support server 422 can include software or hardware modules to automatically or semi-automatically: record an incident information embedded in an error flag by accessing and writing into one or more relevant databases; diagnose the issues giving rise to the error flag; and determine an appropriate resolution or response to the error flag.

For example, in some embodiments, automatic diagnosis and resolution of the errors giving rise to the error flag can include matching an error code embedded in the error flag against a database of previously known issues and their associated known resolutions. For example in some cases, the error flag can contain an error code as well as information about the receiver registering the error code which make evident the condition for a known error where an app running in the background of the receiver device causes issues with the app handling the operations of the CGM 402. A known resolution can be identified by suggesting a swipe/kill the conflicting app. In other cases, the error code embedded in the error flag can be linked to a bad sensor. Subsequently, ordering a replacement sensor can be identified as the resolution of the issue.

Semi-Automatic Diagnosis/Resolution

In some embodiments, the tech support server 422 may do preprocessing and analysis on the error ticket before subsequently sending the error ticket information and any analysis to technical support personnel 434. In some embodiments, if the tech support server 422 cannot resolve the patient's technical issue automatically, it may forward the error ticket to tech support personnel 434 along with preprocessing and analysis to assist them in determining the cause and resolution of a patient's technical issue. The tech support server 422 can utilize machine learning, decision control logic or other techniques to determine if the diagnosis and resolution of an issue is better delegated to a tech support personnel 434. In some embodiments, the tech personnel 434 can partially handle identification and resolution of a patient's technical issue and hand off some operations to the tech support system 420.

HIPAA Compliance

While FIG. 4 shows the tech support server 422 as a separate server than the BDD 414, in other embodiments, the tech support server 422 can be an integral part of the BDD 414 to expedite diagnosis or resolution of patient's technical issues. In other embodiments, the tech support server 422 can be a separate server from the BDD 414 as shown in FIG. 4.

Advantages of separating the tech support server 422 from the BDD 414 can include an ability to operate the two databases under separate FDA classifications. For example, if the BDD 414 is deemed a Class III device, in some embodiments, the tech support server 422 can be operated as a Class I or Class II device by controlling the data routed to the tech support server 422. In some embodiments, it may be advantageous to have one or more tech support servers 422 with different FDA classifications. In that instance, one tech support server 422 with the same FDA classification as the BDD 414 can be embedded in the BDD 414 and handle patient's technical issues and data that are appropriate for the FDA classification of the BDD 414. Other issues and data appropriate to other FDA classifications can be routed to an alternate tech support server 422. By automatic, intelligent routing of patient's technical issues to appropriate tech support server 422, diagnosis and resolution of the issues can be performed expeditiously and the resources of the cloud computing architecture 410 can be preserved.

Figure 5A:
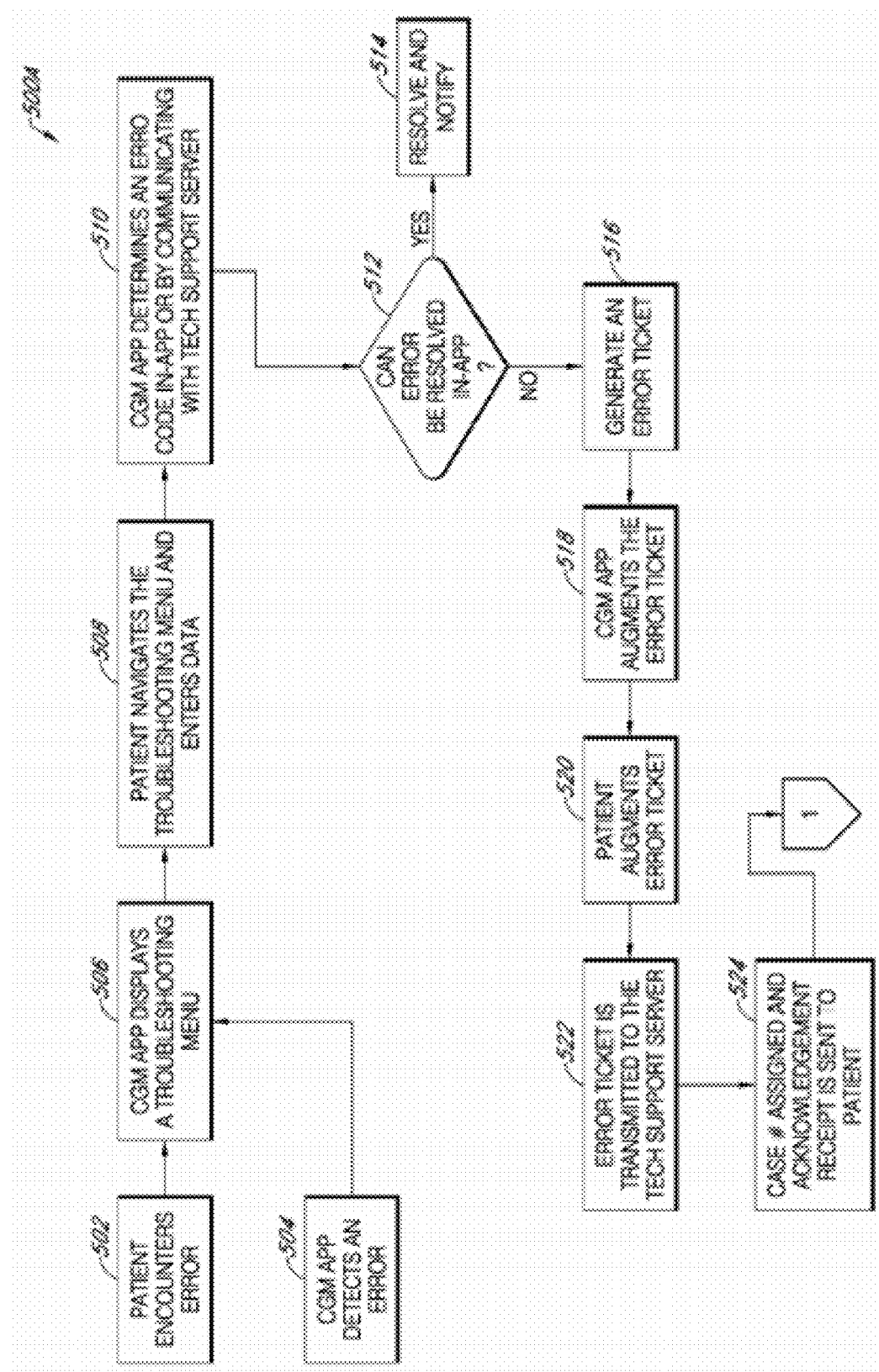
FIGS. 5A and 5B illustrate a flow chart of an example process to provide automated or semi-automated technical support in accordance with embodiments of the present technology.
Figure 5B:
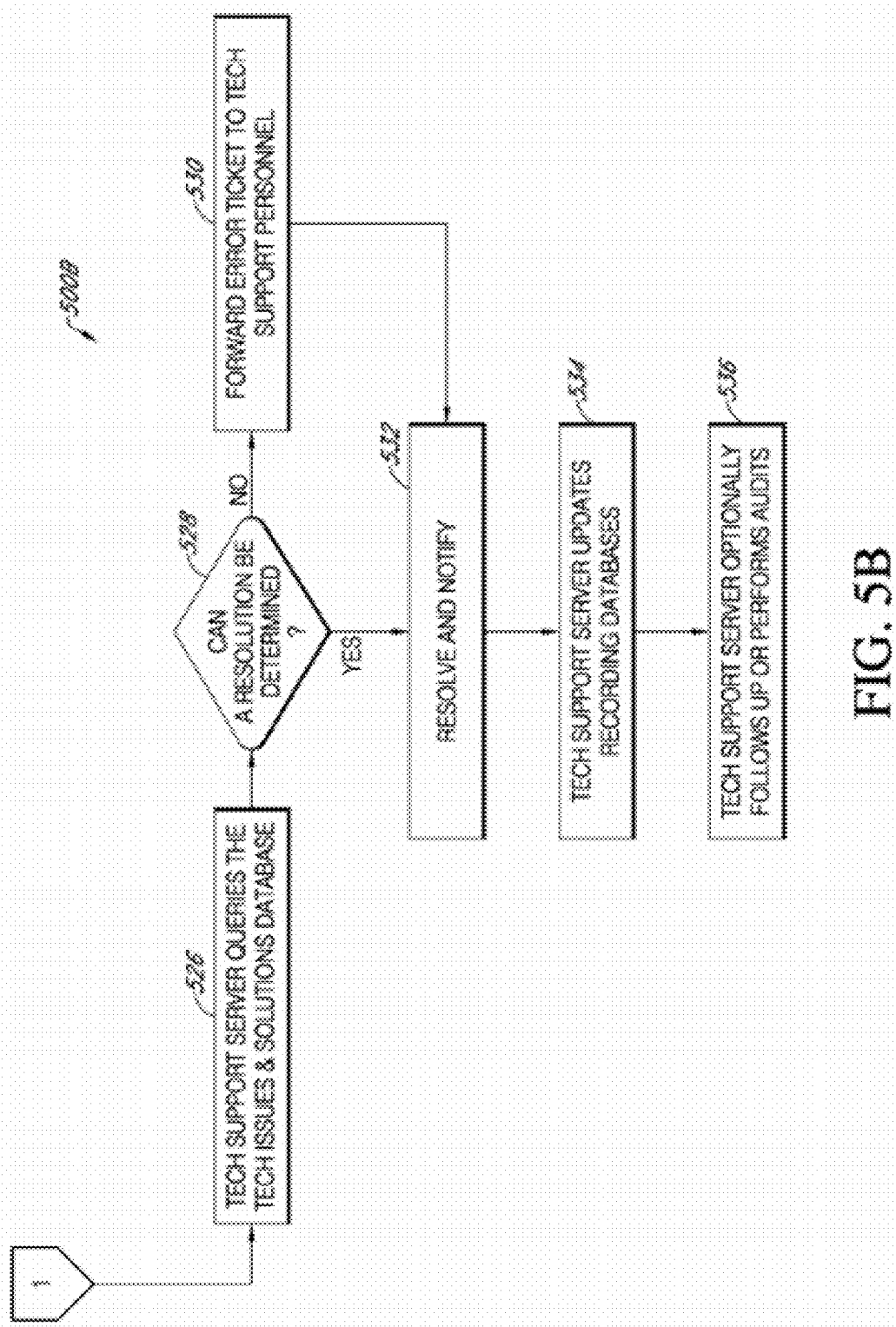

FIGS. 5A and 5B illustrate a flow chart 500A-B of an example process to provide automated or semi-automated technical support in accordance with embodiments of the present technology.

The process starts at block 502 or block 504 as the patient encounters an error or the analyte sensor application 330 detects an error. At block 506, the analyte sensor application 330 presents a troubleshooting menu (or the patient activates a troubleshooting menu within the analyte sensor application 330). At block 508, the patient navigates the troubleshooting menu and enters data relevant to the encountered issue. At block 510, the analyte sensor application 330 determines an error code applicable to the issue encountered. The determination of an error code, can happen within the analyte sensor application 330 or can be obtained from the tech support system 420. At block 512, it is determined whether the encountered issue can be resolved locally within the analyte sensor application 330. If yes, the process moves to block 514, where the issue is resolved and the results are reported to the patient, for example by displaying a notification on the display device 404. If no, the process moves to block 516 where an error ticket is generated. The process then moves to block 518. The analyte sensor application 330 can augment the error ticket with contextual or other additional data relevant to the error code associated with the issue encountered. In some embodiments, the analyte sensor application 330 can run algorithms associated with an error code to collect data relevant to that error code. The process then moves to block 520. The patient can augment the error ticket with annotations, contextual data, comments, historical data, or any other information relevant to the technical issue encountered. The process then moves to block 522. The error ticket is transmitted to the tech support system 420. As described, in some embodiments, the error ticket is transmitted to a tech support server 422 within the tech support system 420. The process moves to block 524. In some embodiments, a case number can be assigned to the error ticket and an acknowledgement receipt can be sent to the patient via analyte sensor application 330 or display device 404.

The process continues to block 526 (illustrated in FIG. 5B). The tech support server 422 can query the tech issues & solutions database 432 based on the error code and other information in the error ticket. The tech support server 422 can run searches in the tech issues & solutions database 432 and recall one or more applicable troubleshooting algorithms. In some embodiments, the troubleshooting algorithms may contain rankings or scores based on their applicability and prior favorable performance for troubleshooting a given error code. The tech support server 422 can utilize such rankings to identify a best-match troubleshooting algorithm. The process moves to bock 528, where it is decided whether a resolution to the technical issues in the error ticket can be determined. If no, the process moves to block 530 where the error ticket and any additional information appended by the tech support server 422 can be forwarded, for example via email, on screen chat, text alert, or other communication means, to the tech support personnel operating the tech support personnel computing system 434. The tech support personnel can take over handling of the error ticket, resolve the issue and notify the patient. In some embodiments, the tech support personnel can also manually handle any additional recording or processing steps associated with the resolution of an error ticket, thereby overwriting the automatic process of 500A-B.

If the tech support system 420 can determine a resolution of the technical issue associated with the error ticket, the process moves to block 532. The tech support system 420 resolves the technical issue in the error ticket and notifies the patient. The process moves to block 534 where the tech support server updates one or more recording databases of a medical device provider operating the patient's medical devices. As discussed, these recoding databases can include a tech issues & solutions database 432, patient records 424, product records 426, accounting 428 and regulatory records 430. The process optionally moves to block 536 where the tech support system 420 automatically follows up with the patient after a predetermined time (e.g., within 24 hours, or a week). The length of the period of time for follow up can be informed by the error code, type and severity of the issue encountered and any medical exigencies associated with a given error code. As described in some embodiments, the tech support personnel operating the tech support personnel computing system 434, can optionally override the automatic process 500A-500B at some stage. In some cases, when the tech support personnel resolve an issue, which was not resolved by the automatic process 500A-B, the tech support personnel can re-engage the process 500A-B, by handing off patient notification and subsequent documentation and recording to the block 532 and/or 534 of the process 500A-B. In some embodiments, the tech support personnel can handle the notification and documentation tasks manually. In such cases, the process 500A-B can perform audits and send reminders to the tech support personnel regarding these tasks.

Example Use Cases of Automated or Semi-automated Tech Support

When a patient experiences a device failure, the analyte sensor application 330 can generate an error ticket as described herein and transmit the error ticket to the tech support system 420. In some embodiments, the tech support server 422 can receive and analyze the error ticket. The tech support server 422 can transmit an acknowledgment response to the display device 404. The acknowledgment response can include an appropriate customer service message (e.g., a message of apology for the device failure, an explanation that the issue will further be investigated, the timeframe within which the medical device provider will reach back to the patient with a resolution and any instructions or remedial measures concerning what the patient may have to do in the meanwhile). The acknowledgment response initially sent to the display device 404 can be generated based on the error code associated with the error ticket transmitted to the tech support server 422.

Additionally, when the patient experiences a sensor failure, a sensor failure screen can appear on the display device 404 along with a "report problem/request sensor replacement" button displayed on the display device 404. In some embodiments, when the patient clicks on the report button, she is directed to a website, where she can be presented with one or more questionnaire forms containing questions associated with troubleshooting a sensor failure error and potential sensor replacement order. When the patient submits her responses, they can be transmitted to the tech support server 422 of the tech support system 420. In some embodiments, the questionnaire form may be presented to the patient as a menu option within the analyte sensor application 330, such that the patient does not have to visit a webpage. In some embodiments, a case number can be associated with the error ticket. The patient or the tech support personnel 434 can track or follow up on the status of the error ticket using the case number.

In some embodiments, the contents of the error ticket can be turned into an email and forwarded to the tech support personnel 434. In a semi-automated system, the tech support personnel 434 can manually perform the logging, recording and reporting that may be associated with the patient's request for tech support. In automated embodiments, as described herein, the logging, recording and reporting can be performed by the tech support system 420, without intervention from the tech personnel 434. In other embodiments, as described herein, a combination of automated and semi-automated implementations can be used where the tech support personnel intervene in some circumstances and not in others.

If sending a replacement sensor is identified as a resolution of a patient's technical issue, the tech support server 422 (or tech personnel 434) can book a replacement sensor to be shipped to the patient. By consulting the patient's records, the tech support server 422 can determine the delivery and shipment speed appropriate for the patient based on the urgency of the need to deliver a new replacement sensor. The patient may be notified via an email message, SMS, on-screen alert, or other means of communication. The patient can also be provided with shipment tracking information. In some embodiments, the tech support server 422, before ordering a replacement sensor, can check the patient records 424 to determine whether multiple sensors have been ordered within a short period of time. If the patient records 424 show that the patient has ordered multiple sensors within a short period of time, the tech support server 422 can flag the error ticket and request intervention from the tech support personnel 434, by sending an email, on-screen alert or other means of communication. The tech support server 422 can also send a notification message to the patient alerting her that multiple sensor replacements have been detected and a tech support technician will contact them.

Patient's medical devices, which are part of the analyte monitoring systems and architecture (e.g., sensors, receivers, etc.), can be configured to report any failure to the tech support system 420, for example, by generating and transmitting error tickets as described herein. In some embodiments, prior to transmission of an error ticket, the patient or patient's devices can augment an error ticket with appropriate contextual or additional data to assist in resolution of the issues. In some embodiments, the tech support system 420, upon receipt and analysis of an error ticket, may query the device or the patient associated with the error ticket for additional data to assist in resolving the technical issues. Depending on the failure reported, the tech support system 420 can take a number of actions, including confirming failure, sending acknowledgement receipts, beginning the process of product return or replacement, logging and recording the issue in appropriate databases including the patient records 424, product records 426, accounting 428 or regulatory records 430.

In some cases, the patient can report inaccuracies in sensor readings. The patient can compare the sensor readings reported on the display devices 404 to a manual reading from a self-monitoring blood glucose (SMBG) device. If the readings between the devices contain discrepancies, the patient can report an "inaccuracy" technical issue. The analyte sensor application 330 running on the display device 404 can present the patient with one or more menu options directed to troubleshooting sensor inaccuracies. The patient can request "inaccuracy analysis" for a given time period by interacting with menu options within the analyte sensor application 330. In some embodiments, if no time period is specified, the inaccuracy analysis can be performed from the beginning of a sensor reading session (a sensor reading session can, for example, start from when the patient clicks "start sensor" within a menu of the analyte sensor application 330). The analyte sensor application 330 can collect information from the patient, interact with the patient through questions/answers forms and present the patient with analysis and diagnosis regarding sensor inaccuracies. For example, the analyte sensor application 330 can present the difference between values obtained from a SMBG device (during one or more calibration event) and the CGM 402. The user can be prompted to enter data relevant to inaccuracy analysis, for example, the brand name of the SMBG and the type of calibration strip used. As described herein, if the analyte sensor application 330 determines that the perceived inaccuracy is within the acceptable tolerances of the CGM 402, it can present the patient with user manual, clinical trial data or other authoritative sources of information to reassure the patient of the correct operation of her medical device. If the patient or the analyte sensor application 330 determines that the sensor readings are inaccurate, an error ticket can be generated and transmitted to the tech support system 420 as described herein.

An example of automatic failure detection and resolution includes automatic detection of speaker failure. In the context of medical device, audible devices and components of the device can be important because the patients or the caregivers may rely on their correct operation to hear potentially life-saving or important medical alarms. Sometimes the patient inadvertently silences the speaker on their display device 404. If the patient uses a mobile device, such as a smart phone, as their display 404, it may be likely that the patient silences the speaker on their mobile phone from time to time, for example when attending a meeting or a public speaking event. The patient may not realize that potentially important medical alarms may also be silenced. In other cases, the speaker or other auditory devices within an analyte monitoring system may experience a mechanical, electrical or other hardware failure. The failure or inadvertent silencing of auditory devices within a medical device can be detrimental to patient's health. In some embodiments, the analyte sensor application 330, or other hardware or software within the analyte monitoring system can periodically check the operation of auditory components of the system 300.

Figure 6A:
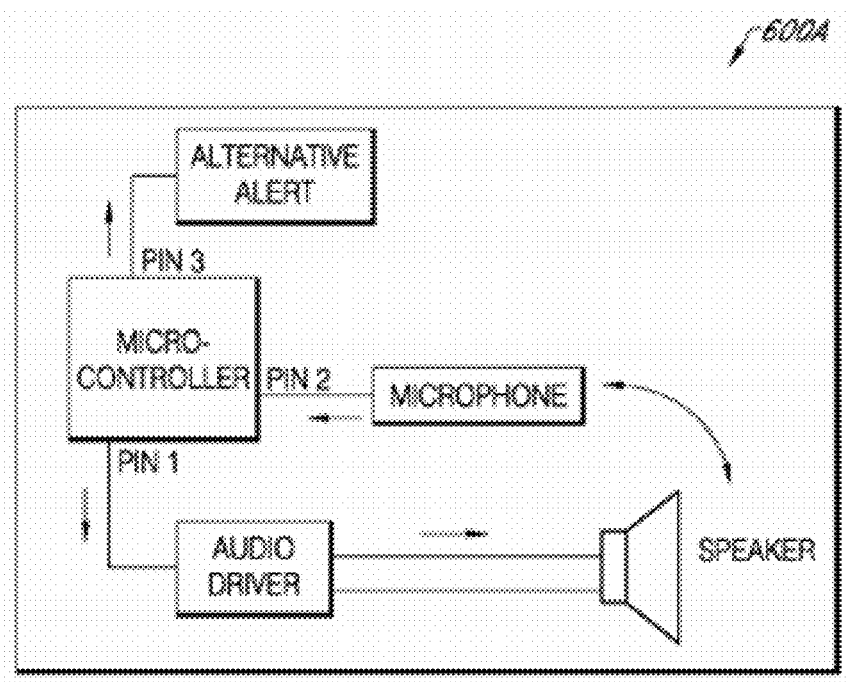
FIGS. 6A and 6B illustrate aspects of example systems for automatic failure detection.
Figure 6B:
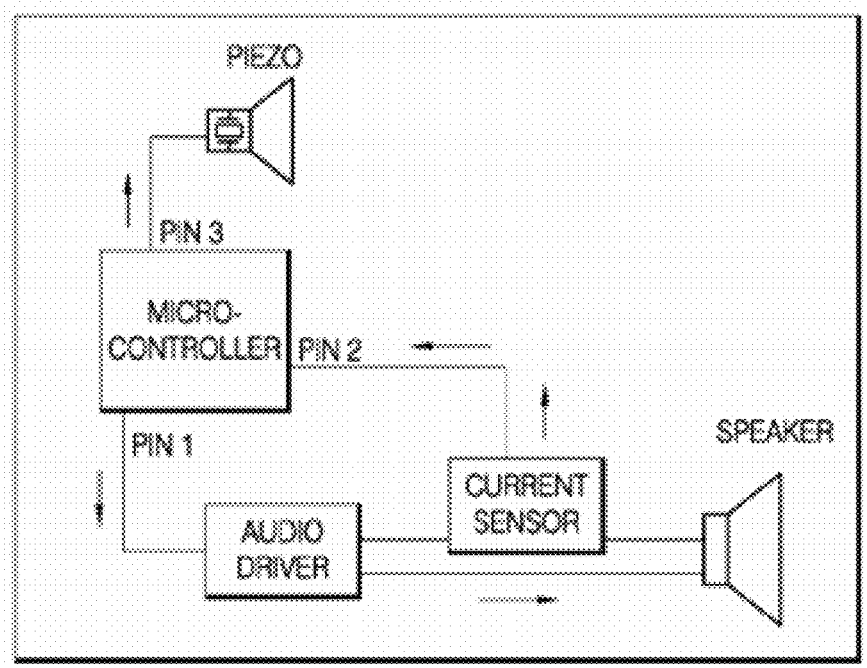

An example system of checking the correct operation of auditory devices is illustrated in FIGS. 6A and 6B. In some embodiments of the display devices 404, if a custom analyte monitoring device is used, the custom device can utilize a microphone or Hall Effect current sensor as a feedback element. By applying a control feedback loop, speaker failure can be detected. If such failure is detected, alerts can be issued using alternate methods.

The control loop can verify a speaker output during the times in which the speaker auditory output is expected. If the speaker has failed, the control loop senses no feedback current. Automatic alternative alert methods can be employed to ensure delivery of alerts. Alternative alerts can include small alternate piezo, an aggressive mechanical vibration, or a visual alert, for example, a text or other alert sent to the patient's phone connected by BLE.

The approach outlined above and illustrated in FIGS. 6A-6B can allow for automatic diagnosis of the speaker failure, without human intervention. The control loop's low profile components can be added to custom analyte monitoring devices without unduly taking up valuable space within the monitoring device.

Similar techniques (control loops, feedback sensing, control electronics, sensors, etc.) implemented in hardware or software can be used to automatically detect similar component failures (in addition to detecting auditory device failure) within the devices of the analyte monitoring system 300.

An example of automatic failure detection and resolution/mitigation includes automatic detection of data gaps. Data gaps in analyte data may have an adverse effect on the operations and functioning of the analyte monitoring system 300. The system relies on the (historical and current) analyte data to offer visuals, alerts and reminders to help the patient manage her health. Some data gaps can be caused by inadvertent shut down of the analyte sensor application 330. For example, a system or memory reset on the display device 404 or a Bluetooth server crash can cause inadvertent shut down of the analyte sensor application 330 and subsequent loss of data leading to data gaps. In some embodiments, the tech support system 420 can track the activity of its connected devices and their associated analyte sensor applications 330. If it is detected that an analyte sensor application 330 of a patient is offline, the tech support system 420 can send a silent push message to wake up the analyte sensor application. In some cases, the tech support system 420 can detect data gaps by comparison between copies of the same streams of data routed to different databases (e.g., the real time data routed to the real time server 408 or the bulk data routed to the BDC 412). Upon determining a discrepancy between the data stream copies stored in different servers, the tech support system 420 can send a status query or a silent push message to wake up the analyte sensor application 330. In some embodiments, the tech support system 420 can gather information related to the data gaps (e.g., whether the gap was caused by a memory reset, a Bluetooth server crash, timing of the data gap—whether night time or day time, etc.) The tech support system 420 can identify patterns in sources of data gaps and accordingly adjust the frequency and timing of sending silent pushes or wake up calls to various analyte sensor applications 330. For example, the tech support system 420 can determine that data gaps due to memory reset are more frequent for some patients during nighttime. The tech support system 430 can increase the frequency of silent pushes or wake up messages for those patients during nighttime.

An example of automatic tech support application of the embodiments described herein can include automatic ordering (or reordering) of CGM 402 or other parts within the analyte sensor system 308. In some embodiments of the analyte monitoring system 300, the CGM 402 or parts therein (e.g., the parts within the analyte sensor system 308 of FIG. 3B such as the sensor electronics) may need to be replaced after a predetermined period of use. The initial start date of new parts can be determined and stored when the cloud computing architecture 410 first receives an upload from a patient's newly installed device, or newly replaced part. The tech support system 420 can track the age of various components of the analyte monitoring system 300 or the analyte sensor system 308. The tech support system 420 can be configured to automatically check its relevant databases on the components age-out date (or some predetermined time prior to age-out date) to determine whether a replacement part has been scheduled for shipping. If yes, the tech support system 420 can notify the patient of the scheduled shipment and associated information, such as expected delivery date, tracking number and billing information. If no replacement part has been scheduled as expected, the tech support system 420 can notify the patient accordingly and request authorization for scheduling and shipment of replacement parts.

Figure 7:
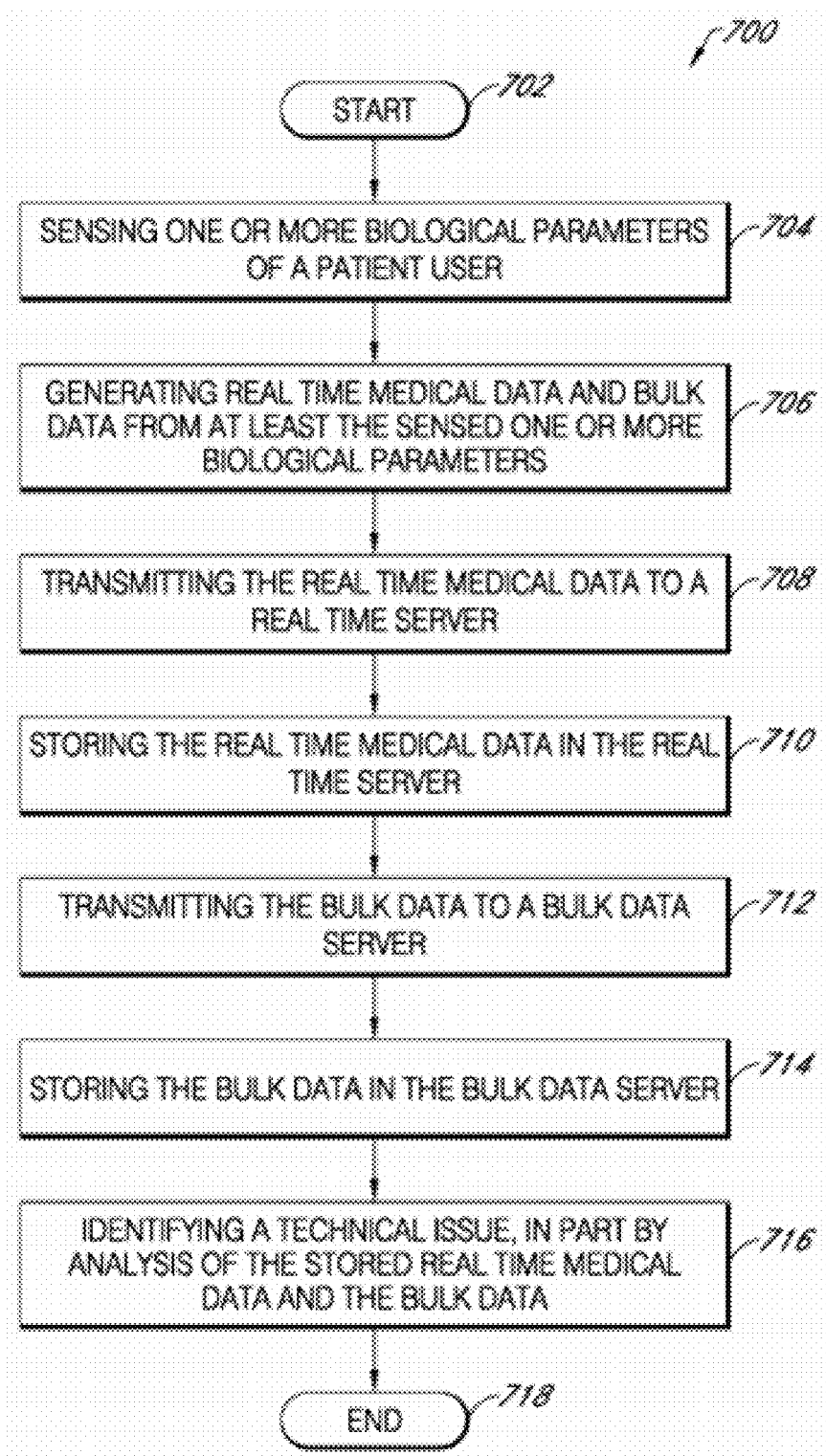
FIG. 7 illustrates a flow chart of an example to provide automated or semi-automated technical support in accordance with embodiments of the present technology.

FIG. 7 illustrates a flow chart 700 of an example to provide automated or semi-automated technical support in accordance with embodiments of the present technology. The process starts at block 702. At block 704, the process continues by sensing one or more biological parameters of a patient user. At block 706, the process continues by generating real time medical data and bulk data from at least the sensed one or more biological parameters. At block 708, the process continues by transmitting the real time medical data to a real time server. At block 710, the process continues by storing the real time medical data in the real time server. At block 712, the process continues by transmitting the bulk data to a bulk data server. At block 714, the process continues by storing the bulk data in the bulk data server. At block 716, the process continues by identifying a technical issue, in part by analysis of the stored real time medical data and the bulk data. The process ends at the block 718.

Early Failure Detection and Diagnosis in Continuous Analyte Monitoring Systems

The detection of the concentration level of glucose or other analytes in certain patients may be vitally important to their health and safety. For example, patients with diabetes may need to monitor their glucose levels to determine when medication is needed to reduce their glucose levels or when additional glucose is needed. Accordingly, analyte monitoring systems have been developed for continuous in vivo monitoring of analytes, such as glucose levels, in bodily fluids to provide efficient means for users (wherein a user may be the patient, a caretaker of the patient, a physician, a parent, a relative, a guardian, a teacher, or any other individual that has an interest in the well-being of the patient) to track such information. However, in some cases, analyte monitoring systems have been found to occasionally provide false readings due to one or more errors associated with the continuous analyte monitoring, including, but not limited to, a prematurely failing and/or failed component of the system.

As used herein, an "error" generally refers to a deviation from an intended performance or behavior, and an "error" may constitute a "failure" when the deviation is permanent such that the system component is invariably unable to perform or function as intended, including any deviations from the component's performance specifications or intended use.

For patients whom solely rely on these systems to accurately track and provide analyte data, these errors may pose a substantial threat to patient health and safety, and in some cases, may be life altering. For this reason, early failure detection is a significant consideration in the design of medical device equipment, including analyte monitoring systems. The term "early failure" (interchangeably used with "premature failure") generally refers to a state of a component prior to failure.

Through early failure detection, diagnosis, and the elimination of factors likely contributing to the failure, analyte monitoring systems may provide the necessary accuracy and reliability patients expect. From a company's perspective, using technology to proactively monitor and control risk may also reduce regulatory interaction, thereby allowing a company producing such systems to experience faster regulatory clearance, reducing overall cost of compliance. In addition, early failure detection in analyte monitoring systems may provide manufacturers with the opportunity to discover early indications of unexpected quality and reliability problems to better inform product design in hopes of reducing warranty claims brought by patients using the systems.

However, existing analyte monitoring systems, including continuous analyte monitoring systems, are not capable of automatically identifying when errors associated with the system are indicative of failing or failed components to allow for correct, proactive intervention. For example, continuous analyte monitoring systems generally require manual intervention by technical support personnel which may not be efficient, nor easily scalable to meet increased demands as the patient population utilizing continuous analyte monitoring systems increases. For example, users wishing to resolve equipment failures or other performance problems with their continuous analyte monitoring system often need to contact remote technical support personnel and provide relevant information regarding their particular analyte monitoring system, their recent activities, their deployment routine, patch site information, etc. Providing a complete set of relevant information needed by technical support personnel to accurately and efficiently solve system errors, and in some cases identify the system error is caused by a failing or a failed component of the system, requires answering questions which the user may not know, may not recall, or may inaccurately report to technical support.

Moreover, unexpected component or system performance anomalies may be the result of seemingly unrelated changes to a patient's daily routine, nutrition, activities, etc., and thus, the user may not have the requisite level of knowledge to provide valuable information to technical support. For example, a patient's analyte sensor may have significant performance degradation related to poor manufacture of the device and fail irrespective of a patient's activity, health, installation of the sensor, etc. Therefore, manual intervention by technical support personnel may not be efficient and in some cases, may fail to accurately identify one or more components in the continuous analyte monitoring system that have indeed failed, or are failing, because all necessary information is not obtained or the information obtained is erroneous. Thus, integrity of conventional continuous analyte monitoring systems may be compromised. For this reason, continuous analyte monitoring system capable of automatic early failure detection may be desired.

Certain embodiments described herein involve continuous analyte monitoring systems capable of automatically detecting early failure or failure of one or more components of the continuous analyte monitoring system. For example, certain embodiments of the present disclosure provide one or more prediction algorithms capable of detecting early failure or failure associated with an analyte sensor (e.g., analyte sensor 375 of FIG. 3B, also designated with the numeral 10 in FIG. 1A) and/or a transceiver (e.g., transceiver 360 of FIG. 3B, also referred to herein as transmitter 360) of the continuous analyte monitoring system. The prediction algorithm(s) may (1) determine whether error message(s) generated by the continuous analyte monitoring system correlate to early failure or failure of the analyte sensor or the transmitter, or in the alternative, whether the generated error messages are a false positive failure detection and (2) further ascertain a root cause of the error when the error is a false positive failure detection.

As described previously, an "error" generally refers to a deviation from an intended performance or behavior, and the continuous analyte monitoring system described herein may be configured to generate one or more error messages when behavior of one or more components of the continuous analyte monitoring system deviate from their intended behavior. Such error messages may be referred to herein as event indications. For example, when sensed signals by an analyte sensor of the continuous analyte monitoring system are below a minimum error threshold configured for the analyte sensor, the continuous analyte monitoring system may identify an "error" associated with the analyte sensor exists. In response, the continuous analyte monitoring system may generate an event indication indicating this error associated with the analyte sensor. Where a plurality of event indications are generated for the analyte sensor, the continuous analyte monitoring system may perform analytics on the plurality of event indications to ascertain a root cause (e.g., using the prediction algorithm(s)). In some cases, the system may determine the analyte sensor is prematurely failing, or has failed, thereby causing the system to generate event indications indicating the sensed signals are below the configured error threshold. However, in some other cases, the system may determine that the analyte sensor is not failing and instead identify that the event indications are being generated by the system because the analyte sensor has fallen off the body of the patient.

The continuous analyte monitoring system configured to automatically perform root cause analysis to ascertain whether errors associated with the system are related to a failing or failed component of the system provides improved reliability and efficient diagnosis over existing systems. Further, the continuous analyte monitoring system presented herein may be easily scalable to meet increased demands, while also being capable of performing analysis different for each unique system and/or varying patient data.

According to certain aspects, the continuous analyte monitoring system may include an analyte sensor system (e.g., such as analyte sensor system 308 of FIGS. 3A and 3B) having at least an analyte sensor (e.g., analyte sensor 375 of FIG. 3B, which may also be designated with the number 10 in FIG. 1A) and a transmitter (e.g., transceiver 360 in FIG. 3B, which may also be a part of item 12 in FIG. 1A) and in communication with at least one display device (e.g., display device 310 of FIGS. 3A and 3B) having a processor (e.g., processor/microprocessor 35 of FIG. 3B).

As further described herein, an application executed by the processor of the display device (e.g., analyte sensor application 330 executed by processor 335 of FIG. 3B) in communication with the analyte sensor system may include software instructions or algorithms for resolving errors associated with a patient's continuous analyte monitoring system. One algorithm may include a prediction algorithm capable of detecting early failure or failure associated with components of the continuous analyte monitoring system. Accordingly, analyte sensor application 330 may be able to perform root cause analysis, via processor 335, to determine whether one or more components of the continuous analyte monitoring system have failed, are prematurely failing, or whether the continuous analyte monitoring system has incorrectly indicated the presence of a failure when, in fact, no failure has occurred.

According to some aspects described herein, analyte sensor application 330 executing on processor 335 may be capable of performing such early failure detection and diagnosis irrespective of a server (e.g., such as server system 334 illustrated in FIG. 3A).

Root cause analysis performed by processor 335 (1) identifies one or more root causes of a plurality of event indications generated based on one or more errors associated with the continuous analyte monitoring system and (2) determines corrective actions to address the one or more root causes. The root cause analysis process provides a way to analyze multiple different factors that may have contributed to the generation of each of the event indications and determine what factor(s) are the underlying root cause. In some examples, the root cause analysis seeks to (1) isolate the root cause of an error in the continuous analyte monitoring system, (2) accurately determine actions for preventing similar future errors from occurring, and (3) provide a recommendation for removing the root cause or take action to remove the root cause.

As an illustrative example, a continuous analyte monitoring system deployed on a patient may generate (e.g., via transceiver 360 of analyte sensor system 308) a plurality of event indications indicating sensed signals (e.g., generated based on sensed analyte levels of the patient) are below a minimum configured error threshold. Although a plurality of event indications indicating sensed signals are below a minimum threshold may indicate to the continuous analyte monitoring system that analyte sensor 375 has failed, before making this determination, processor 335 may perform a root cause analysis to more accurately determine a root cause of the generated event indications. Processor 335 may take into account many factors which may have contributed to generation of the event indications. For example, where the patient is a male, is 80 years old, has dry and flaky skin, and deploys their analyte sensor on the back side of their arm, the processor may consider each of these factors when making the determination. Following completion of the analysis, processor 335 may determine that the plurality of event indications were generated because analyte sensor 375 has fallen off the body of the patient. Processor 335 may further ascertain that analyte sensor 375 has fallen off the patient's body due to severe dryness and flaking of the patient's skin.

Accordingly, the root cause analysis provides a more accurate determination for why one or more errors exist with the continuous analyte monitoring system, beyond merely identifying the errors are caused by a failing component of the system. In this way, the continuous analyte monitoring system may recommend or take one or more actions to help prevent similar errors from reoccurring such that when a component of the continuous analyte monitoring system does, in fact, fail, processor 335 will be able to accurately identify this failure (or premature failure). Such root cause analysis may be described in more detail below.

To perform the root cause analysis, processor 335 may receive analyte measurements from transceiver 360, and in some cases event indications generated and transmitted by transceiver 360. In some embodiments, to perform the root cause analysis, the processor 335 may further receive information from a server (e.g., server system 334 of FIG. 3A, etc.). In some embodiments, processor 335 may further receive information from the patient to better inform the root cause analysis. With this additional information, processor 335 may more precisely identify patterns and trends for the autonomous detection of component failures associated with the patient's analyte monitoring system.

Figure 8:
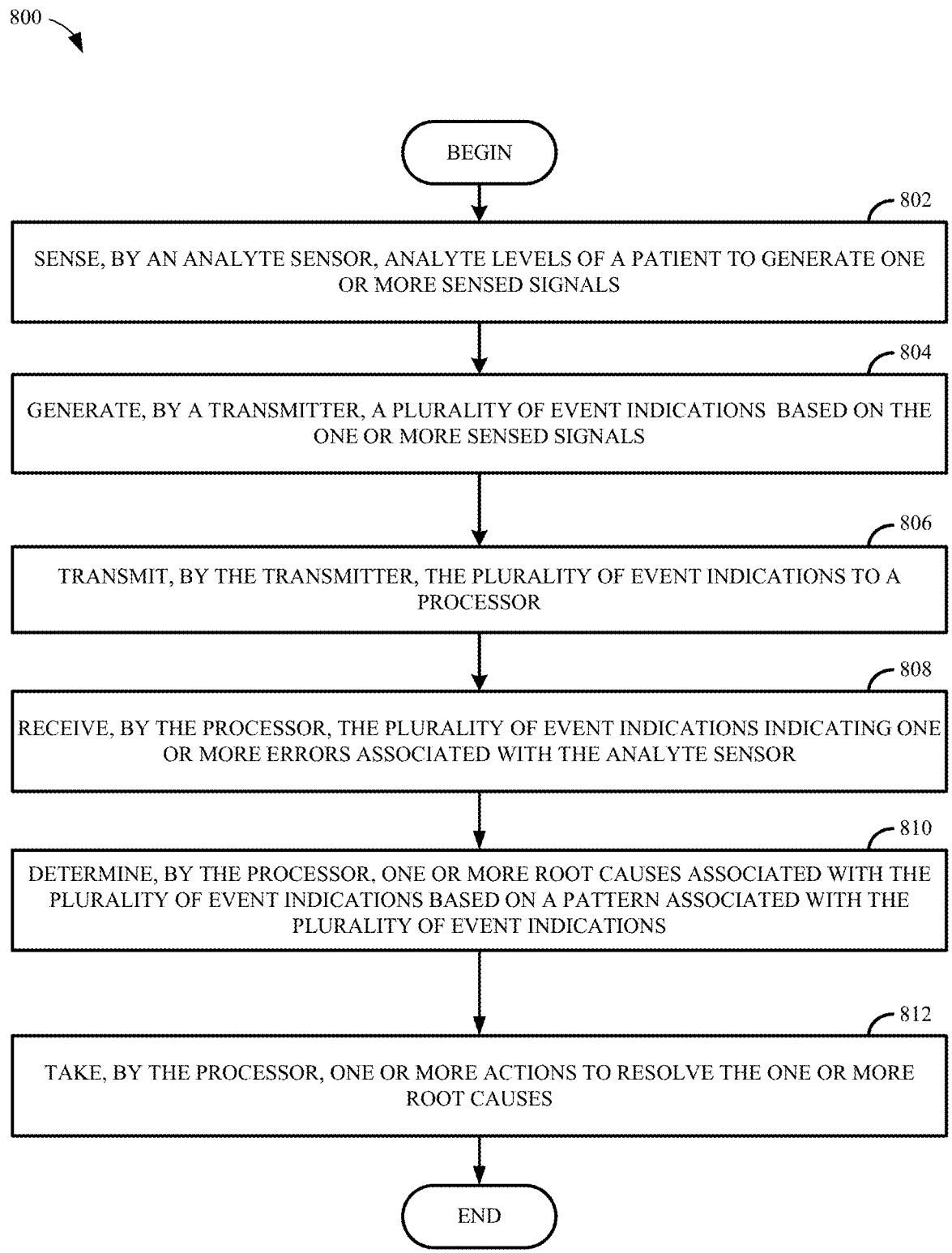
FIG. 8 illustrates a flow chart associated with an example method for automatically self-diagnosing and resolving performance problems detected and associated with an analyte sensor of a continuous analyte monitoring system, in accordance with embodiments of the present technology.

FIG. 8 illustrates a flow chart 800 associated with an example method for automatically self-diagnosing and resolving performance problems detected and associated with an analyte sensor of a continuous analyte monitoring system, in accordance with embodiments of the present technology. The operations 800 may be performed, for example, by components of a continuous analyte monitoring system, such as components of continuous analyte monitoring system 302 shown in FIG. 3B. For example, in certain embodiments, operations 800 may be performed by at least analyte sensor 375, transceiver 360 (e.g., transmitter 360), and processor 335 of continuous analyte monitoring system 302 illustrated in FIG. 3B. Although steps 808, 810, and 812 in the embodiment of FIG. 8 are performed by processor 335, in certain other embodiments, steps 808, 810, and 812 may be performed by server system 334, and in certain other embodiments, steps 808, 810, and 812 may be performed by a combination of processor 335 and server system 334.

At block 802, operations 800 begin by an analyte sensor (e.g., analyte sensor 375), sensing analyte levels of a patient to generate one or more sensed signals. As described above, analyte sensor 375 may use any known method, including invasive, minimally invasive, and non-invasive sensing techniques, to provide a data stream indicative of the concentration of analyte in a patient. The data stream may be an electrical sensor current, typically in the form of, raw data signals (e.g., sensed signals). In some embodiments, the analyte sensor is a glucose sensor capable of measuring the concentration of glucose. According to certain aspects, new measurements may be generated by analyte sensor 375 often enough to adequately monitor analyte levels.

At block 804, operations 800 continue by a transmitter (e.g., transceiver 360, also referred to herein as transmitter 360) generating a plurality of event indications based on the one or more sensed signals. According to certain aspects, transmitter 360 may gather the electric sensor current from analyte sensor 375 for conversion into a calibrated and/or filtered data streams that are used to provide useful values of analyte for analysis. For example, in some aspects, the transmitter may determine estimated glucose values (EGV data) for analysis.

In some embodiments, in addition to generating estimated analyte values based on the electrical sensor current, transmitter 360 may be configured to generate a plurality of event indications based on the electrical sensor current (interchangeably referred to herein as sensed signals). In such embodiments, transmitter 360 may be referred to as a "smart transmitter" given its ability to perform additional processing (e.g., event indication generation).

According to certain aspects, event indications generated by transmitter 360 may indicate one or more errors associated with analyte sensor 375. The plurality of event indications may indicate (1) signals sensed by analyte sensor 375 above a configured error threshold (e.g., event indications related to a very high signal error), (2) signals sensed by analyte sensor 375 below a configured error threshold (e.g., event indications related to a very low signal error), (3) errors associated with a calibration of analyte sensor 375, (4) signals sensed by analyte sensor 375 having a rate of change higher than a threshold (e.g., event indications related to high or low spikes in sensed signals), or any combination thereof.

At block 806, operations 800 continue by the transmitter (e.g., transceiver 360) transmitting the plurality of event indications to a processor (e.g., processor 335). According to certain aspects, transmitter 360 may transmit the plurality of event indication to processor 335 for processing to ascertain a root cause of the plurality of event indications.

At block 808, operations 800 continue by the processor (e.g., processor 335) receiving the plurality of event indications indicating one or more errors associated with the analyte sensor (e.g., analyte sensor 375). Processor 335 receiving these event indications indicating one or more errors associated with analyte sensor 375 may analyze whether a root cause of the generation of these event indications corresponds to a prematurely failing analyte sensor 375, an already failed analyte sensor 375, an analyte sensor 375 that is no longer attached to the body of the patient (e.g., analyte sensor 375 that has fallen off or has become detached thereby creating a gap between an interface of analyte sensor 375 and the patient's body), or some other reason, explained in more detail herein.

At block 810, operations 800 continue by the processor (e.g., processor 335) determining one or more root causes associated with the plurality of event indications based on a pattern associated with the plurality of event indications. According to certain aspects, root cause analysis performed by processor 335 in the continuous analyte monitoring system may involve four major steps including, the gathering of necessary data to be able to localize errors associated with the continuous analyte monitoring system, event and causal factor prediction, root cause identification, and recommendation generation and implementation.

At a first step of the root cause analysis process, processor 335 may collect all necessary data to be able to localize an error with respect to the continuous analyte monitoring system. As described previously, processor 335 may receive analyte data and a plurality of event indications from transmitter 360 of the continuous analyte monitoring system to begin processing. However, in some cases, this information may not be sufficient to accurately determine a root cause of the error(s). If signals sensed by analyte sensor 375 fail to provide all essential data, the root cause analysis may not be complete. For this reason, in some embodiments, processor 335 may receive additional information to further inform the root cause analysis.

As mentioned, an event indication may be generated for reasons beyond a failing component of or associated with the continuous analyte monitoring system. For example, excessive pressure on analyte sensor 375 may result in very low sensed signals detected by analyte sensor 375 while excessive moisture at an interface of analyte sensor 375 and the patient may result in very high sensed signals detected by analyte sensor 375. Without additional information, processor 335 may inaccurately assume analyte sensor 375 has failed, when, in fact, other factors were contributing to the error. Accordingly, in some embodiments, processor 335 may be further configured to receive secondary sensor data associated with the patient. The secondary sensor data may be used by processor 335 to more accurately identify an underlying root cause of the error. Secondary sensors may provide quick, reliable data thereby removing the need to inquire further with a patient to collect pertinent data for analysis.

In some cases, the secondary sensory data may include accelerometer data associated with movement of analyte sensor 375. For example, a patient whom regularly engages in walking, running, exercise, etc. may have increased, or prolonged periods of, perspiration that may impact signals sensed by analyte sensor 375. As another example, a patient whom regularly engages in swimming may expose analyte sensor 375 to prolonged periods of moisture which may also impact signals sensed by analyte sensor 375. Accordingly, accelerometer data may be used to determine previous activities of a patient based on a mapping between patient acceleration and patient activity to inform the root cause analysis.

In some cases, the secondary sensory data may include temperature data indicating a temperature associated with analyte sensor 375. As an example, temperature associated with analyte sensor 375 may dramatically decrease when sensor 375 becomes detached from the patient's body. Thus, temperature sensor data may be used to determine that analyte sensor 375 has become detached from the patient's body, as opposed to determining that analyte sensor 375 has failed. As another example, placement of analyte sensor 375 on certain areas of a patient's body may have adverse impacts on the signals sensed by analyte sensor 375. Thus, temperature sensor data may be used to identify a placement of analyte sensor 375 given certain areas of the body may have higher temperatures than other areas. Under arm or armpit placement of analyte sensor 375 on the patient's body may be one deployment location that may cause a temperatures associated with analyte sensor 375 to increase.

In some cases, the secondary sensory data may include gyrometer data indicating an orientation of analyte sensor 375. As described herein, excessive pressure on analyte sensor 375 may result in very low sensed signals detected by the analyte sensor. A gyrometer may be capable of detecting an orientation of analyte sensor 375 to determine whether there is too much pressure on analyte sensor 375 thereby causing sensor 375 to collect very low signals. For example, gyrometer data may indicate that analyte sensor 375 of a patient is in a horizontal position, facing downward, and processor 335 may use this gyrometer data to determine that, based on an orientation of sensor 375, the patient is likely laying on their stomach. Processor 335 may then use this assumption to determine that very low signals sensed by analyte sensor 375 are due to excess pressure caused by the patient laying on their stomach, as opposed to determining that analyte sensor 375 has failed.

In some cases, the secondary sensory data may include moisture detection data indicating a moisture level at an interface between analyte sensor 375 and the patient (also referred to herein as the patch site of analyte sensor 375). In particular, processor 335 may leverage moisture data to determine whether increased moisture at an interface between analyte sensor 375 and the patient is contributing to very high signals being sensed by analyte sensor 375. As an example, a moisture sensor may shed light on a patient's routine (e.g., patient showers twice a week, patient regularly engages in swimming, etc.) or a patient's skin attributes (e.g., perspiration levels of the patient) to better inform the root cause analysis.

In some cases, the secondary sensory data may include heart sensor data indicating a heart rate of the patient. For example, a patient's heart rate may be indicative of the types of activities the patient actively engages in. As described herein, information about a patient's recent activities may be essential information for processor 335 to have when performing the root cause analysis.

While secondary sensor data provides access to a depth of reliable data which a user may not be able to provide, information obtained from sensor technology may be costly and/or limited as to the type of data that may be collected. For example, medical history of a patient may provide many insights during the root cause analysis; however, a sensor may not be able to provide such information. For this reason, additional methods of collecting pertinent data, including patient questionnaires, may be contemplated.

For example, in some embodiments, processor 335 may be further configured to receive one or more answers to one or more questions presented to a user, thus, determining one or more root causes may be further based on the answers. As used herein, a user may be the patient, or in the alternative, a user may be a patient's caregiver, physician, relative, etc. In particular, a user may choose to report further information about an event indication or provide other contextual information to be included with the event indication. In some embodiments, the questionnaires may be in a form where answers are collected by receiving inputs and selections via drop down menus, radio buttons or other forms where limited free text is allowed. Collecting data in this form may allow for expedient analysis, for example, via running data analytics by processor 335.

In some cases, certain questions may be associated with a skin condition of the patient. For example, questions may inquire about perspiration levels of the patient, dryness of the patient's skin, roughness of the patient's skin, as well as any skin allergies or reactions the patient has previously experienced.

In some cases, certain questions may be associated with recent activities of the patient. For example, a user may be provided with a multiple-choice question inquiring into whether the patient regularly engages in any sports activities known to have an effect on patch life of the analyte sensor (e.g., swimming, sports with high movements in patch site regions, "high impact" in site regions, etc.).

In some cases, certain questions may be associated with health conditions of the patient. For example, questions may inquire about a patient's body mass index (BMI), skin disorders of the patient, family health history, or health conditions that may have an impact on adhesion of the analyte sensor to the patient.

In some cases, certain questions may be associated with nutrition of the patient. For example, questions may inquire into a diet of the patient, and more specifically, whether the patient has a high glycemic diet or a low glycemic diet. A patient's diet may provide many valuable insights to the root cause analysis, including, but not limited to, a patient's rate of glucose release or a patient's sebum content level, where sebum is typically connected to hair follicles and used to form a protective barrier on the skin to prevent excessive water loss. For example, a patient whom consumes food low on the glycemic index (GI) scale may tend to release glucose slowly and steadily, while a person whom consumes food high on the GI scale may release glucose more rapidly. Further, a patient whom consumes high GI foods may be able to offset hypo- (or insufficient) glycemia, as opposed to a patient whom does not consume high GI foods. Understanding a patient's rate of glucose release may help to differentiate between scenarios where a spike in a patient's glucose values occurs due to the patient's diet versus scenarios where a spike in a patient's glucose value occurs due to a failing component of the continuous analyte monitoring system. In general, understanding a patient's diet helps to better inform why glucose values specific to a patient appear to be abnormally high, abnormally low, experiencing a quick rate of change, experiencing a slow rate of change, etc. which may help to accurately identify situations where an actual failure (or early failure) of a component is occurring. As another example, a patient whom consumes food low on the GI scale may have reduced sebum; therefore, the patient may have increased skin shedding (e.g., flaking) which in turn affects adhesion of an analyte sensor to the patient's skin.

Questions associated with nutrition of the patient may also inquire into the water intake of the patient over a specified period of time to provide awareness as to a condition of the patient's skin. For example, a patient whom regularly drinks water may mitigate transepidermal water loss (TEWL) (e.g., rate of water vapor that is lost to the atmosphere) and increase collagen function (e.g., increase skin elasticity) of the patient's skin thereby reducing a potential for analyte sensor 375 to fall off the body of the patient. Proper hydration may stabilize the structure of collagen, preserving its function to keep skin elastic. Increased collagen-water structures may reduce the flow of water to the skin boundary, thereby reducing TEWL.

In some cases, one or more questions presented to a user may include one or more questions associated with an interface between analyte sensor 375 and the patient (e.g., patch site). Questions may inquire into a preferred placement of analyte sensor 375 by the patient (e.g., preferred placement on a patient's abdomen, lower back, back side of arm, etc.), an orientation of analyte sensor 375, whether analyte sensor 375 is worn along skin lines of deformation, and/or whether analyte sensor 375 is placed in a location on the skin with a significant amount of hair. As an example, analyte sensors worn along skin lines of deformation may be more prone to falling off than analyte sensors that are placed on a patient's arm due, at least in part, to constant bending at the patch site. Such information may further inform the root cause analysis performed by processor 335.

In some cases, certain questions may be associated with a deployment routine of analyte sensor 375 by the patient. For example, questions may inquire into a time of day analyte sensor 375 is generally applied to the body (e.g., morning/afternoon/evening), how long after showering the patient waits before re-applying analyte sensor 375 (e.g., directly after a patient's shower, six hours after a patient's shower, twenty-four hours after a patient's shower), whether any lotions or powders are used on the skin prior to deployment of analyte sensor 375, and/or whether any cleaners, enhancers, or overlays are used.

In some cases, certain questions may relate to an age, gender, and/or race of the patient. In some cases, certain questions may relate to adhesion of analyte sensor 375 to the patient's skin.

Accordingly, as described above, processor 335 may collect secondary sensor and questionnaire data to further inform the root cause analysis. In some cases, collected secondary sensor data and/or questionnaire data may be used to verify data of each other, or analyte levels sensed by analyte sensor 375.

At a second step of the root cause analysis process, processor 335 may engage in events/causal factor prediction. Events and causal factor prediction may assist the processor 335 in verifying the sequence of events/factors leading to the generation of an event indication. Events/causal factor prediction may help to organize the collected data (including analyte data, the plurality of event indications, secondary sensor data, questionnaire answers, and/or one or more patterns supplied by a server system 334, described below), guide the investigation, validate and confirm the true incident sequence, and identify and validate probable causes and contributing factors. In particular, three methods may be used to determine one or more root causes associated with a plurality of event indications: a "walking back" method, pattern recognition, and machine learning.

In some embodiments, processor 335 may use a "walking back" method to determine one or more root causes associated with a plurality of event indications. The "walking back" method may include comparing a recent event indication indicating an error associated with analyte sensor 335 to one or more event indications, also indicating errors associated with analyte sensor 335, generated prior to the recent event indication. For example, a recently received event indication transmitted to processor 335 by transmitter 360 may indicate an error associated with analyte sensor 375. In such an example, processor 335 may compare this event indication to an event indication received from transmitter 360 ten minutes prior, twenty minutes prior, etc. to determine whether a root cause may be ascertained across the plurality of event indications.

In some embodiments, processor 335 may use pattern recognition to determine one or more root causes associated with a plurality of event indications. Pattern recognition is a process that determines whether any regularities exist within a compilation of data (e.g., event indications, secondary sensor data, patient questionnaire answers, and additional information necessary for analysis). Pattern recognition may be broken into three main parts: (1) an explorative part, where a predictive algorithm, executed by processor 335, searches for patterns among the collected data, (2) a descriptive part, where the predictive algorithm begins to categorize recognized patterns (segment data), and (3) an analysis part, where the segmented data is analyzed. For example, the predictive algorithm at processor 335 may analyze a pattern of data from the patient to determine whether actions of the patient are artificially causing analyte sensor 375 to appear like analyte sensor 375 has failed, although analyte sensor 375 is still functioning properly.

In some embodiments, processor 335 may use machine learning to determine one or more root causes associated with a plurality of event indications. Machine learning techniques, whether deep learning networks or other experiential/observational learning systems, may be used to build a model trained to recognize patterns between generated event indications indicating errors associated with the continuous analyte monitoring system and possible root causes for the event indications. The model may be based on sample data, known as "training data", in order to make predictions without being explicitly programmed to do so. In some cases, "training data" of known pluralities of event indications mapped to one or more root cases may be used to train the model.

According to certain aspects, processor 335 may be further configured to receive an indication from a server (e.g., server system 334 of FIG. 3) indicating a pattern associated with event indications for a population of patients. Processor 335 may use the received pattern associated with event indications for a population of patients to determine the one or more root causes. For example, after receiving and/or generating three event indications indicating that sensed signals are above a maximum configured threshold, processor 335 may determine a root cause of the three event indications based, at least in part, on one or more patterns received from server system 334. In particular, one pattern associated with event indications for a population of patients may include the repetition of event indications indicating that sensed signals are above a maximum threshold, combined with repetitions of periods where the patient engaged in swimming, as well as among other data collected. Sever system 334 may have previously identified that such a pattern is indicative of increased moisture at the analyte sensor, and not a failing sensor. Accordingly, the received pattern of high sensed signals (e.g., the three event indications) in addition to other data from the patient (e.g., activity levels sensed by an accelerometer and/or moisture detection data sensed by a moisture sensor) may be compared against this specific pattern created based on population data to determine that a root cause of the high sensed signals is being caused by increased moisture at the analyte sensor when the patient's data aligns with the pattern received from server system 334.

At a third step of the root cause analysis process, processor 335 may engage in root cause identification where processor 335 identifies one or more root causes associated with the plurality of event indications. As described herein, an event indication may, in some cases, indicate a prematurely failing or failed analyte sensor 375 or transmitter 360 of the analyte monitoring system; however, this may not always be the case. Instead, where an event indication comprises a false positive failure detection, processor 335 may further ascertain a root cause of the false positive indication.

According to certain aspects, event indications corresponding to one or more errors associated with analyte sensor 375 (e.g., sensor-triggered event indications generated by transmitter 360) may include error codes related to very low sensed signals, error codes related to very high sensed signals, error codes related to sensor calibration, and error codes related to a residual operations failure mode.

Error codes related to very low sensed signals may be generated by transmitter 360 when multiple consecutive events indicate that the sensed signals are below a minimum configured error threshold. Configured error thresholds may include a minimum configured error threshold and a maximum configured error threshold. Configured error thresholds may be consistent across all manufactured continuous analyte monitoring systems or configured to be patient-specific based on compiled patient-specific analyte data over an adequate period of time. For example, where the analyte measured is glucose, a patient with consistently high glucose values may have a maximum configured threshold greater than a maximum configured threshold for a patient with consistently low glucose values. The maximum error threshold configured for the patient with consistently high glucose values may help to reduce false positive indications of failure generated by transmitter 360 by decreasing the likelihood of a high glucose value triggering the generation of an event indication by transmitter 360. Where the multiple consecutive event indications indicate that the sensed signals are below the minimum configured error threshold, the one or more root causes may include at least one of: analyte sensor 375 is failing, analyte sensor 375 has failed, detachment of analyte sensor 375 from the patient's body, compression on analyte sensor 375, wound trauma at an interface between analyte sensor 375 and the patient, low sensor sensitivity associated with analyte sensor 375, or deteriorated quality of a signal sensed by analyte sensor 375. As described herein, the root cause may not always be due to failure of analyte sensor 375 or detachment of analyte sensor 375 from the patient's body.

In some embodiments, multiple consecutive events indicating sensed signals are below a minimum configured error threshold may be due, at least in part, to compression on analyte sensor 375. Compression may include localized pressure on analyte sensor 375 causing a depletion of oxygen, or a decrease in the amount of oxygen, that may reach the patch site (e.g., reach the interface between analyte sensor 375 and the patient's body). A decrease or depletion in oxygen may result in artificially low signal or attenuated signal sensed by analyte sensor 375. As described herein, analyte sensor 375 may experience excessive pressure when a patient sleeps on their stomach. Additionally, compression issues may be more prevailing in children than adults, and at nighttime compared to daytime. Processor 335 may give these factors additional weight when determining whether compression on analyte sensor 375 is the cause of one or more errors associated with analyte sensor 375. For example, a plurality of event indications generated during the hours of 2:00 am and 4:00 am may be a good indication that compression is the underlying root cause.

In some embodiments, multiple consecutive events indicating sensed signals are below a minimum configured error threshold may be due, at least in part, to wound trauma at an interface between analyte sensor 375 and the patient (e.g., patch site). A wearable analyte sensor 375, including a continuous glucose monitor (CGM), may require the patient to insert a needle under their skin when deploying the analyte sensor 375. In some cases, inserting the needle may create a wound at the patch site. The wound may cause white blood cells to accumulate at the insertion site where the needle is inserted. These white blood cells may consume glucose locally around the insertion point and may cause a noticeable difference in capillary blood glucose versus glucose around analyte sensor 375 due to the fact that there is less glucose around the insertion site. Accordingly, the artificial differential in glucose may cause signals sensed by analyte sensor 375 to be very low. Wound trauma may be patient-specific; thus, processor 335 may take this into consideration when determining whether wound trauma is the cause of one or more errors associated with analyte sensor 375.

In some embodiments, multiple consecutive events indicating sensed signals are below a minimum configured error threshold may be due, at least in part, to deterioration of analyte sensor 375. Deterioration may decrease reliability of analyte sensor 375, and where analyte sensor 375 is not reliably tracking analyte, very low signals may be sensed by analyte sensor 375. Generally, exposure of analyte sensor 375 to prolonged or increased incidents of noise (e.g., unwanted effects on the signal) and/or higher degrees of noise may lead to deterioration of analyte sensor 375. In some cases, increased noise (correlating to deterioration of analyte sensor 375) may be due, at least in part, to placement of analyte sensor 375 under a patient's arm or at a pant line of the patient's stomach. Additionally, deterioration of analyte sensor 375 may be more prevalent as analyte sensor 375 nears the end of its "working period" (e.g., days eight through ten of the life of the sensor). Processor 335 may give these factors additional weight when determining whether deteriorated quality of a signal sensed by analyte sensor 375 is the cause of one or more errors associated with analyte sensor 375.

Error codes related to very high sensed signals may be generated by transmitter 360 when multiple consecutive events indicate that the sensed signals are above a maximum configured error threshold. Essentially, in such a case, transmitter 360 is detecting a short circuit. A short circuit may allow current to travel along an unintended path with no or very low electrical impedance which may result excessive current flowing through the circuit. The excessive current may trigger transmitter 360 to generate one or more event indications indicating errors codes in response to the very high sensed signals.

Where the multiple consecutive event indications indicate that the sensed signals are above the maximum configured error threshold, the one or more root causes may include at least one of: analyte sensor 375 is failing, analyte sensor 375 has failed, a malfunction associated with analyte sensor 375, high sensitivity of analyte sensor 375, damage to a membrane of the patient coupled to analyte sensor 375, or high moisture condition associated with analyte sensor 375. As described herein, the root cause may not always be due to failure of analyte sensor 375 or a malfunction associated with analyte sensor 375.

In some embodiments, multiple consecutive events indicating sensed signals are above a maximum configured error threshold may be due, at least in part, to analyte sensor 375 having a high sensitivity. Sensor sensitivity combined with high analyte concentrations of a patient may result in very high signals sensed by analyte sensor 375. Specifically, sensor current is a product of sensor sensitivity and glucose concentration of the patient, and when both of these factors are high, transmitter 360 may sense very high sensor current. For example, some patients may have very high glucose levels (e.g., 700-800 mg per deciliter) which may falsely trigger the maximum configured error threshold, especially where a sensitive analyte sensor is used by the patient.

In some cases, to prevent the false detection of analyte sensor 375 failure, processor 335 may differentiate between scenarios where a spike in the current has occurred versus scenarios where there is a relative change in the current. While gradual changes in the current may be realistic, a quick change/sudden spike in the current may be unrealistic and accurately represent analyte sensor 375 failure. For this reason, one or more of the plurality of event indications may correspond to a rate of change associated with the one or more sensed signals being higher than a threshold. Processor 335 may use this threshold to reduce the likelihood of high analyte values triggering an event indication indicating one or more errors associated with analyte sensor 375.

In some embodiments, multiple consecutive events indicating sensed signals are above a maximum configured error threshold may be due, at least in part, to damage to a membrane of the patient coupled to analyte sensor 375. For example, a tear in a patient's membrane may expose a working electrode of analyte sensor 375 to more surface area. By increasing the surface area the working electrode is exposed to, more current may be allowed to flow thereby causing transmitter 360 to see very high sensed signals and triggering the generation of one or more event indications corresponding to the very high sensed signals.

In some embodiments, multiple consecutive events indicating sensed signals are above a maximum configured error threshold may be due, at least in part, to a high moisture condition associated with analyte sensor 375. Moisture present at the interface may adversely affect signals sensed by analyte sensor 375. Accordingly, in some aspects, processor 335 may be further configured to receive moisture detection data indicating the high moisture condition. The moisture detection data may aid the root cause analysis in selecting or eliminating high moisture content as a likely cause of the error associated with analyte sensor 375. In other words, the moisture sensor may help prevent the false detection of analyte sensor 375 failure.

Error codes related to sensor calibration may be generated by transmitter 360 when a difference between one or more analyte measurements and one or more reference analyte measurements is greater than a threshold. Specifically, when one or more sensed signals indicate one or more analyte measurements, processor 335 may be further configured to receive one or more reference analyte measurements from a patient and transmit the one or more reference analyte measurements to transmitter 360. Transmitter 360 may be further configured to generate the plurality of event indications based on a comparison of one or more analyte measurements and the one or more reference analyte measurements received from processor 335. Accordingly, one or more root causes may include deficient sensor calibration when a difference between the one or more analyte measurements and the one or more reference analyte measurements is greater than a threshold. For example, reference analyte measurements may be measurements from a finger stick procedure performed by a patient.

A finger stick blood test may be used to measure the amount of certain substances in a patient's blood, by making a small prick into the patient's fingertip and collecting blood sample(s) to be used as one or more reference analyte measurements. Processor 335 may receive these reference analyte measurements from the patient and transmit them to transmitter 360 (e.g., transceiver 360 which may also be configured to receive). Transmitter 360 may receive the finger stick measurements from processor 335 and compare them to analyte measurements, for example glucose readings, transmitter 360 is receiving from analyte sensor 375. If the data sets (e.g., the finger stick measurements and glucose readings) match by a threshold (e.g., match by 20% or greater), then no further action may be taken by transmitter 360. However, if the data sets do not match by the threshold (e.g., match less than 20%), then transmitter 360 may take action to recalibrate analyte sensor 375 by generating event indications and transmitting the event indications to processor 335.

Error codes related to a residual operation failure mode may also be generated by transmitter 360. When analyte sensor 375 is exposed to light or moderate noise, one or more filters may be applied to "smooth" the raw sensor data. The filter signal may be compared to the raw sensor signal by transmitter 360. If the transmitter realizes a residual between these two streams (e.g., a differential between the raw signal and the filtered signal) has become too large, transmitter 360 may generate an event indication. The event indication may be representative of a residual operation failure mode.

In some embodiments, where multiple consecutive event indications indicate a residual operation failure mode, the one or more root causes may include compression on analyte sensor 375. For example, an onset to compression that is very steep may appear to transmitter 360 as a large differential between the raw signal and the filtered signal.

In some embodiments, where multiple consecutive event indications indicate a residual operation failure mode, the one or more root causes may include damage to a membrane of the patient coupled to analyte sensor 375. As described herein, a tear in a patient's membrane may expose the working electrode to more surface area. This may appear to transmitter 360 as a large differential between the raw signal and the filtered signal.

Referring back to FIG. 8, at block 812, operations 800 continue by the processor (e.g., processor 335) taking one or more actions to resolve the one or more root causes. According to certain aspects, processor 335 may engage in recommendation generation and implementation (e.g., in accordance with the fourth step of the root cause analysis process). In particular, where one or more root causes of an event indication or a plurality of event indications have been determined, processor 335 may be configured to take one or more actions to resolve the one or more root causes. In some cases, one or more actions may include autonomous (e.g., without outside instruction from a user, technical support personnel, etc.) actions taken by processor 335. In some cases, one or more actions may include the generation of one or more recommendations to be provided to a user, wherein the recommendations relate to suggestions or steps for minimizing or eliminating one or more root causes which led to generation of the one or more event indications. Recommendations may be patient-specific and vary for each patient/event indication combination analyzed by processor 335.

In some embodiments, one or more actions may include indicating to a user to relocate or reorient analyte sensor 375 on a body of the patient. As an example, processor 335 may determine one or more activities regularly engaged in by the patient, e.g., using methods described herein, and suggest a preferred site for deployment of analyte sensor 375. In another example, processor 335 may indicate to a user to relocate analyte sensor 375 to along lines of least deformation to decrease a likelihood of analyte sensor 375 falling off the body of the patient. In another example, processor 335 may suggest movement of analyte sensor 375 to a location of the patient's body having less hair. In another example, processor 375 may suggest a user change the orientation of analyte sensor 375 from a transverse wear to a longitudinal wear for purposes of increasing elasticity (e.g., elasticity of a patient's skin may be increased in the longitudinal direction) and reducing a likelihood of analyte sensor 375 falling off the body of the patient.

In some embodiments, one or more actions may include indicating to a user to change a position of the body of the patient. For example, processor 335 may suggest a user change a sleeping position of the patient at night where the patient was previously sleeping on his or her stomach thereby causing excessive compression to analyte sensor 375.

In some embodiments, one or more actions may include indicating to a user to change a diet of the patient. As an example, processor 335 may indicate to a user that the patient's sebum may be reduced by consuming low GI foods and reducing saturated fats. Specifically, processor 335 may suggest the patient reduce consumption of milk and/or other dairy product to decrease sebum content. In another example, the processor may suggest the patient increase their water intake to help mitigate TEWL and increase collagen function. While skin may shed regardless of measures taken by the patient, keeping the patient in a constant hydration state may be important to mitigate the amount and/or type of shedding, particularly around the patch site. In another example, processor 335 may suggest the patient increase consumption of linoleic acid containing foods during days following initial deployment of analyte sensor 375.

In some embodiments, one or more actions may include indicating to a user to apply a cream to an interface between analyte sensor 375 and the patient. As an example, processor 335 may suggest the patient apply creams containing hyaluronic acid which thermally stabilizes water and increases retention. In some cases, hyaluronic acid topic application may improve elasticity of the patient's skin by as much as 55% (varied results in literature) thereby reducing a likelihood of analyte sensor 375 becoming detached from the patient's body. As another example, where a patient regularly applies moisturizer to his or her body, processor 375 may suggest alternative moisturizing creams that are known to have minimal effects on adhesion of analyte sensor 375 to the patient's body.

In some embodiments, one or more actions may include indicating to a user to apply an agent to an interface between analyte sensor 375 and the patient. As an example, processor 335 may suggest the user apply an anti-inflammatory agent (e.g., methyl salicylate) topically on the patient's skin at the patch site. As another example, processor 335 may suggest the user apply a skin adhesion enhancer on the patient's skin at the patch site. Skin adhesion enhancers may include, but may not be limited to, diglycol, glycerin, sorbitol, oxctoxynol-9, dimethycone copolyol, diazolidinyl urea, methyparaben, isipropyl alcohol, partially hydrogenated rosin, gum mastic, styrax, alcohol (SDA-23), or methyl salicylate.

In some embodiments, one or more actions may include indicating to a user to have the patient digest one or more supplements to increase adhesion of analyte sensor 375 at the interface between analyte sensor 375 and the patient. As an example, processor 335 may suggest the patient take one or more supplements to increase the patient's collagen content. As another example, processor 335 may suggest the patient take anti-inflammation/histaminic suppressants to aid in the prevention of skin shedding.

In some embodiments, one or more actions may include indicating to a user that a specific activity has caused the one or more event indications. As an example, processor 335 may notify the user that excessive showering or swimming by the patient may be causing issues, described herein, with analyte sensor 375 of the patient. In addition, processor 335 may further suggest the patient prevent analyte sensor 375 from experiencing cycles of hydration/dehydration of analyte sensor 375 by decreasing showering and/or swimming activity of the patient. As another example, processor 335 may suggest the patient refrain from increased heart rate activities immediately following deployment of analyte sensor 375 to prevent excessive perspiration at the patch site.

In some embodiments, one or more actions may include indicating to the user to re-calibrate analyte sensor 375. In some embodiments, one or more actions may include indicating to the user to order a new analyte sensor for the patient. In some embodiments, one or more actions may include indicating to a user to order a new transmitter for the patient if a warranty period has expired.

As described herein, in some cases, one or more actions may include autonomous actions taken by processor 335. For example, in some embodiments, one or more actions may include ordering a new analyte sensor for the patient. In particular, the automated methods and systems may determine that a resolution of error(s) with a patient's continuous analyte monitoring system entails ordering of an analyte sensor replacement. Processor 335 may therefore order a replacement analyte sensor to be shipped to the patient. Processor 335 may subsequently create one or more invoices for the patient. Alternatively, if the sensor replacement is to be provided free of charge, the event may be recorded in appropriate company accounting databases as a tax-deductible eligible event. By consulting the patient's records, processor 335 may determine the delivery and shipment speed appropriate for the patient based on the urgency of the need to deliver a new replacement sensor. The patient may be notified via an email message, short message service (SMS), on-screen alert, or other means of communication. The patient may also be provided with shipment tracking information. In some embodiments, before ordering a replacement sensor, processor 335 may check the patient records to determine whether multiple sensors have been ordered within a short period of time. If the patient records show that the patient has ordered multiple sensors within a short period of time, processor 335 may flag the error ticket and request intervention from tech support personnel, by sending an email, on-screen alert or other means of communication.

While the above sections describe event indications indicating one or more errors associated with analyte sensor 375 and root causes that may correspond to each of these event indications, event indications indicating one or more errors not associated with analyte sensor 375 may be generated and root causes that may correspond to each of these event indications may be determined, as well. For example, event indications indicating one or more errors not associated with analyte sensor 375 may include one or more errors associated with transmitter 360, an application (e.g., analyte sensor application 330) executed by processor 335, or one or more other devices connected to processor 335 and/or applications executing on such connected In some embodiments, processor 335 of the continuous analyte monitoring system may be configured to, not only receive event indication data from transmitter 360, but also generate event indication data for performing root cause analysis. For example, processor 335 of FIG. 3B may generate a plurality of event indications and process the event indications to determine one or more root causes.

Figure 9:
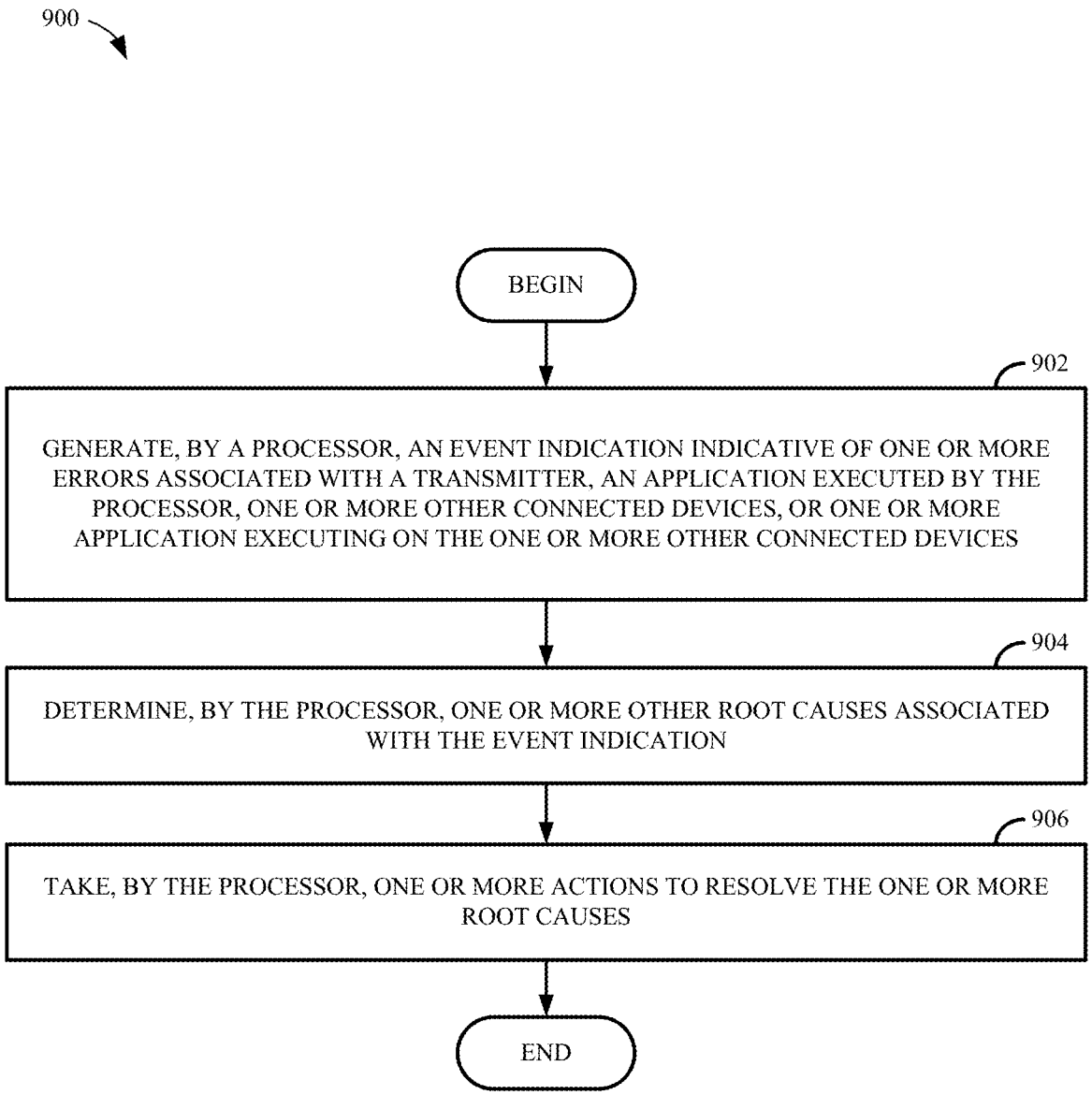
FIG. 9 illustrates a flow chart associated with an example method for automatically self-diagnosing and resolving performance problems detected and associated with a transmitter, an application, one or more other connected devices, or applications executing on such connected devices and associated with a continuous analyte monitoring system, in accordance with embodiments of the present technology.

FIG. 9 illustrates a flow chart 900 associated with an example method for automatically self-diagnosing and resolving performance problems detected and associated with a transmitter, an application, one or more other connected devices, or applications executing on such connected devices and associated with a continuous analyte monitoring system, in accordance with embodiments of the present technology. The operations 900 may be performed, for example, by components of a continuous analyte monitoring system, such as components of continuous analyte monitoring system 302 shown in FIG. 3B. For example, in certain embodiments, operations 900 may be performed by at least analyte sensor 375, transceiver 360 (also referred to herein as transmitter 360), and processor 335 of continuous analyte monitoring system 302 illustrated in FIG. 3B.

Operations 900 of FIG. 9 may, for example, be performed when transmitter 360 is unable to communicate with processor 335. Accordingly, only event indications generated by processor 335 may be analyzed to determine one or more root causes.

At block 902, operations 900 begin by a processor (e.g., processer 335) generating an event indication indicative of one or more errors associated with a transmitter (e.g., transmitter 360), an application (e.g., analyte sensor application 330) executed by the processor (e.g., processor 335), one or more other connected devices, or one or more applications executing on the one or more other connected devices.

Each of the plurality of event indications generated by processor 335 may indicate errors, including but not limited to, (1) errors related to a battery and warranty period of transmitter 360, (2) errors related to initial pairing of transmitter 360 and processor 335, (3) errors related to a lost connection between transmitter 360 and processor 335, (4) errors related to an inability of processor 335 to connect to a server (e.g., server system 334), (5) errors related to a lost connection between processor 335 and server system 334, (6) errors related to authorization failure at server system 334, (7) errors related to internal server system 334 issues, (8) errors related to an inability of processor 335 to connect to one or more other devices, (9) errors related to a lost connection between processor 335 and one or more other devices, (10) errors related to the receipt of incorrect data at processor 335 by a third-party application, or any combination thereof.

Event indications indicating errors associated with the transmitter (e.g., errors (1)-(3) described above) may be generated when transmitter 360 is not functioning properly, for example, transmitter 360 is unable to communicate analyte date and/or one or more event indications (described with respect to FIG. 8) to processor 335.

In some embodiments, event indications indicating errors related to a battery and warranty period of transmitter 360 may be generated by processor 335 when there is an issue with a battery of transmitter 360 and transmitter 360 is unable to communicate with processor 335.

In some embodiments, event indications indicating errors related to an initial pairing of transmitter 360 and processor 335 may be generated by processor 338 when an initial pairing between transmitter 360 and processor 335 has failed, essentially identifying that processor 335 cannot find transmitter 360.

In some embodiments, event indications indicating errors related to an inability of processor 335 to connect to server system 334 and errors related to a lost connection between processor 335 and server system 334 may be generated by processor 335 when a host/domain name of server system 334 cannot be found by processor 335, a time out error occurs, connection is refused by server system 334, or server system 334 fails to produce a response within a predetermined set time. A time out error may occur when server system 334 is located using its host/domain name, but a connection is unable to be established to a port of server system 334 within a predetermined amount of time. A connection refused by server system 334 may occur when server system 334 is found by processor 335 using its host/domain name, but server system 334 refuses to accept the connection to processor 335. Server system 334 may fail to produce a response within a predetermined set time when server system 334 is located using its host/domain name and a connection is established with a port of server system 334, but server system 334 does not respond with a predetermined amount of time.

In some embodiments, event indications indicating errors related to authorization failure at server system 334 may be generated by processor 335 when the pairing requires user authentication and processor 335 has failed to accurately provide authorization.

In some embodiments, event indications indicating errors related to internal server system 334 issues may be generated by processor 335 when server system 334 encounters an unexpected condition which prevents server system 334 from fulfilling a request (e.g., unable to push requested reports back to processor 335).

In some embodiments, event indications indicating errors related to one or more other connected devices (e.g., sensor devices including a pump, other analyte sensors, third-party devices such as FitBit, etc.) and/or applications executing thereon may be generated by processor 335 when processor 335 is unable to connect to the one or more other devices, when there is a lost connection between processor 335 and one or more other devices, or when processor 335 receives incorrect data from a third-party application.

Additionally, although not illustrated in FIG. 9, in some cases where transmitter 360 is a "dummy transmitter" as described herein, processor 335 may be configured to generate a plurality of sensor-triggered event indications (e.g., event indications indicating one or more errors associated with analyte sensor 375), instead of these event indications being generated by transmitter 360, as illustrated with respect to FIG. 8.

According to certain aspects, processor 335, after generating these event indications, may analyze whether a root cause of the generation of these indications corresponds to a prematurely failing transmitter 360, an already failed transmitter 360, errors that may based, at least in part, on some other reason (e.g., user error), explained in detail below, and may be fixed by configuring processor 335 to take one or more corrective actions, or errors that may be associated with other connected devices or applications executing thereon.

Accordingly, at block 904, operations 900 continue by the processor (e.g., processer 335) determining one or more root causes associated with the event indication generated by the processor.

For example, in some embodiments, where event indications indicate errors related to a battery and warranty period of transmitter 360 (e.g., generated by processor 335 when there is an issue with a battery of transmitter 360 and transmitter 360 is unable to communicate with processor 335), processor 335 may be further configured to determine whether a warranty period associated with transmitter 360 has expired. For example, a warranty period for transmitter 360 may start from a first date of activation of transmitter 360 (e.g., at time t=0 days) and be in effect for 90 days (e.g., until time t=90 days). During the effective warranty period, any malfunction or failure occurring under normal use with respect to the transmitter 360 may result in replacement of transmitter 360 at no cost to the patient. However, outside of the effective warranty period (e.g., when t>90 days) transmitter 360 may be replaced at the patient's expense.

In some embodiments, where the generated event indication indicates an initial pairing of transmitter 360 and processor 335 has failed, the one or more root causes may include that transmitter 360 is failing or transmitter 360 which has already failed. For example, when activating transmitter 360, a user must follow steps provided on a display device housing processor 335 or an application executed by processor 335. The user may scan or manually enter the serial number of transmitter 360 for pairing. The application or display device may scan for that serial number, and where a match is found, a connection may be established between transmitter 360 and processor 335. Where "handshaking" between transmitter 360 and processor 335 is accomplished, the pairing may be considered to be successful; however, in cases where transmitter 360 is failing, or has already failed, "handshaking" between transmitter 360 and processor 335 may not be successful. For example, transmitter 360 may be dead, thus no serial number may be located by processor 335 for coordination of the pairing.

In some embodiments, where the generated event indication indicates an initial pairing between transmitter 360 and processor 335 has failed, the one or more root causes may include an inaccurately installed transmitter 360. For example, incorrect placement of transmitter 360 (with respect to other components of the continuous analyte monitoring system) by a user may not allow for successful activation of transmitter 360.

In some embodiments, where the generated event indication indicates an initial pairing between transmitter 360 and processor 335 has failed, the one or more root causes may include a failure to activate transmitter 360 based, at least in part, on entry of an inaccurate serial number. Each serial number may be a unique, identifying number or group of numbers and letters assigned to every manufactured transmitter 360; therefore, entry of an incorrect serial number may create user error affecting an ability of processor 335 to pair with transmitter 360.

In some embodiments, where the generated event indication indicates an initial pairing between transmitter 360 and processor 335 has failed, the one or more root causes may include a failure to activate transmitter 360 based, at least in part, on failure to acknowledge a pairing pop-up message. For example, when pairing two or more devices, a user may be required to acknowledge (e.g., accept the pairing terms, conditions, etc.) a pop-up message on a user's display device (e.g., an iOS pop-up message on a user's phone) to complete the pairing. As an example, a pop-up message may appear asking the user whether a Bluetooth pairing to a device attempting to connect to the user's display device may be allowed. Where the user does not accept the message or waits too long to accept the message (e.g., pop-up messages may only display for a limited time), then the pairing may be incomplete thereby causing processor 335 to generate an event indication indicating such an error.

In some embodiments, where the generated event indication indicates an error related to a lost connection between transmitter 360 and processor 335 (e.g., generated when an initial pairing between transmitter 360 and processor 335 has been lost, although previously connected), processor 335 may determine an issue exists with respect to the connection when, after a threshold amount of time (e.g., fifteen minutes), processor 335 has not received one or more signals (e.g., packets) from transmitter 360. The connection loss may be related to an issue with transmitter 360 or an issue with the application executed by processor 335 (e.g., application has been swipe killed, application malfunction, Bluetooth malfunction, etc.).

In some embodiments, where the generated event indication indicates a connection loss between transmitter 360 and processor 335, the one or more root causes may include transmitter 360 is failing or transmitter 360 has already failed. In particular, the event indication may indicate an error comprising a permanent loss of connection, thus, transmitter 360 may need to be replaced. To ascertain whether the error corresponds to a permanent or temporary loss of connection, processor 335 may be further configured to indicate to a user to take one or more remedial actions. As a first action, processor 335 may request the user confirm the application is still running, and if not, the user may be requested to open the application. For example, a user may have inadvertently swipe killed the application causing the application to not be running in the background. Where connection is re-established after the request of processor 335 is fulfilled, remedial action may conclude. Where connection is not re-established, processor 335 may determine additional action is required. As a second action, processor 335 may request the user turn off and on their Bluetooth. Processor 335 may wait a threshold amount of time after initiating this request to before concluding whether connection has been re-established or connection has not been re-established and additional action is required.

In some cases, processor 335 may autonomously test the Bluetooth connection without prompting or requiring action by the user. As a third action, processor 335 may indicate to the user to user swipe kill and reopen the application. Where connection is re-established after the processor's request is fulfilled, remedial action may conclude. Where connection is not re-established, processor 335 may determine additional action is required. As a fourth action, processor 335 may indicate to the user to uninstall and re-install the application. In some cases, remedial action steps one through four may be automated. If remedial action steps one through four are unsuccessful in re-establishing a connection between processor 335 and transmitter 360, processor 335 may determine the error is related to a permanent loss of connection due, at least in part, to a failing or failed transmitter 360.

In some embodiments, where the generated event indication indicates errors related to an inability of processor 335 to connect to server system 334 and errors related to a lost connection between processor 335 and server system 334 because a host/domain name of server system 334 cannot be found by processor 335, the one or more root causes may indicate a problem exists with respect to a domain name system (DNS) or connectivity to the DNS.

In some embodiments, where the generated event indication indicates errors related to an inability of processor 335 to connect to server system 334 and errors related to a lost connection between processor 335 and server system 334 because a time out error occurs, the one or more root causes may indicate an issue with one or more routers or a firewall, a web server hardware failure, or general internet connectivity problems.

In some embodiments, where the generated event indication indicates errors related to an inability of processor 335 to connect to server system 334 and errors related to a lost connection between processor 335 and server system 334 because connection is refused by server system 334, the one or more root causes may indicate a problem exists with web server software.

In some embodiments, where the generated event indication indicates errors related to an inability of processor 335 to connect to server system 334 and errors related to a lost connection between processor 335 and server system 334 because server system 334 fails to produce a response within a predetermined set time, the one or more root causes may indicate an issue with web server software or back-end systems or an overloaded server.

In some embodiments, where the generated event indication indicates errors related to related to authorization failure at server system 334, the one or more root causes may indicate processor 335 has failed to accurately provide authorization or an issue with server system 334 because although server system 334 may understand the authorization request server system 334 is refusing to fulfill it.

In some embodiments, where the generated event indication indicates errors related to internal server system 334 issues, the one or more root causes may indicate an issue with server system 334. In some embodiments, where the generated event indication indicates errors related to one or more other connected devices (e.g., sensor devices including a pump, other analyte sensors, third-party devices such as FitBit, etc.) and/or applications executing thereon, the one or more root causes may indicate an issue with one or more other connected devices and/or applications executing thereon.

And at block 906, operations 900 continue by the processor (e.g., processor 335) taking one or more actions to resolve the one or more root causes. As described with respect to block 812 of FIG. 8, processor 335 may engage in recommendation generation and implementation (e.g., in accordance with the fourth step of the root cause analysis process). In particular, where one or more root causes of an event indication or a plurality of event indications have been determined, processor 335 may be configured to take one or more actions to resolve the one or more root causes. In addition to the one or more actions described with respect to block 812 of FIG. 8, in some embodiments, the one or more actions may include actions described below for each of the identified root causes.

In some embodiments, where the warranty period associated with transmitter 360 has expired, one or more actions may include processor 335 indicating to a user to order a new transmitter for the patient. However, in some embodiments, where the warranty period associated with transmitter 360 has not expired, one or more actions may include processor 335 ordering a new transmitter for the patient. Processor 335 may therefore order a replacement transmitter to be shipped to the patient. Processor 335 may subsequently create one or more invoices for the patient. Alternatively, if the transmitter replacement is to be provided free of charge, the event may be recorded in appropriate company accounting databases as a tax-deductible eligible event. By consulting the patient's records, processor 335 may determine the delivery and shipment speed appropriate for the patient based on the urgency of the need to deliver a new replacement transmitter. The patient may be notified via an email message, SMS, on-screen alert, or other means of communication. The patient may also be provided with shipment tracking information. In some embodiments, before, ordering a replacement transmitter, processor 335 may check the patient records to determine whether multiple transmitters have been ordered within a short period of time. If the patient records show that the patient has ordered multiple transmitters within a short period of time, processor 335 may flag the error ticket and request intervention from tech support personnel, by sending an email, on-screen alert or other means of communication.

In some embodiments, one or more actions may include indicating to a user to re-scan or re-enter the serial number of transmitter 360 for pairing. In some embodiments, one or more actions may include indicating to a user to re-attempt placement of the transmitter such that it is correctly installed with respect to other components of continuous analyte monitoring system 302. In some embodiments, one or more actions may include indicating to a user that a previous pairing pop-up has failed to be acknowledged and further indicate to the user to attempt pairing again by re-installing transmitter 360 and acknowledging the pairing pop-up message.

As described previously, in some embodiments, one or more actions may include indicating to a user to take one or more remedial actions.

In some embodiments, one or more actions may include indicating to a user to check whether a firewall is blocking connection between server system 334 and continuous analyte monitoring system 302. In some embodiments, one or more actions may include indicating to a user to check hardware of server system 334 for any issues. In some embodiments, one or more action may include indicating to a user to check whether there are any issues with internet connectivity. In some embodiments, one or more actions may include indicating to a user to check whether server system 334 is running properly, and if so, whether server system 334 is overloaded. In either case, processor 335 may indicate to the user to fix the server system 334 if server system 334 is overloaded or not functioning properly.

In some embodiments, one or more actions may include indicating to a user to check whether one or more other connected devices (e.g., sensor devices including a pump, other analyte sensors, third-party devices such as FitBit, etc.) and/or applications executing thereon are running properly. Further, processor 335 may indicate to the user to fix a connected device and/or an applications executing thereon if the user determines an issue is present.

While FIG. 8 illustrates event indications generated by only transmitter 360 of the continuous analyte monitoring system and FIG. 9 illustrates event indications generated by only processor 335 of the continuous analyte monitoring system, in some embodiments, both transmitter 360 and processor 335 may generate event indications. However, in such a scenario processor 335 may only generate event indications indicating one or more errors associated with transmitter 360, when an initial (successful) connection between transmitter 360 and processor 335 has been lost. Otherwise, transmitter 360 may only generate event indications indicating one or more errors associated with an application (e.g., analyte sensor application 330) executed by processor 335, one or more other connected devices, or one or more applications executing on the one or more other connected devices while transmitter 360 generates event indications indicating one or more errors associated with analyte sensor 375.

The disclosed systems and methods herein provide a systematic process for finding and identifying the root causes of problems and issues related to a patient's continuous analyte monitoring system According to aspects described herein, automated root cause analysis aims to both solve a patient's reported problem in an efficient and reliable manner and prevent similar problems from occurring in the future. In particular, by determining root causes of false positive failure detections related to one or more components in the continuous analyte monitoring system, the system may indicate be able to identify proper corrective action and relay this information such that similar problems are avoided in the future. Additionally, this may allow for more reliable detection of one or more failing components of the continuous analyte monitoring system so that they may be replaced efficiently. Efficient replacement may be vital to the health and safety of patients whom rely on their continuous analyte monitoring systems to identify when serious health issues arise.

For ease of explanation and illustration, in some instances the detailed description describes exemplary systems and methods in terms of a continuous glucose monitoring environment; however it should be understood that the scope of the invention is not limited to that particular environment, and that one skilled in the art will appreciate that the systems and methods described herein can be embodied in various forms. Accordingly any structural and/or functional details disclosed herein are not to be interpreted as limiting the systems and methods, but rather are provided as attributes of a representative embodiment and/or arrangement for teaching one skilled in the art one or more ways to implement the systems and methods, which may be advantageous in other contexts.

For example, and without limitation, described monitoring systems and methods may include sensors that measure the concentration of one or more analytes (for instance glucose, lactate, potassium, pH, cholesterol, isoprene, and/or hemoglobin) and/or other blood or bodily fluid constituents of or relevant to a host and/or another party.

By way of example, and without limitation, monitoring system and method embodiments described herein may include finger-stick blood sampling, blood analyte test strips, non-invasive sensors, wearable monitors (e.g., smart bracelets, smart watches, smart rings, smart necklaces or pendants, workout monitors, fitness monitors, health and/or medical monitors, clip-on monitors, and the like), adhesive sensors, smart textiles and/or clothing incorporating sensors, shoe inserts and/or insoles that include sensors, transdermal (i.e. transcutaneous) sensors, and/or swallowed, inhaled or implantable sensors.

In some embodiments, and without limitation, monitoring systems and methods may comprise other sensors instead of or in additional to the sensors described herein, such as inertial measurement units including accelerometers, gyroscopes, magnetometers and/or barometers; motion, altitude, position, and/or location sensors; biometric sensors; optical sensors including for instance optical heart rate monitors, photoplethysmogram (PPG)/pulse oximeters, fluorescence monitors, and cameras; wearable electrodes; electrocardiogram (EKG or ECG), electroencephalography (EEG), and/or electromyography (EMG) sensors; chemical sensors; flexible sensors for instance for measuring stretch, displacement, pressure, weight, or impact; galvanometric sensors, capacitive sensors, electric field sensors, temperature/thermal sensors, microphones, vibration sensors, ultrasound sensors, piezoelectric/piezoresistive sensors, and/or transducers for measuring information of or relevant to a host and/or another party.

In this document, the terms "computer program medium" and "computer usable medium" and "computer readable medium", as well as variations thereof, are used to generally refer to transitory or non-transitory media such as, for example, main memory, storage unit interface, removable storage media, and/or channel. These and other various forms of computer program media or computer usable/readable media may be involved in carrying one or more sequences of one or more instructions to a processing device for execution. Such instructions embodied on the medium, may generally be referred to as "computer program code" or a "computer program product" or "instructions" (which may be grouped in the form of computer programs or other groupings). When executed, such instructions may enable the computing module or a processor thereof or connected thereto to perform features or functions of the present disclosure as discussed herein.

Various embodiments have been described with reference to specific example features thereof. It will, however, be evident that various modifications and changes may be made thereto without departing from the broader spirit and scope of the various embodiments as set forth in the appended claims. The specification and figures are, accordingly, to be regarded in an illustrative rather than a restrictive sense.

Although described above in terms of various example embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the present application, whether or not such embodiments are described and whether or not such features are presented as being a part of a described embodiment. Thus, the breadth and scope of the present application should not be limited by any of the above-described example embodiments.

Terms and phrases used in the present application, and variations thereof, unless otherwise expressly stated, should be construed as open ended as opposed to limiting. As examples of the foregoing: the term "including" should be read as meaning "including, without limitation" or the like; the term "example" is used to provide illustrative instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed in multiple groupings or packages or across multiple locations.

Additionally, the various embodiments set forth herein are described in terms of example block diagrams, flow charts, and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

What is claimed is:

1. A continuous analyte monitoring system, comprising:
    an analyte sensor configured to sense analyte levels of a patient to generate one or more sensed signals;
    a transmitter configured to:
        receive the one or more sensed signals,
        process the one or more sensed signals to generate a plurality of event indications based on the one or more sensed signals, the plurality of generated event indications indicating one or more errors associated with the analyte sensor, and
        transmit the plurality of generated event indications; and
    a processor configured to:
        receive the plurality of generated event indications;
        detect a failure of the analyte sensor based on the plurality of generated event indications;
        determine one or more root causes of the failure of the analyte sensor based on a pattern associated with the plurality of generated event indications; and
        take one or more actions to resolve the one or more root causes.

2. The continuous analyte monitoring system of claim 1, wherein each of the plurality of generated event indications indicates whether the sensed signals are above a maximum configured error threshold or below a minimum configured error threshold.

3. The continuous analyte monitoring system of claim 1, wherein the pattern associated with the plurality of generated event indications indicates multiple consecutive event indications indicative of the sensed signals being above a maximum configured error threshold.

4. The continuous analyte monitoring system of claim 3, wherein, when the multiple consecutive event indications indicate that the sensed signals are above the maximum configured error threshold, the one or more root causes comprise at least one of:
    a malfunction associated with the analyte sensor;
    high sensitivity of the analyte sensor;
    damage to a membrane of the patient coupled to the analyte sensor; or
    high moisture condition associated with the analyte sensor.

5. The continuous analyte monitoring system of claim 4, further comprising:
    a moisture sensor configured to determine a moisture level at an interface between the analyte sensor and the patient to generate moisture detection data, and
    wherein the processor is further configured to receive the moisture detection data.

6. The continuous analyte monitoring system of claim 1, wherein the pattern associated with the plurality of generated event indications indicates multiple consecutive event indications indicative of the sensed signals being below a minimum configured error threshold.

7. The continuous analyte monitoring system of claim 6, wherein, when the multiple consecutive event indications indicate that the sensed signals are below the minimum configured error threshold, the one or more root causes comprise at least one of:
    compression on the analyte sensor;
    wound trauma at an interface between the analyte sensor and the patient;
    low sensor sensitivity associated with the analyte sensor; or
    deteriorated quality of a signal sensed by the analyte sensor.

8. The continuous analyte monitoring system of claim 1, wherein:
    the one or more sensed signals indicate one or more analyte measurements;
    the processor is further configured to:
        receive one or more reference analyte measurements from the patient; and
        transmit the one or more reference analyte measurements to the transmitter; and
    the transmitter is further configured to generate the plurality of generated event indications based on a comparison of the one or more analyte measurements and the one or more reference analyte measurements.

9. The continuous analyte monitoring system of claim 8, wherein determining the one or more root causes comprises determining that a difference between the one or more analyte measurements and the one or more reference analyte measurements is greater than a threshold; and
    wherein the one or more root causes comprise deficient sensor calibration.

10. The continuous analyte monitoring system of claim 1, wherein one or more of the plurality of generated event indications indicate a rate of change associated with the one or more sensed signals being higher than a threshold.

11. The continuous analyte monitoring system of claim 1, wherein:
the transmitter is further configured to apply one or more filters to the one or more sensed signals to produce one or more filtered signals; and
each of the plurality of generated event indications indicates whether a differential between the one more sensed signals and the one or more filtered signals is above a configured threshold.

12. The continuous analyte monitoring system of claim 11, wherein:
determining the one or more root causes comprises determining multiple consecutive event indications indicate the differential between the one more sensed signals and the one or more filtered signals is above a configured threshold; and
wherein the one or more root causes comprise at least one of:
compression on the analyte sensor; or
damage to a membrane of the patient coupled to the analyte sensor.

13. The continuous analyte monitoring system of claim 1, wherein the processor is further configured to receive one or more answers to one or more questions presented to a user, and wherein the determining of the one or more root causes is further based on the one or more answers.

14. The continuously analyte monitoring system of claim 13, wherein the one or more questions comprise at least one of:
one or more questions associated with a skin condition of the patient;
one or more questions associated with recent activities of the patient;
one or more questions associated with one or more health conditions of the patient;
one or more questions associated with nutrition of the patient;
one or more questions associated with an interface between the analyte sensor and the patient; or
one or more questions associated with deployment of the analyte sensor by the patient.

15. The continuous analyte monitoring system of claim 1, wherein the one or more actions comprise at least one of:
indicating to a user to relocate or reorient the analyte sensor on a body of the patient;
indicating to the user to change a position of the body of the patient;
indicating to the user to change a diet of the patient;
indicating to the user to apply a cream to an interface between the analyte sensor and the patient;
indicating to the user to apply an agent to an interface between the analyte sensor and the patient;
indicating to the user to have the patient digest one or more supplements to increase adhesion of the analyte sensor at the interface between the analyte sensor and the patient;
indicating to the user that a specific activity has caused one or more of the plurality of generated event indications;
indicating to the user to re-calibrate the analyte sensor;
indicating to the user to order a new analyte sensor for the patient; or
ordering a new analyte sensor for the patient.

16. The continuous analyte monitoring system of claim 1, wherein the processor is further configured to receive secondary sensor data associated with the patient, wherein the determining of the one or more root causes is further based on the secondary sensor data.

17. The continuous analyte monitoring system of claim 16, wherein the secondary sensor data comprises at least one:
accelerometer data associated with movement of the analyte sensor;
temperature data indicating a temperature associated with the analyte sensor;
gyrometer data indicating an orientation of the analyte sensor;
moisture detection data indicating a moisture level at an interface between the analyte sensor and the patient; or
heart sensor data indicating a heart rate of the patient.

18. The continuous analyte monitoring system of claim 1, wherein the processor is further configured to receive an indication from a server indicating a pattern associated with event indications for a population of patients, wherein determining the one or more root causes is further based on the pattern associated with the event indications for the population.

19. The continuous analyte monitoring system of claim 1, wherein the processor is further configured to:
generate an event indication indicative of one or more errors associated with:
the transmitter,
an application executed by the processor,
one or more other connected devices, or
one or more applications executing on the one or more other connected devices; and
determine one or more other root causes associated with the event indication generated by the processor.

20. The continuous analyte monitoring system of claim 19, wherein the event indication generated by the processor indicates an issue with a battery of the transmitter.

21. The continuous analyte monitoring system of claim 20, wherein the processor is further configured to determine whether a warranty period associated with the transmitter has expired, wherein the one or more actions comprise:
indicating to a user to order a new transmitter for the patient upon determining the warranty period has expired; or
ordering a new transmitter for the patient upon determining the warranty period has not expired.

22. The continuous analyte monitoring system of claim 19, wherein the event indication generated by the processor indicates an initial pairing between the transmitter and the processor has failed.

23. The continuous analyte monitoring system of claim 19, wherein the event indication generated by the processor indicates that a connection between the transmitter and the processor has been lost for a period greater than a threshold; and
wherein the processor is further configured to indicate to a user to take one or more remedial actions comprising, at least one of:
indicating to a user to disable and re-enable a Bluetooth function on a device where the processor is running;
indicating to the user to power cycle the device where the processor is running; or
indicating to the user to uninstall and re-install the application executed by the processor.

24. The continuous analyte monitoring system of claim 19, wherein the one or more actions comprise at least one of:
indicating to a user to uninstall and re-install the application executed by the processor; or indicating to the user to reopen the application executed by the processor.

25. The continuous analyte monitoring system of claim 19, wherein the event indication generated by the processor indicates an initial pairing between the one or more other connected devices and the processor has failed.

26. The continuous analyte monitoring system of claim 25, wherein the initial pairing fails due, at least in part, to the one or more other connected devices refusing authorization of the processor.

27. The continuous analyte monitoring system of claim 19, wherein the event indication generated by the processor indicates receipt, by the processor, of incorrect data transmitted by the one or more applications executing on the one or more other connected devices.

28. A method comprising:
sensing, by an analyte sensor, analyte levels of a patient to generate one or more sensed signals;
receiving, by a transmitter, the one or more sensed signals;
processing, by the transmitter, the one or more sensed signals to generate a plurality of event indications based on the one or more sensed signals, the plurality of generated event indications indicating one or more errors associated with the analyte sensor;
transmitting, by the transmitter, the plurality of generated event indications to a processor;
receiving, by the processor, the plurality of generated event indications;
detecting, by the processor, a failure of the analyte sensor based on the plurality of generated event indications;
determining, by the processor, one or more root causes of the failure of the analyte sensor based on a pattern associated with the plurality of generated event indications; and
taking, by the processor, one or more actions to resolve the one or more root causes.

29. The method of claim 28, further comprising:
generating, by the processor, an event indication indicative of one or more errors associated with:
the transmitter,
an application executed by the processor,
one or more other connected devices, or
one or more applications executing on the one or more other connected devices; and
determining, by the processor, one or more other root causes associated with the event indication generated by the processor.

* * * * *